(12) United States Patent
Wilson et al.

(10) Patent No.: US 9,375,690 B2
(45) Date of Patent: Jun. 28, 2016

(54) FLUIDICS APPARATUS AND FLUIDICS SUBSTRATE

(75) Inventors: Rab Wilson, Glasgow (GB); Jonathan M. Cooper, Glasgow (GB); Julien Reboud, Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 956 days.

(21) Appl. No.: 13/391,762

(22) PCT Filed: Aug. 24, 2010

(86) PCT No.: PCT/GB2010/001600
§ 371 (c)(1),
(2), (4) Date: Feb. 22, 2012

(87) PCT Pub. No.: WO2011/023949
PCT Pub. Date: Mar. 3, 2011

(65) Prior Publication Data
US 2012/0149126 A1 Jun. 14, 2012

(30) Foreign Application Priority Data
Aug. 24, 2009 (GB) .................................. 0914762.0

(51) Int. Cl.
*G01N 1/00* (2006.01)
*B06B 1/00* (2006.01)
(Continued)

(52) U.S. Cl.
CPC ......... *B01F 13/0071* (2013.01); *B01F 11/0266* (2013.01); *B01J 19/0093* (2013.01);
(Continued)

(58) Field of Classification Search
CPC ................. B01J 19/0093; B01J 2219/00783; B01J 2219/00824; B01J 2219/00828; B01J 2219/00837; B01J 2219/0086; B01J 2219/00873; B01J 2219/00889; B01J 2219/00905; B01J 2219/00932; B01J 2219/00952; B01F 11/0266; B01F 13/001; B01L 3/502792; B01L 2200/10; B01L 2300/0816; B01L 2300/0864; B01L 2300/0867; B01L 2300/089; B01L 2400/0436; B01L 2400/0439; B01L 2400/0496; Y10T 436/25125

See application file for complete search history.

(56) References Cited

U.S. PATENT DOCUMENTS 4,336,514 A 6/1982 Paige
5,455,178 A 10/1995 Fattinger
(Continued)

FOREIGN PATENT DOCUMENTS

CN 1455985 11/2003
CN 2744401 Y 12/2005
(Continued)

OTHER PUBLICATIONS

Bloch, P. D. et al. "Selective reflection of surface acoustic waves by periodic dot arrays." IEEE Ultrasonics Symposium (1979) 687-690.*
(Continued)

*Primary Examiner* — Christopher A Hixson
(74) *Attorney, Agent, or Firm* — Swanson & Bratschun, L.L.C.

(57) ABSTRACT

A fluidics apparatus is disclosed for manipulation of at least one fluid sample, typically in the form of a droplet. The apparatus has a substrate surface with a sample manipulation zone for location of the fluid sample. A transducer arrangement such as an interdigitated electrode structure on a piezoelectric body provides surface acoustic waves at the substrate surface for manipulation of the fluid sample. The substrate surface has an arrangement of surface acoustic wave scattering elements forming a phononic crystal structure for affecting the transmission, distribution and/or behavior of surface acoustic waves at the substrate surface. Also disclosed is a method for lysing a cell. In this method, the cell is comprised in a fluid sample contacting a substrate surface, the method comprising providing surface acoustic waves at the substrate surface, such that the cell lyses.

9 Claims, 23 Drawing Sheets

(51) Int. Cl.

| | | |
|---|---|---|
| B01F 13/00 | (2006.01) | |
| B01F 11/02 | (2006.01) | |
| B01J 19/00 | (2006.01) | |
| B01L 3/00 | (2006.01) | |

(52) U.S. Cl.
CPC .... *B01L3/502792* (2013.01); *B01J 2219/0086* (2013.01); *B01J 2219/00783* (2013.01); *B01J 2219/00824* (2013.01); *B01J 2219/00828* (2013.01); *B01J 2219/00837* (2013.01); *B01J 2219/00873* (2013.01); *B01J 2219/00889* (2013.01); *B01J 2219/00905* (2013.01); *B01J 2219/00932* (2013.01); *B01J 2219/00952* (2013.01); *B01L 2200/10* (2013.01); *B01L 2300/089* (2013.01); *B01L 2300/0816* (2013.01); *B01L 2300/0864* (2013.01); *B01L 2300/0867* (2013.01); *B01L 2400/0436* (2013.01); *B01L 2400/0439* (2013.01); *B01L 2400/0496* (2013.01); *Y10T 436/25125* (2015.01)

(56) References Cited

U.S. PATENT DOCUMENTS

| | | | |
|---|---|---|---|
| 5,906,549 | A | 5/1999 | Kubica |
| 6,210,128 | B1 | 4/2001 | Rife |
| 6,362,543 | B1 | 3/2002 | Ellis |
| 6,459,080 | B1 | 10/2002 | Yin |
| 6,568,052 | B1 | 5/2003 | Rife |
| 6,603,118 | B2 | 8/2003 | Ellson |
| 6,707,038 | B2 | 3/2004 | Ellson |
| 6,710,335 | B2 | 3/2004 | Ellson |
| 6,739,531 | B2 | 5/2004 | Taylor |
| 6,777,245 | B2 | 8/2004 | Wixforth |
| 6,809,315 | B2 | 10/2004 | Ellson |
| 6,855,925 | B2 | 2/2005 | Ellson |
| 6,867,415 | B2 | 3/2005 | Hughey et al. |
| 7,103,949 | B2 | 9/2006 | Rife |
| 7,172,897 | B2 | 2/2007 | Blackburn |
| 7,405,395 | B2 | 7/2008 | Ellson |
| 7,459,304 | B2 | 12/2008 | Gauer |
| 7,731,412 | B2 | 6/2010 | Sparey-Taylor |
| 7,880,563 | B2 | 2/2011 | Khelif |
| 7,942,568 | B1 | 5/2011 | Branch |
| 8,415,619 | B2 | 4/2013 | Goodlett |
| 2001/0055529 | A1 | 12/2001 | Wixforth |
| 2003/0175947 | A1 | 9/2003 | Liu |
| 2004/0042915 | A1 | 3/2004 | Rife |
| 2004/0101975 | A1 | 5/2004 | Gauer |
| 2004/0115097 | A1 | 6/2004 | Wixforth |
| 2004/0257906 | A1 | 12/2004 | Scriba |
| 2006/0060769 | A1 | 3/2006 | Bousse |
| 2006/0223185 | A1 | 10/2006 | Federov et al. |
| 2007/0128046 | A1 | 6/2007 | Gonnella |
| 2007/0140041 | A1 | 6/2007 | Sparey-Taylor |
| 2007/0252083 | A1 | 11/2007 | Arscott |
| 2007/0264161 | A1 | 11/2007 | Rathgeber |
| 2008/0094937 | A1 | 4/2008 | Li |
| 2008/0211602 | A1 | 9/2008 | Khelif |
| 2009/0098027 | A1 | 4/2009 | Tabata |
| 2010/0139377 | A1 | 6/2010 | Huang |
| 2010/0191277 | A1 | 7/2010 | McEwen |
| 2010/0200092 | A1 | 8/2010 | Beltram |
| 2010/0206696 | A1 | 8/2010 | Kondoh |
| 2012/0145890 | A1 | 6/2012 | Goodlett |
| 2012/0149126 | A1 | 6/2012 | Wilson |
| 2013/0213488 | A1 | 8/2013 | Weitz |
| 2013/0330247 | A1 | 12/2013 | Wilson |
| 2014/0083174 | A1 | 3/2014 | Rebound |

FOREIGN PATENT DOCUMENTS

| | | |
|---|---|---|
| CN | 101301990 | 11/2008 |
| EP | 1183102 | 3/2002 |
| EP | 1246699 | 10/2002 |
| EP | 1286774 | 3/2003 |
| EP | 1289133 | 3/2003 |
| EP | 1366356 | 12/2003 |
| EP | 1377364 | 1/2004 |
| EP | 1409722 | 4/2004 |
| JP | 11 114467 | 4/1999 |
| JP | 11114467 A | 4/1999 |
| JP | 2008 104966 | 5/2008 |
| JP | 2008104966 A | 5/2008 |
| WO | WO 02/071051 | 9/2002 |
| WO | WO 03/055976 | 7/2003 |
| WO | WO 03055976 | 7/2003 |
| WO | WO 2004/076047 | 9/2004 |
| WO | WO 2004/076047 A1 | 9/2004 |
| WO | WO 2005/100953 | 10/2005 |
| WO | WO 2006/087496 | 8/2006 |
| WO | WO 2007/118224 | 10/2007 |
| WO | WO 2007/128045 | 11/2007 |
| WO | WO 2007/128046 | 11/2007 |
| WO | WO 2007/128046 A1 | 11/2007 |
| WO | WO 2007/132211 | 11/2007 |
| WO | WO 2007/132211 A1 | 11/2007 |
| WO | WO 2008/040008 | 4/2008 |
| WO | WO 2008/089174 A2 | 7/2008 |
| WO | WO 2009/073402 A2 | 6/2009 |
| WO | WO 2009/122340 | 10/2009 |
| WO | WO 2011/023949 | 3/2011 |
| WO | WO 2011/060369 | 5/2011 |
| WO | WO 2011/060369 A1 | 5/2011 |
| WO | WO 2012/099291 A1 | 7/2012 |
| WO | WO 2012/114076 | 8/2012 |
| WO | WO 2012/156755 | 11/2012 |

OTHER PUBLICATIONS

Wu et al. "Surface and bulk acoustic waves in two-dimensional phononic crystal consisting of materials with general anisotropy." Physical Review B (2004) 69 094301.*

UKIPO Search Report mailed Dec. 15, 2009 for Application No. GB0914762.0.

UKIPO Search Report mailed Jun. 30, 2011 for Application No. GB1103211.7.

UKIPO Search Report mailed Sep. 6, 2011 for Application No. GB1108462.1.

International Search Report mailed Sep. 2, 2011 for International Application No. PCT/GB2010/001600.

International Search Report mailed Jun. 1, 2012 for International Application No. PCT/GB2012/000192.

International Search Report mailed Jan. 11, 2011 for International Application No. PCT/US2010/56724.

Dogheche, E., V. Sadaune, X. Lansiaux, D. Remiens, and T. Gryba "Thick $LiNbO_3$ layers on diamond-coated silicon for surface acoustic wave filters," Applied Physics Letters, Aug. 12, 2002, vol. 81, No. 7; p. 1329-1331.

Wu, T. T., Z. G. Huang, and S. Y. Lui, "Surface acoustic wave band gaps in micro-machined air/silicon phononic structures-theoretical calculation and experiment," Zeitschrift Fur Kristallographie, 2005, 220(9-10); pp. 841-847.

Wu, T. T., L. C. Wu, and Z. G. Huang, "Frequency band-gap measurement of two-dimensional air/silicon phononic crystals using layered slanted finger interdigital transducers," Journal of Applied Physics, 2005 97(9); p. 7.

Kuo, C. H. and Z. Ye, "Sonic crystal lenses that obey the lensmaker's formula," Journal of Physics D: Applied Physics, 2004, 37(15); pp. 2155-2159.

Mohammadi, S., et al., "Complete phononic bandgaps and bandgap maps in two-dimensional silicon phononic crystal plates," Electronics Letters, 2007, 43(16); pp. 898-899.

Mohammadi, S., et al., "Evidence of large high frequency complete phononic band gaps in silicon phononic crystal plates," Applied Physics Letters, 2008, 92(22); pp. 221905-3.

(56) References Cited

OTHER PUBLICATIONS

Olsson III, R. H., et al., "Microfabricated VHF acoustic crystals and waveguides," Sensors and Actuators A, 2008, v145-146; pp. 87-93.
Vasseur, J. O., et al., "Absolute forbidden bands and waveguiding in two-dimensional phononic crystal plates," Physical Review B, 2008, 77(8); pp. 085415-15.
Renaudin, A., P. Tabouriert, V. Zhang, J. C. Camart and C. Druon, "SAW nanopump for handling droplets in view of biological applications," Sensors and Actuators B, 2006, 113; pp. 389-397.
Renaudin, A., et al., "Monitoring SAW-actuated microdroplets in view of biological applications," Sensors and Actuators B, 2009, 138(1); pp. 374-382.
Du, X. Y., et al., "Microfluidic pumps employing surface acoustic waves generated in ZnO thin films," Journal of Applied Physics, 2009, 105(2); p. 024508-7.
Frommelt, T., et al., "Flow Patterns and Transport in Rayleigh Surface Acoustic Wave Streaming: Combined Finite Element Method and Raytracing Numerics versus Experiments," IEEE Transactions on Ultrasonics, Ferroelectrics, and Frequency Control, 2008, 55(10); pp. 2298-2305.
Shi, J., et al. "Focusing microparticles in a microfluidic channel with standing surface acoustic waves (SSAW)," Lab on a Chip, 2008, 8(2); pp. 221-223.
Wu, T. T. & I. Chang, "Actuating and detecting of microdroplet using slanted finger interdigital transducers," Journal of Applied Physics, 2005, 98(2); p. 024903-7.
Tan, M. K., J. R. Friend, and L. Y. Yeo, "Microparticle collection and concentration via a miniature surface acoustic wave device," Lab on a Chip, 2007, 7(5); pp. 618-625.
Zhang, A., W. Liu, Z. Jiang, and J. Fei, "Rapid concentration of particle and bioparticle suspension based on surface acoustic wave," Appl. Acoust., 2009, 70; pp. 1137-1142.
Li, H., J. R. Friend and L. Y. Yeo, "Surface acoustic wave concentration of particle and bioparticle suspensions," Biomed. Microdevices, 2007, 9; pp. 647-656.
Shilton, R., M. Tan, L. Yeo, and J. Friend, "Particle concentration and mixing in microdrops driven by focused surface acoustic waves," J. Appl. Phys., 2008, 104; p. 014910-9.
Bennes, J., S. Alzuaga, F. Cherioux, S. Ballandras, P. Vairac, J.-F. Manceau and F. Bastien, "Detection and High-Precision Positioning of Liquid Droplets Using SAW Systems," IEEE Transactions on Ultrasonics Ferroelectrics, and Frequency Control, 2007, 54(10); pp. 2146-2151.
Sethu, P., M. Anahtar, L. L. Moldawer, R. G. Tompkins, and M. Toner, "Continuous Flow Microfluidic Device for Rapid Erythrocyte Lysis," Anal. Chem., 2004, 76; pp. 6247-6253.
Chen X., C. F. Cui and C. C. Liu, "On-line cell lysis and DNA extraction on a microfluidic biochip fabricated by microelectromechanical system technology," Electrophoresis, 2008, 29; pp. 1844-1851.
Baek, S., J. Min and J.-H. Park, "Wireless induction heating in a microfluidic device for cell lysis," Lab on a Chip, 2010, 10; pp. 909-917.
Lee, D. W. and Y.-H. Cho, "A continuous electrical cell lysis device using a low dc voltage for a cell transport and rupture," Sensors and Actuators B, 2007, 124; pp. 84-89.
Siegrist, J., R. Gorkin, M. Bastien, G. Stewart, R. Peytavi, H. Kido, M. Bergeron, and M. Madou, "Validation of a centrifugal microfluidic sample lysis and homogenization platform for nucleic acid extraction with clinical samples," Lab on a Chip, 2010, 10; pp. 363-371.
Dicarlo, D., K.-H. Jeong, and L. P. Lee, "Reagentless mechanical cell lysis by nanoscale barbs in microchannels for sample preparation," Lab on a Chip, 2003, 3; pp. 287-291.
Taylor, M. T., P. Belgrader, B. J. Furman, F. Pourahmadi, G. T. A. Kovacs, and M. A. Northrup, "Lysing Bacterial Spores by Sonication through a Flexible Interface in a Microfluidic System," Analytical Chemistry, 2001, 73; pp. 492-496.
Cheng, J., E. L. Sheldon, L. Wu, A. Uribe, L. O. Gerrue, J. Carrino, M. J. Heller, and J. P. O'Connell, "Preparation and hybridization analysis of DNA/RNA from *E. coli* on microfabricated biolelectronic chips," Nature Biotechnology, 1998, 16; pp. 541-546.
Yager, P., T. Edwards, E. Fu, K. Helton, K. Nelson, M. R. Tam, and B. H. Weigl, "Microfluidic diagnostic technologies for global public health," Nature, 2006, 442;pp. 412-418.
Borthwick, Kathryn A. J., Tracey E. Love, Martin B. McDonnell, and W. Terrence Coakley, "Improvement of Immunodetection of Bacterial Spore Antigen by Ultrasonic Cavitation," Anal. Chem., 2005, 77; pp. 7242-7245.
Qiu C., Z. Liu, J. Mei, and J. Shi, "Mode-selecting acoustic filter by using resonant tunneling of two-dimensional double phononic crystals," Appl. Phys. Lett., 2005, 87; pp. 104101-3.
Wu T. T., C. H. Hsu, and J. H. Sun, "Design of a highly magnified directional acoustic source based on the resonant cavity of two-dimensional phononic crystals," Appl. Phys. Lett., 2006, 89; pp. 171912-3.
Batchelor, G.K., "Note on a class of solutions of the Navier-Stokes equations representing steady rotationally-symmetric flow," Q. J. Mech. Appl. Math., 1951, 4; pp. 29-41.
Raghaven, R. V., J. R. Friend, and L. Y. Yeo, "Particle concentration via acoustically driven microcentrifugation: microPIV flow visualization and numerical modelling studies," Microfluid. Nanofluid., 2010, 8; pp. 73-84.
Hsu, J.-C. and T. T. Wu, "Efficient formulation for band-structure calculations of two dimensional phononic-crystal plates," Phys. Rev. B, 2006, 74; p. 144303-7.
Waters, L. C., S. C. Jacobson, N. Kroutchinina, J. Khandurina, R. S. Foote, and J. M. Ramsey, "Microchip Device for Cell Lysis, Multiplex PCR Amplification, and Electrophoretic Sizing," Anal. Chem., 1998, 70 (1); pp. 158-162.
Kondoh, J., N. Shimizu, Y. Matsui, and S. Shiokawa, "Liquid Heating Effects by SAW Streaming on the Piezoelectric Substrate," IEEE Transactions on Ultrasonics, Ferroelectrics, and Frequency Control, 2005, 52 (10); pp. 1881-1883.
Eschbach, E., J. P. Scharsack, U. John, and L. K. Medlin, "Improved Erythrocyte Lysis Assay in Microtitre Plates for Sensitive Detection and Efficient Measurement of Haemolytic Compounds from Icthyotoxic Algae," J. Appl. Toxicol., 2001, 21; pp. 513-519.
Wu, Tsung-Tsong, et al., "Utilization of phononic-crystal reflective gratings in a layered surface acoustic wave device," Applied Physics Letters, 2009, vol. 94, No. 10; p. 101913-3.
Sritharan, K., et al., "Acoustic mixing at low Reynold's numbers," Applied Physics Letters, 2006, vol. 88, No. 5; p. 054102-3.
Fu, Y. Q., et al., "Recent developments on ZnO films for acoustic wave based bio-sensing and microfluidic applications: a review," Sensors and Actuators B, 2010, 143; pp. 606-619.
Scheerschmidt, G., et al., "Resonance modes of magnetically generated surface waves in acoustic wave guide systems," Journal of Magnetism and Magnetic Materials, 2010, 322; pp. 1628-1630.
Yang, C., et al., "Solution-processed flexible ZnO transparent thin-film transistors with a polymer gate dielectric fabricated by microwave heating," Nanotechnology, 2009, vol. 20, No. 46; p. 465201-5.
Pál, E., et al., "Hybrid ZnO/polymer thin films prepared by RF magnetron sputtering," Colloid Polym. Sci., 2009, vol. 287, No. 4; pp. 481-485.
Du, X.Y., et al., "ZnO film for application in surface acoustic wave device," Journal of Physics: Conference Series, 2007, vol. 76; pp. 012035-6.
Djafari-Rouhani, B., et al., "Absolute band gaps and waveguiding in free standing and supported phononic crystal slabs," Photonics and Nanostructures—Fundamentals and Applications, 2008, 6; pp. 32-37.
Heron, S. R., et al., "Surface Acoustic Wave Nebulization of Peptides As a Microfluidic Interface for Mass Spectrometry," Anal. Chem., 2010, 82; pp. 3985-3989.
Ho, J., et al., "Paper-Based Microfluidic Surface Acoustic Wave Sample Delivery and Ionization Source for Rapid and Sensitive Ambient Mass Spectrometry," Anal. Chem., 2011, 83(9); pp. 3260-3266.
Kurosawa, M., et al., "Surface acoustic wave atomizer," Sensors and Actuators, 1995, vol. 50; pp. 69-74.

(56) References Cited

OTHER PUBLICATIONS

Kim, J.-W., et al., "A device for fabricating protein chips by using a surface acoustic wave atomizer and electrostatic deposition," Sensors and Actuators B, 2005, vol. 107, No. 2; pp. 535-545.
Great Britain Application No. GB 1108462.1, filed May 19, 2011, entitled "Sample Nebulization".
Allison, et al. (2008) AIAA Journal of Propulsion and Power 24:547-553, "Ultrasonic Propulsion".
Alvarez, et al., (2007) 16$^{th}$ Australasian Fluid Mechanics Conference (AFMC) 621-624, "Microaerosol and Nanoparticle Synthesis for Drug Delivery via Surface Acoustic Wave Atomization".
Alvarez, et al., (2008) Nanotechnology 19:455103, "Rapid generation of protein aerosols and nanoparticles via surface acoustic wave atomization".
Baek et al., (2010) Lab on a Chip 10:909-917, "Wireless induction heating in a microfluidic device for cell lysis".
Batchelor G. K. (1951) Q. J. Mech. Appl. Math 4:29-41, "Note on a class of solutions of the Navier-Stokes equations representing steady rotationally-symmetric flow".
Benchabane et al. (2005) Ultrasonics Symposium IEEE 2:922-925, "Silicon phononic crystal for surface acoustic waves".
Benchabane et al. (2006) Photonic Crystal Materials and Devices III 6182:18216, "Elastic band gaps for surface modes in an ultrasonic lithium niobate photonoic crystal".
Bennes et al. (2007) IEEE Transactions on Ultrasonics Ferroelectrics and Frequency Control 54(10):2146-2151, "Detection and high-precision positioning of liquid droplets using SAW Systems".
Beyssen et al.(2005) Ultrasonics Symposium IEEE 2:1028-1031, "Surface acoustic wave microfluidic device".
Borthwick et al., (2005) Anal. Chem. 77:7242-7245, "Improvement of Immunodetection of Bacterial Spore Antigen by Ultrasonic Cavitation".
Bourquin et al. (2011) Lab Chip 11:2725-2730, "Integrated immunoassay using tuneable surface acoustic waves and lensfree detection".
Bourquin et al. (2010) Lab on a Chip, "Tuneable surface acoustic waves for fluid and particle manipulations on disposable chips".
Bourquin et al. (2011) Adv Mater 23:1458-1462, "Phononic Crystals for Shaping Fluids".
Chen et al. (2008), *Electrophoresis* 29:1844-1851, "On-line cell lysis and DNA extraction on a microfluidic biochip fabricated by microelectromechanical system technology".
Cheng et al. (1998) Nature Biotechnology 16:541-546, "Preparation and hybridization analysis of DNA/RNA from *E. coli* on microfabricated bioelectronic chips".
Di Carlo et al. (2003) Lab on a Chip 3:287-291, "Reagentless mechanical cell lysis by nanoscale barbs in microchannels for sample preparation".
Djafari-Rouhani B et al. (2008) Photonics and Nanostructures—Fundamentals and Applications 6:32-37, "Absolute band gaps and waveguiding in free standing and supported phononic crystal slabs".
Dogheche et al. (2002) Applied Physics Letters vol. 81, No. 7 p. 81(7):1329, "Thick LiNbO3 layers on diamond-coated silicon for surface acoustic wave filters".
Du X. Y. et al.(2007) Journal of Physics: Conference Series, 76:012035, "ZnO film for application in surface acoustic wave device".
Du, X.Y. et al., (2009) Journal of Applied Physics 105(2):024508-7, "Microfluidic pumps employing surface acoustic waves generated in ZnO thin films".
Eckart C., (1948) Phys. Rev. 73:68-76, "Vorticies and Streams Caused by Sound Waves".
Ehlers K. M. & Koiller J. (2011) Math Comput Model 53:1489-1504, "Could cell membranes produce acoustic streaming? Making the case for Synechococcus self-propulsion".
Ehlers K. M., Samuel A. D., Berg H. C., & Montgomery R. (1996) Proc Natl Acad Sci 93:8340-8343, "Do cyanobacteria swim using traveling surface waves?".

Ennis W.J., Lee C., Plummer M., & Meneses P. (2011) Plast Reconstr Surg. 127(Suppl 1):93S, "Current status of the use of modalities in wound care: electrical stimulation and ultrasound therapy".
Eschbach et al. (2001) J. Appl. Toxicol 21:513-519, "Improved Erythrocyte Lysis Assay in Microtitre Plates for Sensitive Detection and Efficient Measurement of Haemolytic Compounds from Ichthyotoxic Algae".
Franke et al. (2010) Lab Chip 10:789-794, "Surface acoustic wave actuated cell sorting (SAWACS)".
Friend J. & Yeo L. (2011) Rev Mod Phys 83:647, "Microscale acoustofluidics: Microfluidics driven via acoustics and ultrasonics".
Frommelt, T. et al., (2008) IEEE Transactions on 55(10):2298-2305, "Flow patterns and transport in Rayleigh surface acoustic wavestreaming: combined finite element method and raytracing numerics versus experiments. Ultrasonics, Ferroelectrics and Frequency Control".
Fu et al., (2010) Sensors and Actuators B: Chemical 143:606-619, "Recent developments on ZnO films for acoustic wave bio-sensing and microfluidics applications: a review".
Guenneau S., Movchan A., Petursson G., Ramakrishna S.A. (2007) New J. Phys. 9:1-18, "Acoustic metamaterials for sound focusing and confinement".
Hall et al., (2007) IEEE transactions on ultrasonics, 54:569-575 "ferroelectrics, and frequency control".
Heron et al. (2010) Anal. Chem. 82:3985-3989, "Surface Acoustic Wave Nebulization of Peptides As a Microfluidic Interface for Mass Spectrometry".
Ho et al., (2011)Anal. Chem. 83(9):3260-6 "Paper-based microfluidic surface acoustic wave sample delivery and ionization source for rapid and sensitive ambient mass spectrometry".
Hodgson et al. (2009) Appl. Phys. Lett.94:024102-024103, "Transmitting high power of acoustic radiation via fluid couplants into superstrates for microfluidics".
Hongyu Yupp. and Eun Sok K., (2004) Micro-Electro Mechanical Systems, 17th IEEE International Conference on, p. 486-489, "Ultrasonic underwater thruster".
Hori K. M. T. & Ito K. (1997) International Journal of the Japan Society for Precision Engineering 31:1, "Development of ultra-small sized servo actuator with brushless DC motor, planetary gear drive and optical rotary encoder".
Hsu J. and Wu T., (2006) Phys Rev. B, 74, 144303, "Efficient formulation for band-structure calculations of two dimensional phononic-crystal plates".
Kim et al. (2005) Sensors and Actuators B 107(2):535-545, "A device for fabricating protein chips by using a surface acoustic wave atomizer and electrostatic deposition".
Kondoh et al. (2009) Sensors and Actuators A 149:292-297, "Development of temperature-control system for liquid droplet using surface acoustic wave devices".
Kondoh et al. (2005) IEEE transactions on ultrasonics, ferroelectrics, and frequency control 52(10), "Liquid Heating Effects by SAW Streaming on the Piezoelectric Substrate".
Kuo N. K., Zuo C., Piazza G. (2009) Joint Meeting of the European Frequency and Time Forum and the IEEE International Frequency Control Symposium 10-13, "Demonstration of inverse acoustic band gap structures in AlN and integration with piezoelectric contour mode wideband transducers".
Kuo, C.H. and Z. Ye, (2004) Journal of Physics D—Applied Physics 37(15):2155-2159, "Sonic crystal lenses that obey the lensmaker's formula".
Kurosawa et al. (1995) Sensors and Actuators 50(1-2):69-74, "Surface acoustic wave atomizer".
Kurosawa M., Takahashi M., & Higuchi T. (1996) IEEE Trans Ultrason Ferroelectr Freq Control 43: 901-906, "Ultrasonic linear motor using surface acoustic waves".
Laude V., Wilm M., Benchabane S., Khelif A. (2004) Ultrasonics Symposium, 2004 IEEE 2:1046-1049, "Full band gaps for surface acoustic waves in piezoelectric phononic crystals".
Laugharn et al., Methods and Apparatus for acoustically controlling liquid solutions in microfluidic devices WO01070381 (Covaris, Inc.) and family.

(56) References Cited

OTHER PUBLICATIONS

Lee D. W. & Cho Y.-H., (2007) Sensors and Actuators B 124:84-89, "A continuous electrical cell lysis device using a low dc voltage for a cell transport and rupture".
Li H. et al. (2007) Biomedical Microdevices, Kluwer Academic Publishers, BO 9(5):647-656, "Surface acoustic wave concentration of particle and bioparticle suspensions".
Lighthill J., (1978) J. Sound Vib., 61:391-418 "Acoustic streaming".
Mohammadi, S., et al., (2007) Electronics Letters, 43(16):898-899, "Complete phononic bandgaps and bandgap maps in twodimensional silicon phononic crystal plates".
Mohammadi, S., et al., (2008) Applied Physics Letters 92(22):3, "Evidence of large high frequency complete phononic band gaps in silicon phononic crystal plates".
Moroney et al. (1991), Appl. Phys. Lett., 59:774-776, "Microtransport induced by ultrasonic Lamb waves".
Morton et al. (2008) PNAS 105(21):7434-7438; doi:10.1073/pnas.0712398105.
Muller C et al. (2007) Zinc Oxide Materials and Devices II 6474:647413-647415, "Surface acoustic wave devices".
Neuzil P. et al, (2006) Mol. BioSyst. 2:292-298.
Nyborg W., (1965) Academic Press, New York, "Acoustic Streaming".
Olsson, R.H., et al., (2008) Sensors and Actuators a-Physical 145:87-93, "Microfabricated VHF acoustic crystals and waveguides".
Pál et al. (2009), Colloid and Polymer Science 287(4):481-485, "Hybrid ZnO/polymer thin films prepared by RF magnetron sputtering".
Pennec Y. et al. (2005) Appl. Phys. Lett. 87:261912-261913, "Acoustic channel drop tunneling in a phononic crystal".
Prada C., Clorennec D., Murray T. W., Royer D. (2009) J. Acoust. Soc. Am. 126:620-625, "Influence of the anisotropy on zerogroup velocity Lamb modes".
Qi et al. (2009), Lab on Chip 9:2184-2193, "Miniature inhalation therapy platform using surface acoustic wave microfluidic atomization".
Qiu C., Liu Z., Mei J., Shi J. (2005) Appl. Phys. Lett. 87:104101-104103, "Mode-selecting acoustic filter by using resonant tunnelling of two-dimensional double phononic crystals".
Raghaven R. V., Friend J. R., Yeo L. Y. (2010) Micorfluid. Nanofluid. 7:73-84, "Particle concentration via acoustically driven microcentrifugation: microPIV flow visualization and numerical modelling studies".
Renaudin A. et al., (2009) Sensors and Actuators B: Chemical, 138(1), 374-382, "Monitoring SAW-actuated microdroplets in view of biological Applications".
Renaudin et al. (2006) Sensors and Actuators B 113:389, "SAW nanopump for handling droplets in view of biological applications".
Sankaranarayanan et al. (2008) Phys. Rev. E Stat. Phys. Plasmas Fluids Relat. Interdiscip. Topics 77: 066308, "Flow induced by acoustic streaming on surface-acoustic-wave devices and its applications in biofouling removal: A computational study and comparisons to experiment".
Scheerschmidt, G., Kirk, K. J., McRobbie G., (2010) Journalism of Magnetism and Magnetic Materials 322:1628-1630, "Resonance modes of magnetically generated surface waves in acoustic wave guide systems".
Schneider et al. (2008) ChemPhysChem 9: 641-645, "An Acoustically Driven Microliter Flow Chamber on a Chip (µFCC) for Cell-Cell and Cell-Surface Interaction Studies".
Sethu et al. (2004) Anal. Chem. 76:6247-6253, "Continuous Flow Microfluidic Device for Rapid Erythrocyte Lysis".
Shi et al. (2009) Lab Chip 9:2890, "Acoustic tweezers: patterning cells and microparticles using standing surface acoustic waves (SSAW)".
Shi, J. et al., (2008) Lab on a Chip, 8(2), 221-223, "Focusing microparticles in a microfluidic channel with standing surface acoustic waves (SSAW)".
Shilton et al. (2008), J. Appl. Phys. 104:014910.
Shiokawa et al. (1989) Proc IEEE Ultrason. Symp. 641:643-646, "Liquid streaming and droplet formation caused by leaky Rayleigh waves".
Siegrist et al. (2010) Lab on a Chip 10:363-371, "Validation of a centrifugal microfluidic sample lysis and homogenization platform for nucleic acid extraction with clinical samples".
Sinclair M. J. (2000) Seventh Intersociety Conf. on Thermal and Thermomechanical Phenomena in Electronic Systemsl: 127-132, "A high force low area MEMS thermal actuator".
Smith et al. (1969) IEEE T. Microw. Theory 17:856-864.
Sritharan K. et al, (2006) Applied Physics Letters, AIP,American Institiute of Physics, Melville, NY, US, 88(5):54102-054102, "Acoustic mixing at low Retnold's numbers".
Strobl et al. (2004), IEEETrans. Ultrason, Ferroelect. Freq. Control 51:1432-1436.
Su Y-C L..L & Pisano A. P. (2002) J Microelectromech Syst 11: 736, "A water-powered osmotic microactuator".
Tai Y-C & Muller R. S. (1989) Sens Actuators 20:49-55, "IC-processed electrostatic synchronous micromotors".
Tan A. C. H. and Hoover F. S., (2010) IEEE Oceans p. 1-9, "Thrust and wake characterisation in small, robust ultrasonic thrusters".
Tan et al. (2009) Physical Review Letters 103:024501, "Interfacial Jetting Phenomena Induced by Focused Surface Vibrations".
Tan et al. (2007), Lab on a Chip, 7(5):618-625, "Microparticle collection and concentration via a miniature surface acoustic wave device".
Taylor et al. (2001) Analytical Chemistry 73:492-496, "Lysing Bacterial Spores by Sonication through a Flexible Interface in a Microfluidic System".
Überall H (1973) Phys. Acoustics: principles and methods 10:1-57, "Surface Waves in Acoustics".
Vasseur, J.O. et al., (2008) Physical Review B (Condensed Matter and Materials Physics), 77(8):085415-15, "Absolute forbidden bands and waveguiding in two-dimensional phononic crystal plates".
Waters et al. (1998) Anal. Chem. 70(1):158-162, "Microchip Device for Cell Lysis, Multiplex PCR Amplification, and Electrophoretic Sizing".
Watson B. et al. (2009) J Micromech Microeng 19: 022001, "Piezoelectric ultrasonic resonant motor with stator diameter less than 250 µm: the Proteus motor".
Watson B. et al., (2010) J. Micromech. Microeng. 20:115018, "Modelling and testing of a piezoelectric ultrasonic micro-motor suitable for in vivo micro-robotic applications".
Wilson et al. (2010) Anal. Chem.82:2119-2123.
Wilson I. G., (1997) Applied and Environmental Microbiology, 63(10):3741-3751, "Inhibition and Facilitation of Nucleic Acid Amplification".
Wixforth A, Gauer C, Scriba J, Wassermeier M, Kircher R (2003) Microfluidics, BioMEMS, and Medical Microsystems 4982:235-242, "Flat fluidics: a new route toward programmable biochips".
Wixforth A. (2006) Journal of the Association for Laboratory Automation 11:399-405, "Acoustically Driven Programmable Microfluidics for Biological and Chemical Applications".
Wixforth A., (2003) Superlattices and Microstructures 33:389-396, "Acoustically-driven planar microfluidics".
Wu T. T. et al, (2009) Applied Physics Letters, AIP, American Institiute of Physics, Melville, NY, US, 94(10):101913-101913, "Utilization of phononic-crystal reflective gratings in a layered surface acoustic wave device".
Wu T. T., Hsu C. H., Sun J. H. (2006) Appl. Phys. Lett. 89:171912-171913, "Design of a highly magnified directional acoustic source based on the resonant cavity of two-dimensional phononic crystals".
Wu, T. & Chang, I., (2005) Journal of Applied Physics, 98(2), 024903-7, "Actuating and detecting of microdroplet using slanted finger interdigital transducers".
Wu, T.T., L.C. Wu, and Z.G. Huang, (2005)Journal of Applied Physics, 97(9): 7, "Frequency band-gap measurement of two-dimensional air/silicon phononic crystals using layered slanted finger interdigital transducers".

(56) References Cited

OTHER PUBLICATIONS

Wu, T.T., Z.G. Huang, and S.Y. Liu, (2005) Zeitschrift Fur Kristallographie, 220(9-10): 841-847, "Surface acoustic wave band gaps in micro-machined air/silicon phononic structures—theoretical calculation and experiment".
Yager et al. (2006), Nature 442:412-418, "Microfluidic diagnostic technologies for global public health".
Yang et al., (2009) Nanotechnology 20(46):465201, "Solution-processed flexible ZnO transparent thin-film transistors with a polymergate dielectric fabricated by microwave heating."
Yatsuda H. and Yamanouchil K., (2000) IEEE Trans. Ultrason. Ferroelectr. Freq. Control, 47:140-147.
Yeo L. and Friend J. R., (2009) Biomicrofluidics, 3:012002, "Ultrafast microfluidics using surface acoustic waves".
Zhang et al. (2009) Applied Acoustics 70:1137-1142, "Rapid Concentration of Particle and Bioparticle Suspension Based on Surface Acoustic Wave".
International search report on PCT/GB2010/001600, dated Sep. 2, 2011.
International Search Report on PCT/GB2012/000192 dated Jun. 1, 2012.
International Search Report on PCT/GB2012/051133 dated Dec. 13, 2012.
UKIPO search report on GB 1103211.7 dated Jun. 30, 2011.
UKIPO search report on GB0914762.0, dated Dec. 15, 2009.
UKIPO Search Report on GB1108462.1 dated Sep. 6, 2011.
UKIPO search report on GB1221614.9 dated Mar. 7, 2013.
UKIPO search report on GB1315755.7 dated Feb. 26, 2014.
English translation of CN search report on 201080049008.X dated Aug. 26, 2013.
http://medicalphysicsweb.org/cws/article/research/26443—"Ultrasound that won't have you in stitches—MedicalPhysicsWeb.pdf".
http://www.arobella.com/products/qoustic-description.htm—"Description—Qoustic Wound Therapy System™—Arobella Medical, LLC—Sound .pdf".
http://www.celleration.com/mist-therapy/—"Mist Therapy << Celleration.pdf".
http://www.misonix.com/medical/products/sonicone/—"Misonix—SonicOne O. R..pdf".
http://www.technologyreview.com/biomedicine/17215/—"An Ultrasonic Tourniquet to Stop Battlefield Bleeding _MIT Technology Review.pdf".
Standard F756-08, Standard Practice for Assessment of Hemolytic Properties of Materials, ASTM, Mar. 2009.
Guttenberg, et al. (2005) Lab Chip 5:308-317, "Planar chip device for PCR and hybridization with surface acoustic wave pump".

\* cited by examiner

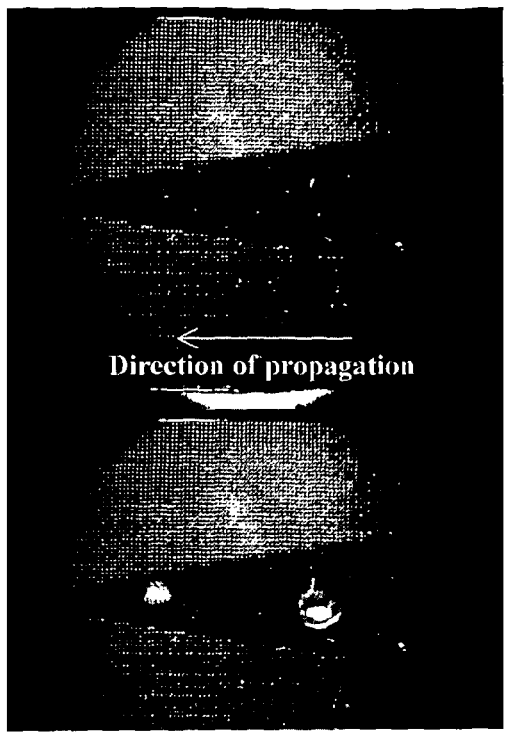
Fig. 10
Fig. 11
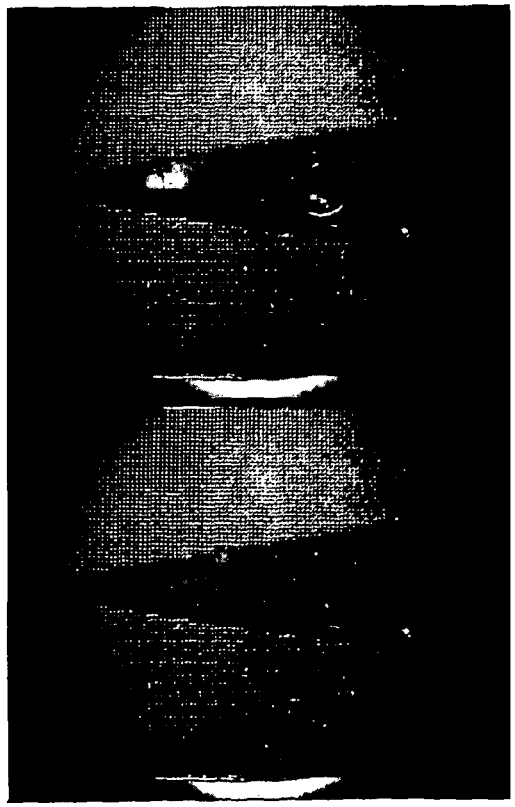
Fig. 12
Fig. 13

FLUIDICS APPARATUS AND FLUIDICS SUBSTRATE

RELATED APPLICATIONS

This application is a 35 U.S.C. §371 national phase application of PCT/GB2010/001600 (WO/2011/023949), filed on Aug. 24, 2010, entitled "Fluidics Apparatus and Fluidics Substrate", which application claims priority to Great Britain Application Serial No. 0914762.0, filed Aug. 24, 2009, which is incorporated herein by reference in its entirety.

BACKGROUND TO THE INVENTION

1. Field of the Invention

The present invention relates to fluidics apparatus and substrates for fluidics apparatus, and uses of such apparatus and substrates. Of particular, but not necessarily exclusive, interest is fluid sample manipulation in a microfluidics context. The invention has particular, but not exclusive, application to the manipulation of liquid droplets, for example in biological, biochemical, medical, veterinary and chemical assays, analysis, diagnosis, and synthesis and production of reagents and chemicals.

The present invention further relates to methods for lysing cells and to the use of a fluidics apparatus for lysing cells in a fluid sample.

2. Related Art

Microfluidics devices are well known for handling and analysing small volumes of fluids. For example, WO 2005/100953 discloses a system for measuring viscosity of fluids. Fluids are moved along microfluidic passageways using a thermal pump.

Alternative approaches to microfluidics liquid handling include the use of surface acoustic wave devices, as described in US 2007/0140041. In that document, there is disclosed the problem of mixing two microfluidics streams at a manifold, since at microfluidics dimensions, some liquids flow via laminar flow, and the lack of turbulence makes mixing difficult. Accordingly, US 2007/0140041 seeks to improve mixing between two fluid flows at a microfluidics manifold using surface acoustic waves (SAWs). A SAW transducer is located in contact with the manifold in order to promote mixing of the fluid streams at the manifold junction.

Surface acoustic waves (SAWs, the most common being Rayleigh waves) are acoustic waves that can be caused to travel along the surface of a material. Surface acoustic waves can be conveniently formed at the surface of a piezoelectric material by the application of a suitable electrical signal to an electrode arrangement at the surface of the piezoelectric material. A suitable electrode arrangement utilizes interdigitated electrodes, where a first electrode has an arrangement of parallel electrode fingers having a regular spacing between the fingers. A corresponding second electrode of similar shape has fingers which protrude into the gaps between the fingers of the first electrode. The combination of the electrode arrangement and the piezoelectric material forms a transducer.

SAW transducers are known particularly for use in frequency filters in telecommunications devices such as mobile telephones. In such a filter, there is an input transducer and an output transducer. The input signal is applied to the input transducer, to form a series of SAWs which propagate to the output transducer. At the output transducer, the SAWs are converted back into an electrical signal. For example, Dogheche et al [E. Dogheche, V. Sadaune, X. Lansiaux, D. Remiens, and T. Gryba "Thick $LiNbO_3$ layers on diamond-coated silicon for surface acoustic wave filters" Applied Physics Letters Vol. 81, No. 7 (12 Aug. 2002) p. 1329] disclose the fabrication of piezoelectric films for SAW filters. Typically, such filters are formed using known piezoelectric substrates such as quartz, $LiTaO_3$ or $LiNbO_3$. However, the formation of suitable interdigitated electrode patterns on the surface of such substrates by conventional photolithography whilst providing a filter operable up to suitable telecommunications frequencies is difficult. Accordingly, Dogheche et al formed thick (around 1 μm thick) piezoelectric $LiNbO_3$ layers on diamond-coated silicon and demonstrated their operation as SAW filters at 293 MHz.

It has also been noted that it is possible to provide quasi crystalline structures in order to manipulate SAWs. It has been shown to be possible to use a variety of phononic band-gap structures to affect an acoustic wavefront generated in a piezoelectric material. For example, Wu el at [Wu, T. T., Z. G. Huang, and S. Y. Liu, "Surface acoustic wave band gaps in micro-machined air/silicon phononic structures—theoretical calculation and experiment" Zeitschrift Fur Kristallographie, 2005. 220(9-10): p. 841-847] discuss their investigations of the phononic band gaps in structures formed by micromachining silicon with a square lattice arrangement of holes. The transducer was formed with interdigitated electrodes having parallel fingers. Furthermore, Wu et al [Wu, T. T., L. C. Wu, and Z. G. Huang, "Frequency band-gap measurement of two-dimensional air/silicon phononic crystals using layered slanted finger interdigital transducers" Journal of Applied Physics, 2005. 97(9): p. 7] disclose the results of investigations using a similar phononic crystal using electrodes with interdigitated non-parallel fingers in the form of a fan shape. Furthermore, in a purely theoretical paper, Kuo and Ye [Kuo, C. H. and Z. Ye, "Sonic crystal lenses that obey the lensmaker's formula" Journal of Physics D-Applied Physics, 2004. 37(15): p. 2155-2159] discuss the properties of structures that could be used to focus acoustic waves.

The term "phononic crystal" is used as an analogy to a "photonic crystal". In a photonic crystal, a periodic structure causes reflections due to scattering of incident light, thereby allowing interference between the reflected light and the incident light as it propagates through the "crystal" (which typically is formed of an arrangement of dielectric materials based on a regular array, such as a Bragg reflector), at one or more wavelengths and angles of incidence. This interference manifests itself as a prevention of propagation of the light through the crystal at a certain wavelength (or range of wavelengths) and direction. Thus, there is a "band gap" of frequencies at which light cannot propagate through the photonic crystal. A phononic crystal, by analogy, has a periodic arrangement of discontinuities or variations in the mechanical properties of the material or materials making up the phononic crystal. Such a phononic crystal can prevent acoustic or mechanical waves of specific wavelength from propagating through the crystal. Since SAWs can be formed at tightly defined frequencies, the effect of phononic crystals on the propagation of SAWs has been studied by several groups.

Mohammadi et al [Mohammadi, S., et al., "Complete phononic bandgaps and bandgap maps in two-dimensional silicon phononic crystal plates" Electronics Letters, 2007. 43(16): p. 898-899] disclose the formation of complete phononic band gap structures using a square array of holes or a hexagonal array of holes in a silicon plate. In a publication from the same group, Mohammadi et al [Mohammadi, S., et al., "Evidence of large high frequency complete phononic band gaps in silicon phononic crystal plates" Applied Physics Letters, 2008. 92(22): p. 3] discuss the formation of large complete phononic band gaps using a hexagonal array of holes through a silicon plate.

Olsson et al [Olsson, R. H., et al., "Microfabricated VHF acoustic crystals and waveguides" Sensors and Actuators a-Physical, 2008. 145: p. 87-93] disclose the formation of acoustic bandgaps in a structure formed by including periodic arrays of tungsten scatterers in a silica matrix. Waveguides for the acoustic waves are provided by removing selected scatterers along a desired path.

Vasseur et al [Vasseur, J. O. et al., 2008. Absolute forbidden bands and waveguiding in two-dimensional phononic crystal plates. Physical Review B (Condensed Matter and Materials Physics), 77(8), 085415-15] set out a study of phononic bandgaps in a two dimensional phononic crystal plate formed by arrays of cylinders of a first material in a plate of a second material.

US 2008/0211602 discloses an acoustic wave device with a piezoelectric layer with transducer electrodes formed over a substrate, there being an omnidirectional acoustic mirror formed between the piezoelectric layer and the substrate.

Other workers have used SAWs in the manipulation of liquids. For example, Renaudin et al [A. Renaudin, P. Tabourier, V. Zhang, J. C. Camart and C. Druon "SAW nanopump for handling droplets in view of biological applications" Sensors and Actuators B, 113, 2006, p. 389] report on the fabrication and development of a SAW device for microfluidics for biological applications. SAWs at about 20 MHz are generated by interdigitated electrode transducers laid on a $LiNbO_3$ piezoelectric substrate. Droplets are transported along the surface of the transducer where hydrophilic micro tracks are provided between hydrophobic areas. Furthermore, the same research group [Renaudin, A. et al., 2009. Monitoring SAW-actuated microdroplets in view of biological applications. Sensors and Actuators B: Chemical, 138(1), 374-382] set out a method for determining the position of the droplet using echo signals detected by interdigitated transducers.

Du et al [Du, X. Y. et al., 2009. Microfluidic pumps employing surface acoustic waves generated in ZnO thin films. Journal of Applied Physics, 105(2), 024508-7] propose using ZnO thin films on Si substrates to form surface acoustic wave operated microfluidic pumps.

Frommelt et al [Frommelt, T. et al., 2008. Flow patterns and transport in Rayleigh surface acoustic wave streaming: combined finite element method and raytracing numerics versus experiments. Ultrasonics, Ferroelectrics and Frequency Control, IEEE Transactions on, 55(10), 2298-2305] investigate the patterns of liquid flow and particle transport inside a droplet subjected to surface acoustic waves.

Shi et al [Shi, J. et al., 2008. Focusing microparticles in a microfluidic channel with standing surface acoustic waves (SSAW). Lab on a Chip, 8(2), 221-223] propose using opposed interdigitated transducers to form an aligned arrangement of beads moving along a channel.

Wu and Chang [Wu, T. & Chang, I., 2005. Actuating and detecting of microdroplet using slanted finger interdigital transducers. Journal of Applied Physics, 98(2), 024903-7] disclose the movement of droplets on a SAW substrate by control of the signal applied to interdigitated transducers having fingers arranged in a slanting configuration.

Tan et al [Tan, M. K., J. R. Friend, and L. Y. Yeo, "Microparticle collection and concentration via a miniature surface acoustic wave device" Lab on a Chip, 2007. 7(5): p. 618-625] disclose the use of SAWs to collect microparticles such as pollen particles in a droplet of water. A water droplet is conveyed along a SAW transducer via a fluidic track.

Concentration of microparticles in droplets by asymmetric application of surface acoustic waves has also been described. Techniques described for breaking the symmetry of a surface acoustic wave involve aligning a drop on the edge of a parallel electrode interdigital transducer [A. Zhang, W. Liu, Z. Jiang and J. Fei, *Appl. Acoust.*, 2009, 70, 1137-1142.], positioning a gel to partially absorb the surface acoustic wave reflection (so that only part of the drop lies in the transmission pathway) [H. Li, J. R. Friend and L. Y. Yeo, *Biomed. Microdev.*, 2007, 9, 647-656], or using a more complex IDT that focuses the surface acoustic wave [R Shilton, M. Tan and L. Yeo, and J. Friend, *J. Appl. Phys.*, 2008, 104, 014910] using circular transducers with a fixed frequency and excitation pathway.

Bennes et al [J. Bennes, S Alzuage, F. Chemoux, S. Ballandras, P. Vairac, J-F Manceau and F. Bastien, "Detection and high-precision positioning of liquid droplets using SAW systems" IEEE Transactions on Ultrasonics Ferroelectrics and Frequency Control, 2007, 54(10): p. 2146-2151] disclose droplet detection and positioning using SAWs. The SAW devices used are formed from lithium niobate substrates ($LiNbO_3$ cut (XY1)/128°). Bennes et al explain that the droplets are moved due to the refraction of incoming SAWs along the substrate surface at the air/liquid interface, producing a resultant force which can have a component directed along the substrate surface. The $LiNbO_3$ substrate is treated to make it hydrophobic—this increases the contact angle with an aqueous droplet and decreases the force required to move the droplet by interaction with SAWs.

WO 02071051 discloses acoustic ejection of biomolecular samples for mass spectrometry.

WO 2007/128045 discloses the use of a SAW transducer to atomize a liquid droplet from a substrate coupled to a piezoelectric transducer by a fluid coupling layer, thereby forming zeolite nanocrystals.

Fluidics systems may be useful in the analysis of biological samples, for example in point-of-care diagnostic applications and portable biosensors. However, biological samples present a particular challenge for sample manipulation and analysis in fluidics, particularly microfluidics. Preparation of biological samples is often complex, involving multiple steps. Notably, for a biological sample containing cells the molecule of interest may be an intracellular molecule, such that sample preparation requires a cell disruption step in order to render intracellular molecules accessible for analysis and applications such as immunodiagnostics and pathogen detection.

There are a variety of ways to disrupt cells in order to release intracellular molecules for analysis. Cells are enclosed by a lipid bilayer called the plasma membrane (also known as the cell membrane, or cytoplasmic membrane), which defines the boundaries of the cell. Cell disruption by rupture of the plasma membrane is termed cell lysis, and this can be achieved by a variety of chemical and physical methods.

A typical chemical lysis procedure involves numerous steps, including the addition of lytic agents (e.g. enzymes, detergents), washing (usually using centrifugation steps), and elution of the processed samples for further analysis. Physical lysis procedures include heating and mechanical methods such as agitation with small particles (e.g. glass beads) and sonication (or ultrasonication). Sonication typically involves transmitting mechanical energy, via an immersed probe that oscillates with high frequency, to a solution containing cells in suspension, and resultant cavitation (the creation and collapse of microscopic bubbles) ruptures cells in the sample.

Chemical cell lysis procedures have been integrated into microfluidic systems [P. Sethu, M. Anahtar, L. L. Moldawer, R. G. Tompkins, and M. Toner, Continuous Flow Microfluidic Device for Rapid Erythrocyte Lysis, *Anal. Chem.* 2004, 76, 6247-6253; X. Chen, D. F. Cui and C. C. Liu, On-line cell lysis and DNA extraction on a microfluidic biochip fabricated by microelectromechanical system technology, *Electrophoresis* 2008, 29, 1844-1851]. However, these methods require lytic agents, which may significantly dilute the molecule of interest and thereby compromise sensitivity of subsequent detection steps. These methods also require a cumbersome liquid-driving system to move the liquids around the chip, which is impractical for point-of-care applications. Removal of lytic and/or eluting agents may be required for downstream processing or analysis of the sample, for example because these agents inhibit reactions (e.g. PCR-based amplification of nucleic acids), or because they compromise the molecule of interest.

Techniques have been developed for chemical-free lysis of cells in samples on microfluidic platforms. These include heating [S. Baek, J. Min and J.-H. Park, Wireless induction heating in a microfluidic device for cell lysis, *Lab on a Chip*, 2010, 10, 909-917], applying an electric field [D. W. Lee, Y.-H. Cho, A continuous electrical cell lysis device using a low dc voltage for a cell transport and rupture, *Sensors and Actuators B*, 2007, 124, 84-89], or using mechanical forces to disrupt the cells by the combined action of magnetic fields [J. Siegrist, R. Gorkin, M. Bastien, G. Stewart, R. Peytavi, H. Kido, M. Bergeron and M. Madou, Validation of a centrifugal microfluidic sample lysis and homogenization platform for nucleic acid extraction with clinical samples, *Lab on a Chip*, 2010, 10, 363-371], by using filter structures [D. Di Carlo, K.-H. Jeong and L. P. Lee, Reagentless mechanical cell lysis by nanoscale barbs in microchannels for sample preparation, *Lab on a Chip*, 2003, 3, 287-291] or by ultrasonication [M. T. Taylor, P. Belgrader, B. J. Furman, F. Pourahmadi, G. T. A. Kovacs and M. A. Northrup, Lysing Bacterial Spores by Sonication through a Flexible Interface in a Microfluidic System, *Analytical Chemistry* 2001, 73, 492-496 and M. T. Taylor, Apparatus and method for rapid disruption of cells or viruses, WO03055976 (Cepheid, Inc.)].

However, heat, electric fields or cavitation may compromise molecules of interest. Electrical lysis may be integrated in a microfluidics chip with other functions [J. Cheng, E. L. Sheldon, L. Wu, A. Uribe, L. O. Gerrue, J. Carrino, M. J. Heller, J. P. O'Connell, Preparation and hybridization analysis of DNA/RNA from *E. coli* on microfabricated bioelectronic chips, *Nature Biotechnology*, 1998, 16, 541-546], but other physical lysis methods require the addition of external actuations into the system to move the fluids around the chip, in a similar fashion as chemical-based lysis platforms. This has been a particular difficulty hindering the development of fully integrated "sample-to-answer" solutions for molecular diagnostics [P. Yager, T. Edwards, E. Fu, K Helton, K. Nelson, M. R. Tam and B. H. Weigl, Microfluidic diagnostic technologies for global public health, *Nature*, 2006, 442, 412-418].

SUMMARY OF THE INVENTION

The present inventors have realised that it is possible to manipulate fluid samples using surface acoustic waves in combination with structures that affect the transmission, distribution and/or behaviour of the surface acoustic waves. This represents one general aspect of the present invention.

Accordingly, in a first preferred aspect, the present invention provides a fluidics apparatus for manipulation of at least one fluid sample, the apparatus including a substrate having a substrate surface with a sample manipulation zone for location of the fluid sample and a transducer arrangement arranged to provide surface acoustic waves at the substrate surface for manipulation of the fluid sample, wherein the substrate surface has an arrangement of surface acoustic wave scattering elements for affecting the transmission, distribution and/or behaviour of surface acoustic waves at the substrate surface.

In a second preferred aspect, the present invention provides a use of a fluidics apparatus to manipulate at least one fluid sample, the apparatus including a substrate having a substrate surface with a sample manipulation zone in which the fluid sample is located and further including a transducer arrangement providing surface acoustic waves at the substrate surface for manipulation of the fluid sample, wherein the substrate surface has an arrangement of surface acoustic wave scattering elements affecting the transmission, distribution and/or behaviour of surface acoustic waves at the substrate surface.

In a third preferred aspect, the present invention provides a fluidics substrate for manipulation of at least one fluid sample, the substrate being couplable with a transducer arrangement for providing surface acoustic waves at a surface of the substrate for manipulation of the fluid sample, wherein the substrate surface has a sample manipulation zone for location of the fluid sample, wherein the substrate surface further has an arrangement of surface acoustic wave scattering elements for affecting the transmission, distribution and/or behaviour of surface acoustic waves at the substrate surface.

Preferred or optional features of the invention will now be set out. These may be applied singly or in any combination with any aspect of the invention, unless the context demands otherwise.

It is considered by the inventors (without wishing to be limited by theory) that surface acoustic waves tend to at least partially refract into the fluid sample. This refraction is due to the fluid sample having, in general, a different speed of propagation for the SAWs compared with the substrate. This produces streaming in the fluid sample. Accordingly, this is considered to be the origin of sample movement under the influence of SAWs.

It is preferred that the fluid sample is in the form of a drop, e.g. a droplet such as a microfluidic droplet. However, other arrangements are possible for the fluid sample, e.g. a channel of fluid, or a fluid held in a chamber. In the following discussion, the term "droplet" is used, but as discussed above, it is intended that the invention is not necessarily limited to the manipulation of droplets.

The fluid may comprise a liquid. Furthermore, the fluid may comprise one or more particles. For example, the fluid may be a liquid containing solid (or substantially solid) particles. Of particular interest are fluids comprising a suspension of solid particles in a carrier liquid.

The volume of the fluid sample depends on the application of the apparatus. For example, the volume of the fluid sample may be at least 1 picoliter. More preferably, the volume of the fluid sample is at least 10 picoliter, at least 100 picoliter or at least 500 picoliter. Larger volumes are contemplated, e.g. at least 1 nanoliter, at least 10 nanoliter, at least 100 nanoliter or at least 500 nanoliter. Still larger volumes are possible in some applications, e.g. at least 1 microliter or at least 10 microliter. The preferred upper limit for the volume of the fluid sample is about 5 milliliter, more preferably about 1 milliliter, still more preferably about 0.1 milliliter.

Preferably, the surface acoustic wave scattering elements have an arrangement based on a periodic arrangement. The periodic arrangement may be a one dimensional arrangement or a two dimensional arrangement. A two dimensional arrangement is preferred. The periodic nature may be, for example, translational symmetry and/or rotational symmetry. The term "based on" is used here because it is considered that the arrangement need not be precisely periodic. Furthermore, the arrangement may be deliberately displaced from a true periodic arrangement in order to provide a specific effect on the surface acoustic waves. For example, the arrangement may be progressively displaced from a true periodic arrangement with distance from a certain starting point in the arrangement. Furthermore, the arrangement may include one or more areas or lines of defective periodicity in the periodic arrangement. In some cases, the periodicity can be varied amid a single crystal by use of gradients, over which the pitch and or the size of the elements is varied. This variation in periodicity can have applications in waveguiding or lenses (focusing the acoustic power).

Typically, the periodic arrangement is a two-dimensional pattern, in that the periodicity extends in two dimensions. Suitable periodic patterns include translationally symmetrical lattice patterns such as tetragonal, square, trigonal, hexagonal, etc. Other suitable periodic patterns include rotationally symmetrical patterns, e.g. having a rotational symmetry of less than 360 degrees.

The surface acoustic wave scattering elements may be arranged in a scattering zone at the substrate surface. The scattering zone may overlap with the sample manipulation zone. However, preferably the scattering zone does not overlap with the sample manipulation zone. It is possible for the scattering zone to be adjacent the sample manipulation zone, in order to affect the surface acoustic wave distribution in the sample manipulation zone. The scattering zone may be formed at one or more borders of the substrate surface. In this case, there may be one or more scattering elements located in the sample manipulation zone.

Preferably, the scattering zone provides in use a different transmission, distribution and/or behaviour of surface acoustic waves compared with the sample manipulation zone.

The arrangement of the surface acoustic wave scattering elements preferably provides, in effect, a phononic crystal structure that interacts with or affects the acoustic field, e.g. in the sample manipulation zone.

Preferably, the manipulation of the droplet includes movement of the droplet along the sample manipulation zone. The sample manipulation zone may define a track for droplet movement. Additionally or alternatively, the manipulation of the droplet includes atomisation of the droplet from the sample manipulation zone.

When two or more droplets are manipulated using the apparatus, it is possible for the droplets to have different characteristics, e.g. different composition, different temperature, different viscosity, different entrained species (e.g. biological material, particles, solute, etc.). In this case, the manipulation of the droplets may include mixing of the droplets. Mixing may be achieved by moving the droplets along corresponding tracks to a mixing zone, where the droplets meet and are mixed to form one or more mixed droplets. The mixed droplet may then be moved onwardly from the mixing zone along a further track.

The operation of the apparatus may allow splitting of a droplet into two or more daughter droplets. Each daughter droplet may be conveyed onwardly along respective tracks or along the same track.

The operation of the apparatus may furthermore allow concentration of a species in one or more droplets. This can be achieved, for example, by allowing the SAWs to interact with the droplet to heat the droplet, thereby accelerating the evaporation of solvent. Alternatively, the acoustic field may be controlled by an appropriate arrangement of scattering elements and suitable control of the driving signal to the transducers to drive the species preferentially towards one part of the droplet. For example, an acoustic cavity can be set up in order to provide a standing wave arrangement, which has been shown to provide particle concentration [Shi, J. et al., 2008. Focusing microparticles in a microfluidic channel with standing surface acoustic waves (SSAW). Lab on a Chip, 8(2), 221-223]. Heating without deliberately promoting evaporation is of interest in its own right, e.g. for PCR (polymerase chain reaction) applications for DNA or RNA.

The operation of the apparatus may also allow concentration of a species in one or more droplets by inducing streaming within the droplet, which streaming concentrates species at a location within the droplet. In the context of the present invention, this type of concentration may be referred to as "centrifugation" (even though it may not represent true centrifugation) since it produces a "pellet"-like deposit of species within the "supernatant" of the liquid droplet, and can separate particles in the fluid sample from the fluid phase. This concentration can be achieved by providing SAWs to the droplet to induce rotational streaming in the droplet, for example by providing SAWs to the droplet asymmetrically (i.e. such that the distribution of SAWs is asymmetric with respect to the centre of the droplet footprint). Preferably, the substrate surface includes an arrangement of surface acoustic wave scattering elements arranged to scatter surface acoustic waves provided at the substrate surface into a configuration for inducing rotational streaming in the droplet. The droplet may be positioned on the substrate surface at a position relative to the surface acoustic wave scattering elements such that surface acoustic waves are partially scattered by the scattering elements and the droplet receives SAWs distributed asymmetrically with respect to the centre of the droplet footprint.

The sample manipulation zone may include at least one droplet sensor. The droplet sensor may be operable to detect the presence of a droplet. One or more droplet sensors may be arranged sequentially in order to detect the presence of a droplet along a track. In this way, the apparatus may be operable to detect the movement of a droplet along a track. Droplet sensing can be carried out, for example, using echo location as discussed by Renaudin et al [Renaudin, A. et al., 2009. Monitoring SAW-actuated microdroplets in view of biological applications. Sensors and Actuators B: Chemical, 138(1), 374-382]. Alternatively, droplet sensing can be carried out using imaging means such as a camera.

The substrate may have more than one sample manipulation zone. A series of sample manipulation zones may be provided, in communication with each other, the droplet being transferred from one sample manipulation zone to the next. As an example, a first sample manipulation zone may provide droplet movement from a first location to a second location. A second sample manipulation zone may provide a mixing stage where the droplet, received from the first sample manipulation zone, is mixed (e.g. with another droplet or simply mixed to mix its own contents), and may provide onwards movement of the mixed droplet. A third sample manipulation zone may provide an atomisation stage where the mixed droplet, received from the second sample manipulation zone, is atomised. This atomisation stage may be for analysis of the droplet, e.g. using a mass spectrometer. In this case, suitable arrangements of scattering elements are provided for each zone, to affect the acoustic field in each zone in a suitable way to promote the required functionality of each zone.

It is possible for the transducer to be provided by any means which allows the formation of surface acoustic waves. For example, suitable arrangements of optical, electrical or electromagnetic means are contemplated. In one embodiment, a laser can be controlled to provide fast, localised heating of the substrate, resulting in the formation of corresponding mechanical waves.

Preferably, the transducer comprises a layer of piezoelectric material. For example, the layer of piezoelectric material may be a sheet (e.g. a self-supporting sheet) of piezoelectric material. The layer of piezoelectric material may be a single crystal, such as a single crystal wafer. A suitable material is $LiNbO_3$. A preferred orientation for the cut for this material is Y-cut rot. 128°. This has a higher electromechanical coupling coefficient than other orientations. Other ferroelectric materials may be used, e.g. PZT, $BaTiO_3$, $SbTiO_3$ or ZnO. Of these, ZnO is attractive because it easily integrated with silicon. The piezoelectric layer may be formed by any suitable fabrication technique. For example, the piezoelectric layer may be deposited by printing.

The transducer preferably further comprises at least one arrangement of electrodes. For example, the electrodes may be interdigitated. More preferably, the transducer comprises two or more arrangements of electrodes. These may be disposed in order to provide the specific manipulation desired for the microfluidics droplets, although the arrangement of scattering elements significantly affects the distribution of the acoustic field at the substrate surface. Suitable arrangements are discussed below. In some embodiments, it is preferred that the transducer is tunable, such that the lateral position of the SAWs emission train is movable. For example, the slanted interdigitated arrangement of electrodes suggested by Wu and Chang [Wu, T. & Chang, I., 2005. Actuating and detecting of microdroplet using slanted finger interdigital transducers. Journal of Applied Physics, 98(2), 024903-7] can be used for the transducer. Slanted interdigitated arrangements of electrodes suitable for use in the present invention are described in more detail below.

It is possible for the sample manipulation zone to be formed at a surface of the transducer, i.e. that the droplet is manipulated on the surface of the, e.g., piezoelectric chip. However, more preferably, the substrate is separable from the transducer, e.g. as a separate entity that is removably locatable at the transducer. For example, the substrate may be in the form of a sheet having a first major surface and a second major surface, preferably formed substantially parallel with each other. The first major surface may provide the sample manipulation zone and the border zone. The second major surface may provide a coupling surface, for coupling with the transducer in operation. Coupling may be achieved using a coupling medium, preferably a fluid or gel coupling medium. The coupling medium may be an aqueous coupling medium, e.g. water. Alternatively, the coupling medium may be an organic coupling medium, such as an oil-based coupling medium or glycerol. The coupling medium provides intimate contact between the substrate and the transducer and allows the efficient transfer of acoustic energy to the substrate from the transducer.

The advantage of providing the substrate as a separate entity from the transducer is very significant. Typical SAW transducers are complex to manufacture. For this reason, they are typically expensive. Suitable microfluidic manipulations to be carried out using the transducer may be of the type that will contaminate the transducer if carried out on the transducer surface. Such contamination may be difficult or impossible to remove. Alternatively, removal may not be cost-effective, or may damage the transducer. However, it is strongly preferred that the transducer can be re-used. Accordingly, it is preferred that the microfluidic droplet does not contact the transducer but instead contacts the substrate coupled to the transducer. The substrate itself may be disposable (e.g. disposed of after a single use). One or more suitable sample manipulation zones and one or more border zones may be formed in a substrate by various methods, such as microfabrication, embossing, moulding, spraying, lithographic techniques (e.g. photolithography), etc. The inventors have found, surprisingly, that coupling of SAWs to the substrate from the transducer can be efficient and the SAWs can be controlled at the substrate surface using the interaction between the sample manipulation zones and the scattering zones.

Preferably, the first surface of the substrate is substantially planar, excluding the scattering elements. The second surface of the substrate need not be planar, and in some circumstances may be formed with a topography that provides additional engineering of the SAWs. For example, the second surface may include curved, projecting or recessed regions in order to direct the SAWs.

Preferably, suitable droplets for manipulation using the present invention have a volume in the range 0.1-10 μL. More preferably, suitable droplets of volume 1-5 μL are used.

Preferably, where the droplet is to be moved along the sample manipulation zone, the sample manipulation zone is in the form of a track, defining the intended path for the droplet. The track may be straight, curved, bent, angled, forked, split or joined with another track. It is preferred that the scattering zone is immediately adjacent the track.

The track may be provided with a hydrophilic surface, typically bordered by one or more hydrophobic areas. In the case of an aqueous sample, this can assist with confining the droplet to the track.

In some embodiments, the dimensions of the track and the relative location of the arrangement of scattering elements causes the track to support only the fundamental mode of the surface acoustic waves at a particular wavelength. However, this would typically lead to the use of very small droplets, at least where the SAW wavelength is small (i.e. high frequency). Accordingly, in some preferred embodiments, the arrangement of scattering elements is further away from the track than would be required in order to support only the fundamental mode of the surface acoustic waves at a particular wavelength.

The surface acoustic wave scattering elements may be elements that provide an interface capable of significant scattering of surface acoustic waves. Preferably, at the interface, there is a sharp change in elastic modulus (e.g. Young's modulus) of the medium of the substrate. This can be achieved by forming each scattering element from a different material compared with the material of the substrate, the different material typically having a different density compared with the material of the substrate. For example, one or more of the scattering elements may be formed by a void at the substrate surface. The void may be gas-filled, e.g. air-filled. Alternatively, the void may be filled with a different solid or liquid material compared with the material of the remainder of the substrate. Filling the void with a contrasting (e.g. mechanically, structurally or functionally contrasting) solid material is desirable, because it allows the substrate to be formed with a smooth surface, therefore allowing the droplet to move across the arrangement of scattering elements if required. The contrast in mechanical properties between the substrate and the scattering elements may be changed in use, e.g. by the application of an external stimulus such as heat.

The scattering elements preferably intersect the surface of the substrate. This is preferred since they are for scattering surface acoustic waves, which are predominantly surface phenomena. However, the scattering elements may extend to a non-zero depth in the substrate. For example, they may extend at least 5% into the thickness of the substrate. They may extend further than this, e.g. at least 10%, at least 20% or more into the thickness of the substrate. In some circumstances, the scattering elements may extend through the entire thickness of the substrate, although a depth of about half of the thickness of the substrate is advantageous. The scattering elements may be pits in the substrate. Alternatively, the scattering elements may be pillars upstanding from the substrate surface.

Typically, the scattering elements are cylindrical (e.g. circular or oval cylindrical) in shape, or they may be prismatic or polygonal in shape. Alternatively, the scattering elements may be ridges or grooves in the substrate. Such shapes may have a straight form, but may alternatively have a curved or angled form.

Preferably, the substrate is in monolithic form. Thus, preferably, the scattering elements are formed in the substrate by addition or (more preferably) removal of substrate material from the substrate at the locations of the scattering elements. This may be done, for example, by embossing or etching, powder processing techniques (known in the field of metallurgy), machining (e.g. drilling). Alternatively, the scattering elements may be formed at the time of formation of the substrate, e.g. by moulding the substrate to the desired shape, including the scattering elements.

The scattering elements are placed with respect to the sample manipulation zone, and also with respect to the transducer, in order that there is a different transmission, distribution and/or behaviour of surface acoustic waves in the border region compared with the sample manipulation zone. For example, it is possible for the arrangement of scattering elements to be such that an incident surface acoustic wave having a predetermined wavelength at a predetermined angle of incidence, is transmitted through the border zone at a significantly lower amplitude than through the sample manipulation zone. At the limit of this effect, the incident surface acoustic wave may be substantially prevented from being transmitted through the border zone. In this case, the border zone acts as a phononic band gap structure to the incident SAWs. Furthermore, the effect of this is to concentrate the SAWs in the sample manipulation zone. This can provide very useful effects on the droplet in the sample manipulation zone.

The scattering elements may have an element-to-element nearest neighbour spacing of at least 10 μm. This is suitable for SAWs in the MHz region (e.g. of frequency of around 100 MHz). More preferably, this spacing is at least 20 μm, at least 40 μm, at least 60 μm, at least 80 μm, or at least 100 μm. This spacing may be at most 5 mm (corresponding to relatively low frequency SAWs), more preferably at most 4 mm, more preferably at most 3 mm, more preferably at most 2 mm, more preferably at most 1 mm, more preferably at most 0.9 mm, at most 0.8 mm, at most 0.7 mm, at most 0.6 mm. For example, an element-to-element nearest neighbour spacing in the range 200-500 μm has been shown to be suitable. For higher frequencies, e.g. in the GHz range, smaller spacings are contemplated, e.g. in the range down to at least 1 μm.

The scattering elements may provide various effects on the SAWs. In addition to the concentration effect mentioned above, the scattering elements may reflect (or partially reflect) the SAWs, and/or may diffract (or partially diffract) the SAWs, and/or may refract (or partially refract) the SAWs. Additionally or alternatively, there may be set up standing interference patterns of SAWs at the substrate surface.

Preferably, the apparatus includes a signal source for driving the transducer. The signal applied to the transducer affects the SAWs that are produced.

The transducer may have more than one set of electrodes, being independently controllable. In this case, the signal applied to each set of electrodes may be varied, in order to provide different manipulation of the droplet. For example, locating sets of electrodes so that SAWs are provided along different directions at the substrate surface may allow vector control of the movement of the droplet.

The substrate may be treated in order to provide it with a hydrophobic surface. For example, a contact angle between a water droplet and a flat region of the substrate surface may be not less than 65 degrees.

The present inventors have found that it is possible to lyse cells using surface acoustic waves. This represents another general aspect of the invention.

Accordingly, in a fourth preferred aspect, there is provided a method for lysing a cell, wherein the cell is comprised in a fluid sample contacting a substrate surface, the method comprising providing surface acoustic waves at the substrate surface, such that the cell lyses.

In a fifth preferred aspect, there is provided a use of a fluidics apparatus for lysing a cell in a fluid sample, wherein the fluidics apparatus includes a substrate having a substrate surface for contacting a fluid sample and a transducer arrangement arranged to provide surface acoustic waves at the substrate surface, and wherein said use comprises providing a surface acoustic wave at the substrate surface, such that a cell in a fluid sample contacting the substrate surface lyses.

Preferred or optional features of the fourth and fifth preferred aspects of the invention will now be set out. These may be applied singly or in any combination with any aspect of the invention, and/or with any preferred or optional feature of the first, second or third preferred aspects of the invention, as set out above, unless the context demands otherwise.

It is considered by the inventors (without wishing to be limited by theory) that surface acoustic waves tend to at least partially refract into the fluid sample. This refraction is due to the fluid sample having, in general, a different speed of propagation for the SAWs compared with the substrate. This produces streaming in the fluid sample. It is considered that applying SAWs to a substrate surface contacting a fluid sample can create a specific structure of pressure waves and shear stresses in the sample. These pressure waves and shear stresses can mechanically disrupt cells contained in the sample to effect cell lysis. It is considered that, in the preferred embodiments of the present invention, SAW-mediated cell lysis can achieve efficiencies above 95%, which is very favourable compared with known chemical and mechanical methods of cell lysis.

It is preferred that the fluid sample is a liquid sample containing cells. Furthermore, it is preferred that the fluid sample is an aqueous liquid sample containing cells. In a preferred embodiment, the fluid sample consists of or comprises blood, and therefore contains blood cells.

It is preferred that the fluid sample is in the form of a drop, e.g. a droplet such as a microfluidic droplet. However, other arrangements are possible for the fluid sample, e.g. a channel of fluid, or a fluid held in a chamber. In the following discussion, the term "droplet" is used, but as discussed above, it is intended that the invention is not necessarily limited to the lysis of cells in droplets.

The volume of the droplet may be at least 1 picoliter. For example the volume of the droplet may be at least 10 picoliter, at least 100 picoliter or at least 500 picoliter. The volume of the droplet may be higher, e.g. at least 1 nanoliter, at least 10 nanoliter, at least 100 nanoliter or at least 500 nanoliter. Preferably the droplet is larger, e.g. at least 1 microliter, at least 2 microliter, at 5 microliter, at least 10 microliter, at least 15 microliter, at least 20 microliter, at least 25 microliter or at least 50 microliter. The preferred upper limit for the volume of the droplet is about 5 milliliter, more preferably about 1 milliliter, still more preferably about 0.1 milliliter.

Preferably, suitable droplets for cell lysis using the present invention have a volume in the range 0.1-100 microliter, or 1-50 microliter. More preferably, suitable droplets of volume 5-25 microliter are used.

The volume of the droplet may be adjusted according to the area of contact between the droplet and the substrate surface. For example, the volume of the droplet may be adjusted to vary the contact angle (e.g. in the case where the droplet is confined to a particular fluid sample area—see below). Preferably, the contact angle (i.e. the included angle between the substrate surface and the tangent to the droplet surface at the substrate, measured in a plane containing the normal to the substrate surface) is not less than 65 degrees, not less than 75 degrees, not less than 85 degrees, or not less than 95 degrees. Preferably the contact angle is 65-115 degrees, or more preferably 95-115 degrees.

The substrate surface may be provided with a fluid sample area in the form of a fluid sample pinning zone. Preferably the fluid sample pinning zone is provided in the form of a spot, for pinning a fluid sample droplet to the substrate surface. Thus, the perimeter of the fluid sample pinning zone may delineate a fluid sample pinning line. Preferably, the fluid sample pinning zone is a hydrophilic area, for pinning an aqueous fluid sample to the substrate surface. More preferably, the fluid sample pinning zone is a hydrophilic area in the form of a spot, for pinning an aqueous droplet to the substrate surface. The hydrophilic area may be formed from e.g. lithium niobate (LiNbO$_3$), silicon (Si wafer), zinc oxide (ZnO), silicon oxide (SiO$_2$), glass, or plastics (polymers or copolymers, e.g. with a polyethylene glycol moiety, PEG). These may be further modified using a specific chemical process such as a silanisation (e.g. with aminopropyltriethoxysilane), poly-L-lysine, or PEG or a combination of processes. The hydrophilic area may be surrounded by a hydrophobic zone, which may be formed from e.g. silane such as 1H,1H,2H,2H-Perfluorooctyltriethoxysilane, octadecyltricholrosilane, or a Teflon-like coating (C4F8 deposition). The fluid sample pinning zone can also be formed by physical structures, for example the pinning zone may be formed as a well in the substrate surface. The pinning zone may be formed by a wall or walls that define the perimeter of the pinning zone, which wall or walls may be formed from pillars, or from scattering elements (i.e. elements that contribute to a phononic property of the substrate surface) for example pillars that act as scattering elements. The fluid sample pinning zone is not essential for cell lysis, but it may prevent the droplet from moving when surface acoustic waves hit it at high powers and may facilitate adjustment of the area of contact between the fluid sample and the substrate surface in order to vary the contact angle.

The fluid sample pinning zone preferably has a width or diameter of (or has a width or diameter in the range of up to) about 1 millimeter, about 2 millimeters, about 3 millimeters, about 4 millimeters, or about 5 millimeters.

The size (e.g. width, maximum allowed width, or diameter) and/or shape of the fluid sample pinning zone may be varied in order to vary the contact angle and surface tension properties at the fluid sample pinning line for a particular fluid sample volume, and thereby influence the propagation of the pressure wave from the incident SAW through the sample, such that a cell in the fluid sample is lysed.

The concentration of cells in the fluid sample may be adjusted in order to optimise cell lysis. Preferably the concentration is about 5 million cells/milliliter or less, about 3 million cells/milliliter or less, about 1 million cells/milliliter or less, about 500,000 cells/milliliter or less, or about 100,000 cells/milliliter or less.

The fluid sample may consist of or comprise a biological sample such as blood, saliva or urine. For example, the fluid sample may be whole blood. Preferably, the fluid sample is diluted blood, for example whole blood diluted in PBS. The dilution of the sample expressed as sample:diluent may be about 1:10 or greater (dilution factor 0.1 or lower), about 1:25 or greater (dilution factor 0.05 or lower), 1:50 or greater (dilution factor 0.02 or lower), or 1:100 or greater (dilution factor 0.01 or lower).

The present inventors have shown that the necessary conditions for cell lysis can be achieved using a variety of different SAW platforms and configurations. The present invention thus provides multiple routes to integrate preparation of biological samples in a complete assay on a microchip.

Without wishing to be bound by theory, the present inventors believe that, e.g. by focussing the acoustic power of SAWs at a position within a fluid sample containing cells, it is possible to create acoustic pressure fields and streaming within the sample that lyse the cells.

Preferably, surface acoustic waves are provided to the substrate surface contacting a droplet such that rotational streaming is induced in the fluid sample droplet. Without wishing to be bound by theory, the present inventors believe that rotational streaming results in the creation of one or more vortexes in the sample, and, under appropriate conditions, the pressures and shear stresses near the centre of a vortex are sufficient to lyse cells.

Rotational streaming may be induced in the droplet by providing the SAWs to the droplet in an asymmetrical manner in relation to the droplet, that is, providing the SAWs such that it hits the droplet asymmetrically. By causing an asymmetry in the SAWs with respect to the droplet, angular momentum and hence rotation is induced in the droplet. The term "asymmetrical" here refers to the distribution of the SAWs with respect to the droplet. One example of a suitable asymmetric distribution is provided where the SAW path incompletely overlaps with the footprint of the droplet on the substrate surface, as described below.

The term SAW "beam" is used herein to define the emission train, or path, of surface acoustic waves provided at a substrate surface. The terms SAW beam, SAW emission train and SAW path are used herein interchangeably. The width of the SAW beam is notionally defined by the aperture of the transducer that emits the SAW beam. The aperture of a transducer is the part of the transducer that resonates to emit a SAW beam. In the context of the present invention, the lateral width of an aperture of a transducer is taken to define the lateral width of the SAW beam. For a parallel electrode interdigitated transducer, the aperture is typically the lateral expanse of the region of overlap between the electrode fingers (see w, FIG. 6). In this context, the edge of the SAW beam is laterally aligned with the edge of the IDT aperture along the direction of propagation of the SAWS. Whilst it is understood that in reality the edge of a SAW beam is not necessarily sharp, as explained below, for the purposes of the present invention, an edge of a SAW beam is defined as a notional longitudinal edge in lateral alignment with an edge of a transducer aperture. It is understood that the amplitude of the SAWs decreases with lateral distance from the edge of the SAW beam.

For a droplet contacting a substrate surface to form a droplet footprint on the substrate surface, rotational streaming may be induced in the droplet by providing a surface acoustic wave at the substrate surface such that the surface acoustic wave path only partially overlaps with the droplet footprint (at least in terms of the position of the notional edge of the SAW path with respect to the droplet). A droplet may have an approximately circular footprint, for example, and the surface acoustic wave path may overlap with a segment of the footprint. A surface acoustic wave path may overlap with about 10-90% of the droplet footprint. A surface acoustic wave may be provided at the substrate surface such that the surface acoustic wave path overlaps with about 50% of the droplet footprint, wherein the edge of the surface acoustic wave path passes near the centre of the droplet.

In a first preferred embodiment of the fourth and fifth aspects of the present invention, a surface acoustic wave is provided at the substrate surface by a transducer arrangement (e.g. a parallel electrode interdigital transducer) and the droplet is positioned on the substrate surface at a position relative to the transducer arrangement such that the droplet receives SAWs distributed asymmetrically with respect to the centre of the droplet. For example, the droplet may be longitudinally displaced from but laterally aligned with respect to an edge of an aperture of an interdigital transducer (IDT) arrangement, wherein said edge of the aperture defines an edge of a SAWs emission train, such that the droplet is only partly located on the SAWs emission train provided by the IDT arrangement.

In a second preferred embodiment of the fourth and fifth aspects of the present invention, a surface acoustic wave is provided at the substrate surface by a transducer arrangement for which it is possible to control the lateral position of the SAWs emission train with respect to the transducer arrangement, for example by tuning the input frequency. In this embodiment, the droplet is placed on the substrate surface and the lateral position of the SAWs emission train is tuned to a position on the substrate surface such that the droplet receives SAWs distributed asymmetrically with respect to the centre of the droplet. The transducer arrangement may be a slanted IDT (also known as a slanted finger IDT) for which the lateral position of the SAWs emission train can be adjusted by varying the input frequency. An advantage of this embodiment is that it does not require precise positioning of the droplet on the substrate surface, since the lateral position of the SAWs emission train on the substrate surface can be adjusted relative to that of the droplet. In the case of a slanted IDT, it is more difficult to define a notional edge of the SAWs emission train, since the amplitude of the SAWs across the emission train may decrease relatively gradually laterally from a central maximum of the emission train. In this case, the notional edge of the SAWs emission train can be considered to be the lateral position at full width half maximum of the SAWs amplitude distribution in the lateral direction.

In a third preferred embodiment of the fourth and fifth aspects of the present invention, the substrate surface includes an arrangement of surface acoustic wave scattering elements arranged to scatter surface acoustic waves provided at the substrate surface into a configuration for inducing rotational streaming in the fluid sample. The scattering elements may affect the transmission, distribution or behaviour of surface acoustic waves at the substrate surface. In this embodiment, the droplet may be positioned on the substrate surface at a position relative to the surface acoustic wave scattering elements such that surface acoustic waves are partially scattered by the scattering elements and the droplet receives SAWs distributed asymmetrically with respect to the centre of the droplet.

It is not necessarily essential that the surface acoustic wave induces rotational streaming in order for cell lysis to be achieved. The pressure fields necessary for cell lysis may be induced using a wide range of surface acoustic wave geometries, encompassing standing waves as well. The inventors believe that it is possible to use surface acoustic waves to lyse cells within a droplet, without necessarily creating rotational streaming or a vortex within the droplet, by focusing acoustic power at a position within the droplet.

Furthermore, it is not necessarily essential that the surface acoustic wave is provided to the droplet asymmetrically in order for rotational streaming to be achieved. Cell lysis can be achieved when multiple vortexes are formed in configurations where the SAW hits the droplet in a more symmetrical manner. For example, it is possible to design a fluidics apparatus to achieve reproducible multiple vortexes in fluid sample droplets, for example by including arrangements of scattering elements or phononic structures (also known as phononic lattices or phononic crystals) on the substrate surface.

In accordance with the present invention, the substrate may be provided with a transducer arrangement.

It is possible for the transducer to be provided by any means which allows the formation of surface acoustic waves. For example, suitable arrangements of optical, electrical or electromagnetic means are contemplated. In one embodiment, a laser can be controlled to provide fast, localised heating of the substrate, resulting in the formation of corresponding mechanical waves.

Preferably, the transducer comprises a layer of piezoelectric material. For example, the layer of piezoelectric material may be a sheet (e.g. a self-supporting sheet) of piezoelectric material. The layer of piezoelectric material may be a single crystal, such as a single crystal wafer. A suitable material is $LiNbO_3$. A preferred orientation for the cut for this material is Y-cut rot. 128°. This has a higher electromechanical coupling coefficient than other orientations. Other ferroelectric materials may be used, e.g. PZT, $BaTiO_3$, $SbTiO_3$ or ZnO. Of these, ZnO is attractive because it easily integrated with silicon. The piezoelectric layer may be formed by any suitable fabrication technique. For example, the piezoelectric layer may be deposited by printing.

The transducer preferably further comprises at least one arrangement of electrodes. For example, the electrodes may be interdigitated. The transducer may comprise two or more arrangements of electrodes. These may be disposed in order to provide specific manipulation desired of microfluidic droplets. Suitable arrangements are discussed below. Preferably the transducer is tunable, such that the lateral position of the SAWs emission train is movable. In certain preferred embodiments, the arrangement of electrodes is the slanted interdigitated arrangement of electrodes suggested by Wu and Chang [Wu, T. & Chang, I., 2005. Actuating and detecting of microdroplet using slanted finger interdigital transducers. Journal of Applied Physics, 98(2), 024903-7]. Slanted interdigitated arrangements of electrodes for use in the present invention are described in more detail below.

It is possible for the substrate surface to be formed at a surface of the transducer, i.e. the droplet is manipulated on the surface of the, e.g., piezoelectric chip. However, more preferably, the substrate is separable from the transducer, e.g. as a separate entity that is removably locatable at the transducer. For example, the substrate may be in the form of a sheet having a first major surface and a second major surface, preferably formed substantially parallel with each other. The first major surface may provide a substrate surface for contacting the fluid sample. The second major surface may provide a coupling surface, for coupling with the transducer in operation. Coupling may be achieved using a coupling medium, preferably a fluid or gel coupling medium. The coupling medium may be an aqueous coupling medium, e.g.

water. Alternatively, the coupling medium may be an organic coupling medium, such as an oil-based coupling medium or glycerol. The coupling medium provides intimate contact between the substrate and the transducer and allows the efficient transfer of acoustic energy to the substrate from the transducer.

The advantage of providing the substrate as a separate entity from the transducer is very significant. Typical SAW transducers are complex to manufacture. For this reason, they are typically expensive. Suitable microfluidic manipulations to be carried out using the transducer may be of the type that will contaminate the transducer if carried out on the transducer surface. Such contamination may be difficult or impossible to remove. Alternatively, removal may not be cost-effective, or may damage the transducer. However, it is strongly preferred that the transducer can be re-used. Accordingly, it is preferred that the microfluidic droplet does not contact the transducer but instead contacts the substrate coupled to the transducer. The substrate itself may be disposable (e.g. disposed of after a single use). The inventors have found, surprisingly, that coupling of SAWs to the substrate from the transducer can be efficient and the SAWs can be controlled at the substrate surface, for example using scattering elements (e.g. phononic crystals, also known as phononic lattices) or by using a tunable electrode arrangement (e.g. slanted finger IDT).

Disposable substrates are especially useful for the analysis of biological samples. Disposable substrates may reduce sample cross contamination in point-of-care diagnostic applications, and may reduce contamination of samples with species that may compromise the molecule of interest (e.g. RNAse, where messenger RNA is the molecule of interest).

For the purposes of the present invention, the input power of the surface acoustic wave may be between −19 dBm and 0 dBM, between around −14 dBm and around −6 dBmb around −14 dBm or higher, around −12 dBm or higher, around −10 dBm or higher, around −9 dBm or higher, around −8 dBm, around −7 dBm, or around −6 dBm or higher.

For the devices described herein in relation to embodiments of the present invention, the related power arriving at the IDT can be obtained using the table below. The power arriving at the IDT is calculated by converting the input power value, expressed in dBM, to a value expressed in W and multiplying the W value by 5000 (the amplification by the amplifier).

| dBm | W |
| --- | --- |
| 0 | 5 |
| −1 | 3.971641 |
| −2 | 3.154787 |
| −3 | 2.505936 |
| −4 | 1.990536 |
| −5 | 1.581139 |
| −6 | 1.255943 |
| −7 | 0.997631 |
| −8 | 0.792447 |
| −9 | 0.629463 |
| −10 | 0.5 |
| −11 | 0.397164 |
| −12 | 0.315479 |
| −13 | 0.250594 |
| −14 | 0.199054 |
| −15 | 0.158114 |
| −16 | 0.125594 |
| −17 | 0.099763 |
| −18 | 0.079245 |
| −19 | 0.062946 |

The present inventors found that for a particular cell type at a particular concentration, if a relatively low power is used then cells are concentrated in the centre of the droplet without lysing, and if a relatively high power is used then cell lysis is achieved. Without wishing to be bound by theory, the present inventors believe that such an increase in power increases the pressures and shear stresses in the droplet such that cells in the droplet are crushed and lyse. Accordingly, a method of lysing cells according to the present invention may comprise providing SAWs to a droplet containing cells, and progressively increasing the input power, and thereby progressively increasing the power of the SAWs, until cell lysis is achieved. This way, for a given set of conditions, cells can be lysed using the minimum power necessary to achieve cell lysis under those conditions. For example, cells of a particular type can be lysed using the minimum power necessary to achieve cell lysis for that cell type.

The frequency of the surface acoustic wave may be in the range of about 10 kHz to about 1 GHz, preferably about 1 MHz to about 100 MHz, more preferably about 5 MHz to about 50 MHz, more preferably about 5 MHz to about 20 MHz, more preferably about 15 MHz to about 5 MHz, more preferably between about 13 MHz and about 9 MHz. The frequency of the surface acoustic wave may be about 12 MHz, about 11 MHz, about 10 MHz, or about 9 MHz.

For the purposes of the present invention, the SAW may be provided at the substrate surface for about 0.1 seconds or longer. The SAW may be provided for about 0.1-60 seconds. Preferably, the SAW is provided for about 1 second or less, about 2 seconds or less, or about 3, 4, 5, 6, 7, 8, 9, 10, 15, 20, 25, 30, or 35 seconds or less.

The present inventors found that cell lysis efficiency is affected by several factors, including the surface tension of the droplet, the contact angle of the droplet on the substrate surface, the concentration of cells in the droplet, power of the SAW and the amount of time for which the SAW is provided to the droplet. The optimum combination of values for each factor may depend on cell type. The skilled person, by adjusting these variables in combination or in isolation, based on the teaching provided herein, is able to provide conditions in which cell lysis can be achieved.

The term cell is used herein to refer to any type of cell, including eukaryotic and prokaryotic cells. In the context of the present invention, a cell is preferably a eukaryotic cell. A cell may be an animal cell, for example a mammalian cell (e.g. a blood cell, such as an erythrocyte). A cell may be that of a unicellular organism, (e.g. a trypanosome), which may be a protozoan or a protist. In some embodiments, the cell is a cell of a pathogen, for example a pathogenic protozoan, protist, or bacterium. A cell may have a cell wall, or may be wall-less (i.e. without a cell wall).

A fluid sample may contain a mixture of cells or cell types. The present inventors have found that the minimum power sufficient to lyse cells may vary depending on cell type. For example, under particular conditions (e.g. cell concentration, droplet contact angle) a specific power may sufficient to lyse cells of a first type, but insufficient to lyse cells of a second type. Under such conditions, if a SAW of that specific power is applied to a droplet containing a mixture of cells of the first and second type, cell lysis will be achieved for the cells of the first type but not cells of the second type. Accordingly, SAWs may be applied to a fluid sample containing a mixture of cell types in order to differentially lyse cells of different types. Different cell "type" may mean different taxonomic groups, for example different domains (eukaryotic cell type is different to prokaryotic cell type), kingdoms (e.g. animal cell type is different from fungal cell type), different physical or physiological types (e.g. a leukocyte is a different cell type from an erythrocyte). In particular, different cell types are cells that are differentially lysable (e.g. a first cell type is more easily lysed than a second cell type, that is, under a given set of experimental conditions, the lowest power necessary to achieve cell lysis for the first cell type is lower than the lowest power necessary to achieve cell lysis for the second cell type).

The term cell lysis is used herein to refer to any type of cell disruption. In particular, cell lysis is used to refer to cell disruption that results in release of intracellular molecules to the extracellular milieu, for example by rupture of the plasma membrane. Cell lysis encompasses rupture of the plasma membrane, and may encompass rupture of intracellular compartment (e.g. organelle) membranes such as the nuclear envelope and mitochondrial outer and inner membranes. Cell lysis is typically a complete and irreversible rupture of the plasma membrane, resulting in cell death. In the context of the present invention, however, cell lysis may encompass cell membrane poration, where the plasma membrane is incompletely ruptured (i.e. the plasma membrane temporarily and reversibly ruptures). Such poration may improve certain assays such as ELISA, in a similar way to that described in Borthwick et al [Kathryn A. J. Borthwick, Tracey E. Love, Martin B. McDonnell and W. Terence Coakley, Improvement of Immunodetection of Bacterial Spore Antigen by Ultrasonic Cavitation, Anal. Chem. 2005, 77, 7242-7245].

The term intracellular molecule, or intracellular molecule of interest includes macromolecules (protein, DNA, lipid, polysaccharide) small molecules (e.g. ATP, ADP. cAMP, glutathione, amino acids, oligosaccharides, monosaccharides) including metabolites and signalling molecules. The term intracellular molecule encompasses any molecule having an intracellular moiety of interest (e.g. a transmembrane protein). A molecule of interest is compromised if the structure of the molecule becomes significantly different from its native structure or intracellular structure, for example such that the molecule less amenable to analysis (e.g. an epitope required for immunological analysis is no longer present or has become immunologically inaccessible). The term "compromised" as used herein encompasses denaturation (e.g of a protein of interest) and degradation (e.g. hydrolysis of a polynucleotide, polypeptide or polysaccharide of interest).

Further optional features of the invention are set out below.

BRIEF DESCRIPTION OF THE DRAWINGS

FIG. 4 shows a droplet on a plain silicon surface without a border zone.

FIG. 5 shows a droplet on a substrate according to an embodiment of the invention.

FIGS. 10-13 show a series of consecutive frames from micrographic video footage of an embodiment of the device operating. These images clearly show that acoustic energy is being focused and reflected.

In FIGS. 27 and 28, the droplet is shown as located on a substrate that is separable from the transducer arrangement.

DETAILED DESCRIPTION OF THE PREFERRED EMBODIMENTS, FURTHER OPTIONAL FEATURES

Figure 1:
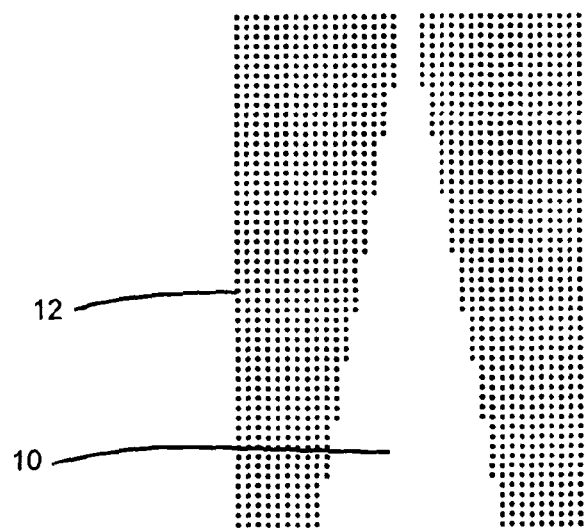
FIG. 1 shows a schematic plan view of a substrate for use with the present invention, showing a "funnel" type sample manipulation zone.

Preferred embodiments of the present invention will now be described by way of example.

It is known that microfluidic technologies can enable the precise control of the delivery of reagents, drugs and metabolites to single cells or to groups of cells. Such methods for can be used for new medicines discovery, or to deliver reagents and samples in diagnostic technologies.

Despite such rapid advances in microfluidic, or so-called "Lab-on-a-Chip" technologies over the last decade, there have, however, been few new methods that have been developed to generate fluid flow within micro-scale channels. Most existing methods to create such flow rely on generating a pressure difference to drive the flow (in particular by the use of various forms of mechanical pumps). These methods all rely upon external interconnects from the chip to the pump, often making the process of connection one of the most challenging.

Other alternative methods currently in use involve the use of a phenomenon known as electrokinetic pumping (including electro-osmosis or dielectrophoresis) to drive the fluid under electrical control. In all cases, however, these techniques require the implementation of metallic planar transducers within the microchannels. Whilst these electrical connections to the chip result in fluid flow, the whole chip, including the transducers, is disposed of at the end of each assay. Thus, neither pressure driven mechanical pumping, nor electrokinetics, afford the user with the ability to interrogate and move the fluid in a "non-contact" manner, at low cost.

The present inventors have developed new techniques for droplet manipulation in the microfluidic regime. These techniques are based upon the use of surface acoustic waves (SAWs) generated on a piezoelectric device, such as a device based on lithium niobate, $LiNbO_3$.

A Raleigh wave is a coupled compressional-shear system where the longitudinal and the transverse motion are out of phase by 90°. The present inventors have demonstrated that it is possible to propagate such longitudinal Raleigh waves (an example of SAWs) from the piezoelectric device, through a coupling medium (which can, for example be water or an oil) into a thin disposable microfluidic chip substrate formed of plastic, glass or other suitable material. Surprisingly, the waves carry sufficient energy to subsequently drive the fluids on the disposable substrate. Although the $LiNbO_3$ piezoelectric device is, itself, relatively expensive, in this format it is a re-usable platform, and it is only the substrate that is disposed of after a (typically single) use. The only physical contact for actuation of the droplet is through the medium between the $LiNbO_3$ and the disposable chip.

When Raleigh waves are propagated from a piezoelectric device to a substrate (e.g. a thin chip) coupled to the surface of the piezoelectric device, the resultant acoustic waves in the substrate may be described as Lamb waves. Raleigh waves and Lamb waves are types of surface acoustic waves. The term surface acoustic wave (SAW) is used herein to describe both Raleigh waves and Lamb waves unless indicated otherwise.

The functionality of the platform can, however, also be readily extended beyond simple pumping of fluids or droplets. For example, by microfabricating multiple SAW transducers on the piezoelectric device, and through the subsequent differential actuation of these transducers, it is possible to manipulate droplets in a variety of different directions (linear, orthogonal or at any angle between). If necessary, by combining different relative components of wave generation from orthogonal actuators, it is possible to enable splitting and recombination of droplets.

Surface acoustic waves are longitudinal in nature, such that a component of the energy is dissipated in the z-plane (containing the coupling medium). This is in contrast with shear waves parallel to the plane of propagation, where no significant energy would be dissipated normal to the surface. As this longitudinal wave propagates within the coupling medium, it is subject to reflections off the lower (basal) plane of the disposable microfluidic substrate. Thus, by micromachining well defined structures within this plane (using established surface microengineering techniques including photolithography, pattern-transfer, mask definition and etching), it is possible to engineer complex energy distributions in the disposable substrate. Indeed, by focussing the energies of the acoustic waves within the chip, it is possible to lyse cells on-chip, or to atomise samples such that they can be transported off-chip. One particular application is the creation of plumes of atomised samples, which can be captured in ion-funnels to provide an innovative interface between low volume (e.g. single cell) biology and mass spectrometry. Other examples of the applications of the device involve the selective concentration of particles with respect to their size or mass (i.e. their fractionation). This can underpin diagnostic applications in separating vesicles, cells and micro-organisms.

FIG. 1 shows a schematic example of a substrate in plan view. The substrate typically has a length of 20 mm and a width of 14 mm. The example of FIG. 1 is a funnel design, in which the sample manipulation zone 10 is bounded by a boundary zone 12. The boundary zone includes a phononic bandgap structure of holes formed in the substrate surface. The holes are arranged in a two dimensional square lattice pattern. In this example, each hole has a radius of 176 μm. In this example, the spacing between the centres of adjacent holes is 374 μm.

Figure 2:
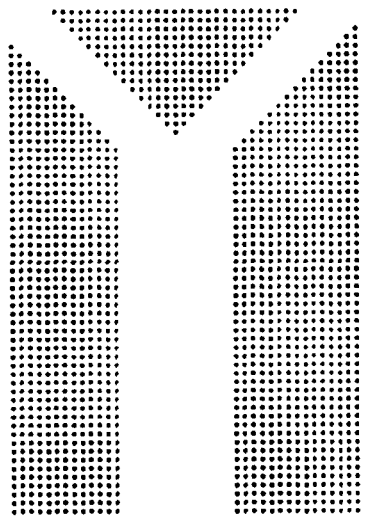
FIG. 2 shows a schematic plan view of another substrate for use with the present invention, showing a "waveguide" type sample manipulation zone.

FIG. 2 is similar to FIG. 1, except that the design is a waveguide design.

Figure 3:
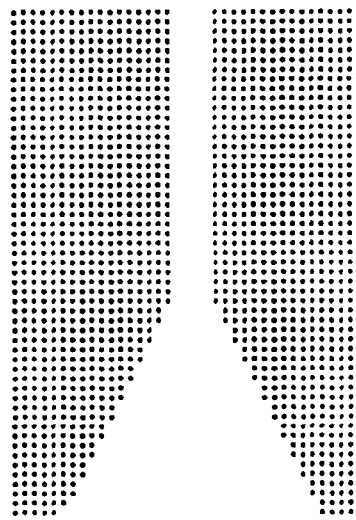
FIG. 3 shows a schematic plan view of another substrate for use with the present invention, showing a "combination" type sample manipulation zone

FIG. 3 is similar to FIG. 1, except that the design is a combination design.

In order to manufacture the substrates shown in FIGS. 1-3, a 4 inch (9 cm) silicon wafer was coated in AZ4562 photoresist and a pattern transferred into the resist using photolithography. The pattern consisted of a square array of circular holes arranged to provide a funnel, a waveguide with split or combination of funnel and waveguide, as shown in FIGS. 1-3, respectively.

The photoresist pattern was used as a dry etched mask where the holes were etched to a depth of approximately 230 μm. This depth equated to half the thickness of the Si wafer. The wafer was then cleaned in acetone and then cleaved to provide individual test structures. The test structures were cleaned again given an oxygen plasma treatment and then immersed in a solution of heptane and a tri-chloro-tri-decafluoro-octylsilane in order to give a hydrophobic surface to the silicon test structures, contact angle >65°.

The surface acoustic wave source consisted of a 3 inch (6.75 cm) $LiNbO_3$ with an interdigitated electrode structure. This is referred to as an interdigitated transducer (IDT). The IDT was resonant at a frequency of 6.18 MHz and SAWs at this frequency were used for the tests. A programmable signal generator was used to provide an input of 6.18 MHz with amplitude of −10 dBm (1 μW) pulsed at 50 Hz to an amplifier with 40 dB gain to present approximately 10 dBm (1 W) to the IDT.

De-ionised water was used as a coupling agent between the silicon test substrates and the lithium niobate wafer; approximately 10 μL was used for this purpose. In order to test mobility and atomisation, the droplet size was about 2 μL.

During testing, each of the structures shown in FIGS. 1-3 influenced the movement of the water droplets on the silicon surface. The structure that appeared to function most efficiently was the funnel (FIG. 1) and this was primarily thought to be due to the relative size of the structure, although the inventors do not wish to be bound by theory in this regard. The funnel efficiently moved and focused the drops to the focal point of the funnel irrespective of the initial starting point of the droplet in the sample manipulation zone. Although the test structures were used multiple times their efficacy decreased with usage, as it was difficult to adequately clean dried droplet stains from the exposed silicon surface. This suggests that the substrate should, where possible, should be used only once and then disposed of.

The waveguide structure (FIG. 2) provided guiding of the water droplets and reduced or eliminated wander of the droplet trajectory on the silicon surface that would be observed without the border zone. No splitting of droplets was observed although movement into either waveguide split was observed.

The combination structure (FIG. 3) provided focusing of droplets to the waveguide structure and transit along the structure was also observed.

Atomisation of water droplets could be achieved on all structures. This is discussed in more detail below.

Figure 4:
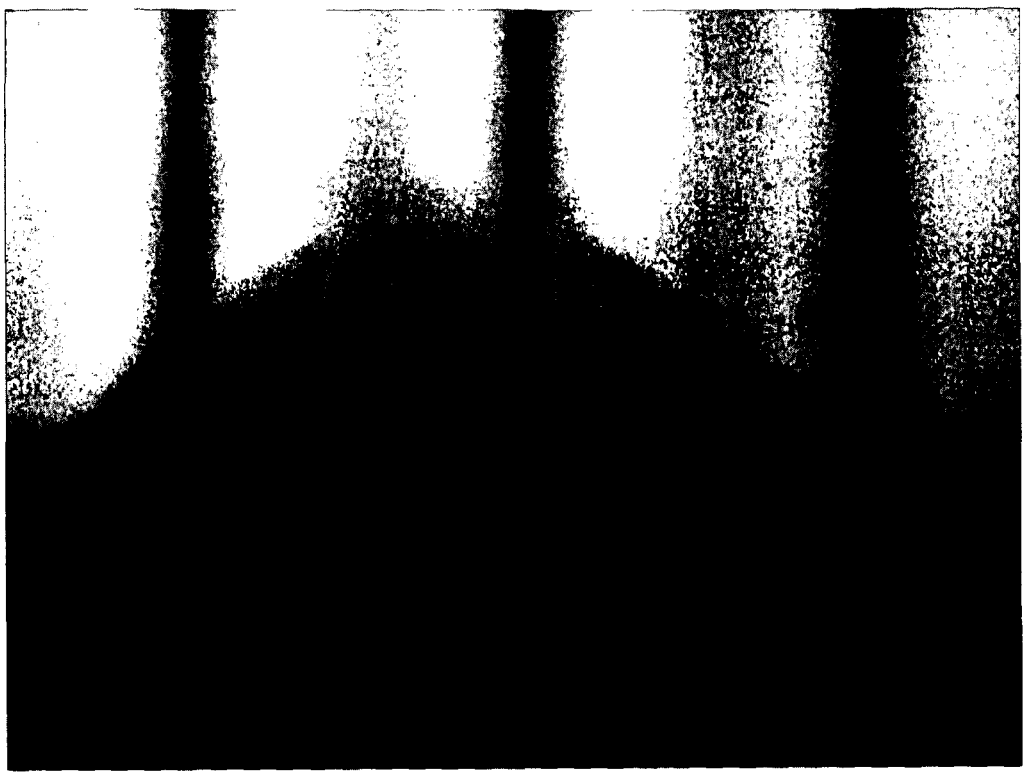
FIGS. 4 and 5 show micrographic images from a video sequence captured on a droplet, viewed from the side, on substrates coupled to a piezoelectric device in the manner described above.
Figure 5:

FIGS. 4 and 5 show micrographic images from a video sequence captured on a droplet, viewed from the side, on substrates coupled to a piezoelectric device in the manner described above. FIG. 4 shows a droplet on a plain silicon surface without a border zone. FIG. 5 shows a droplet on a substrate according to an embodiment of the invention (i.e. having a border zone with a phononic band gap structure as described above). The image in each case is taken approximately 250 microsecs after the surface acoustic wave meets the droplet. As can be seen, more energy is transferred to the droplet in FIG. 5 than in FIG. 4. Each droplet has a volume of 1 μL. The power used in these experiments was 0 dBm input which supplied 5 W at the IDT. The excitation frequency was 9.56 MHz. The dimensions of the substrates were 2 cm by 1.5 cm. The amount of coupling fluid was reduced to 4 μL—this provided a layer of approximately 13 μm thick. The substrates were placed in the same position and were of the same thickness (450 μm).

Further details relating to the preferred embodiment of the device are set out below.

Figure 6:
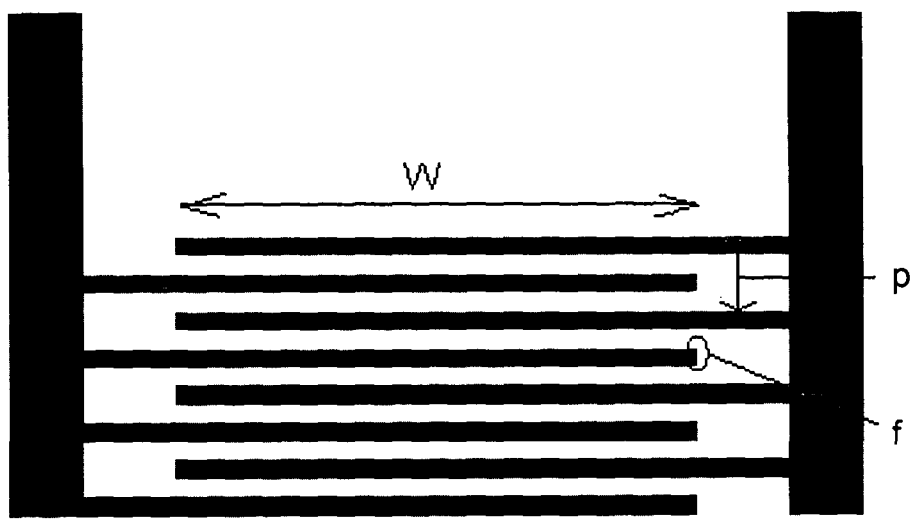
FIG. 6 shows a plan view of an electrode structure for use on a transducer for use with an embodiment of the invention. The electrode overlap w is 15 mm, the finger width for each electrode is 170 μm and the finger pitch p is 330 μm.

A piezoelectric device was fabricated on a 128° Y-cut X-propagating 3 inch (6.75 cm) $LiNbO_3$ wafer. Transducers were formed on the wafer, each having 20 pairs of electrode "fingers" to form interdigitated transducers (IDT). The electrode "fingers" were located with approximately 330 μm pitch p, 180 μm finger width f, with 15 mm aperture w (overlap), see FIG. 6. The direction of overlap of the fingers can be considered to be a transverse direction of the IDT. The electrodes were patterned using a lift off process where after photolithography, using acetate masks, a 20 nm adhesion layer of titanium was deposited prior to 100 nm of gold onto the wafer, lift off was then carried out in a beaker with acetone to produce the IDT electrodes for the SAW device.

An Agilent MXG Analog Signal Generator N5181A 250 KHz 1 GHz, in conjunction with a Mini Circuits ZHL-5W-1, 5-500 MHz amplifier, was used to power the SAW device. The amplifier was powered by a TTi EX354D Dual Power Supply 280 W that could supply 3A and ±24V DC. Approximately 1 W of power was applied to the IDT. The driving signal for the SAW device was pulsed for 20 ms every 100 ms, to avoid excess heating. Droplets were imaged at 62 frames per second using a high speed camera (Red Lake M3), which allowed the capture of atomisation from single pulses to be visualized, when the surface acoustic waves travelled through the droplet.

Figure 7:
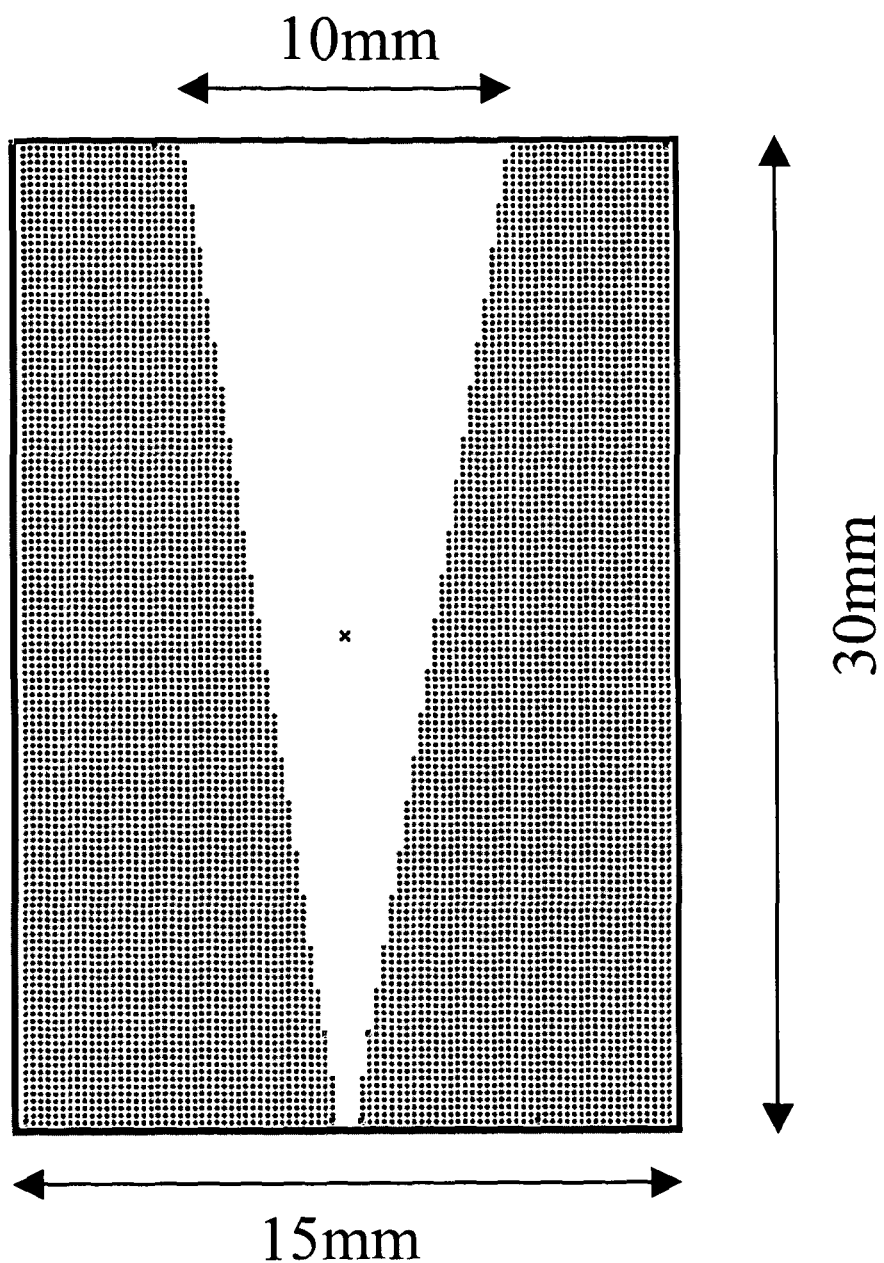
FIG. 7 shows a schematic plan view of a disposable substrate for use with an embodiment of the invention, including typical (but non-limiting) dimensions.

FIG. 7 shows a schematic plan view of a disposable substrate for use with this embodiment. This substrate was constructed using a silicon wafer with a thickness of about 0.5 mm. The 4 inch Si wafer was coated in AZ4562 photoresist and patterned using photolithography. The pattern consisted of a square array of circular holes arranged to provide a funnel or cone of unpatterned silicon (sample manipulation zone). The photoresist pattern was then transferred into the silicon using dry etch where the holes were etched to a depth of approximately 0.23 mm. The wafer was then cleaned in acetone and then cleaved to provide individual test structures. The dimension of the cone patterned substrate was approximately 15 mm by 30 mm. The aperture for the cone was 10 mm and the apex was approximately 0.57 mm (corresponding to two holes missing).

De-ionised water was used as a coupling agent between the silicon test structures and the lithium niobate wafer; approximately 10 μL was used for this purpose, providing a coupling medium layer of less than about 20 μm between wafer and test substrate. In order to illustrate atomisation, two 1 μL drops were used, one at the apex of the cone, the other approximately 10 mm away from the apex.

The phononic structure in the border zone consisted of a square array of holes etched into silicon, to a depth about half way through the wafer. This regular perturbation in the Young's modulus of the material provides the material with a frequency dependent acoustic transmission or reflection property.

Figure 8:
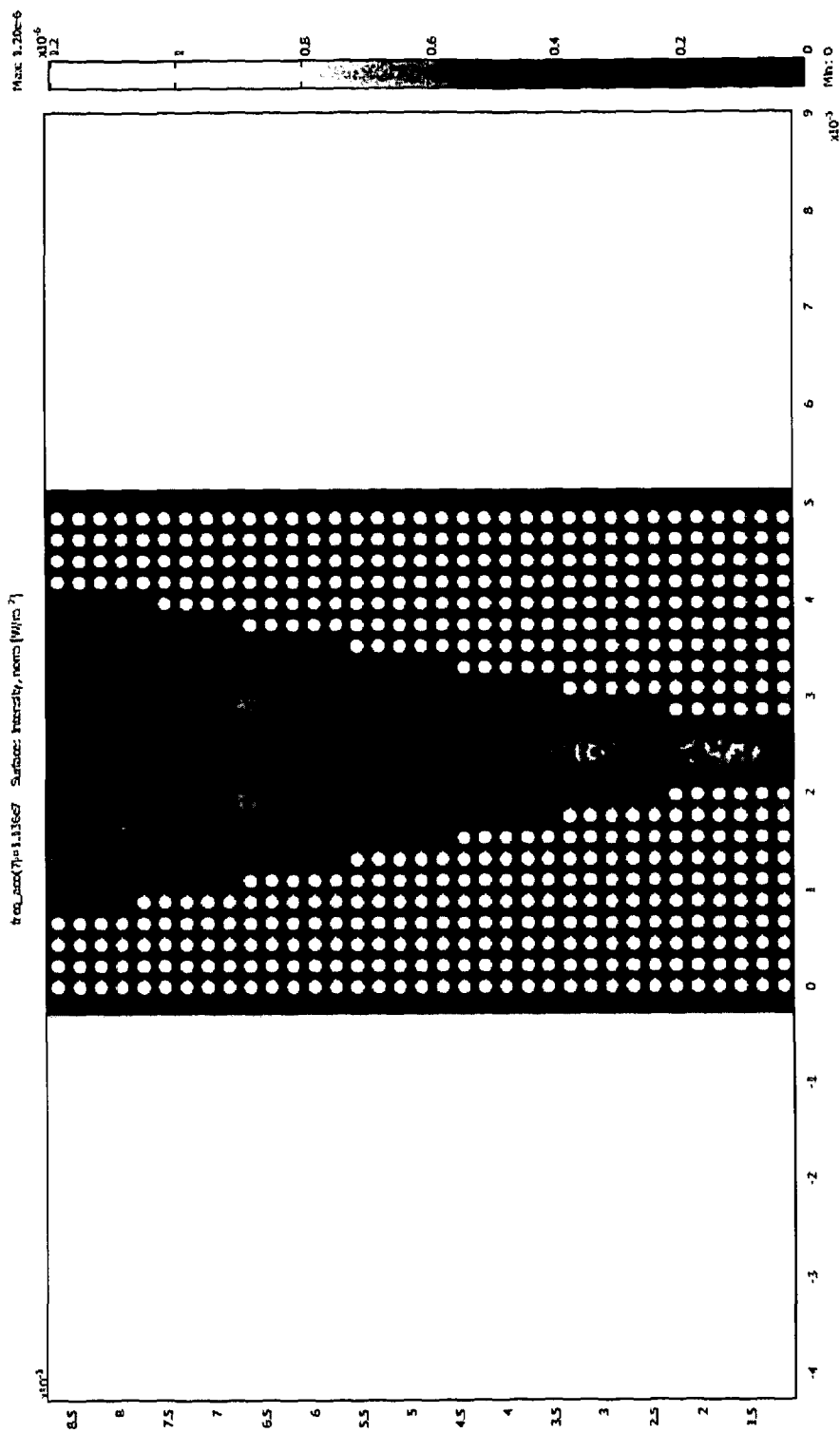
FIG. 8 provides a surface plot of the acoustic field intensity of a phononic cone structure illustrating the intensity at a first frequency of 11.36 MHz. The vertical and horizontal axes together denote position on the substrate surface.
Figure 9:
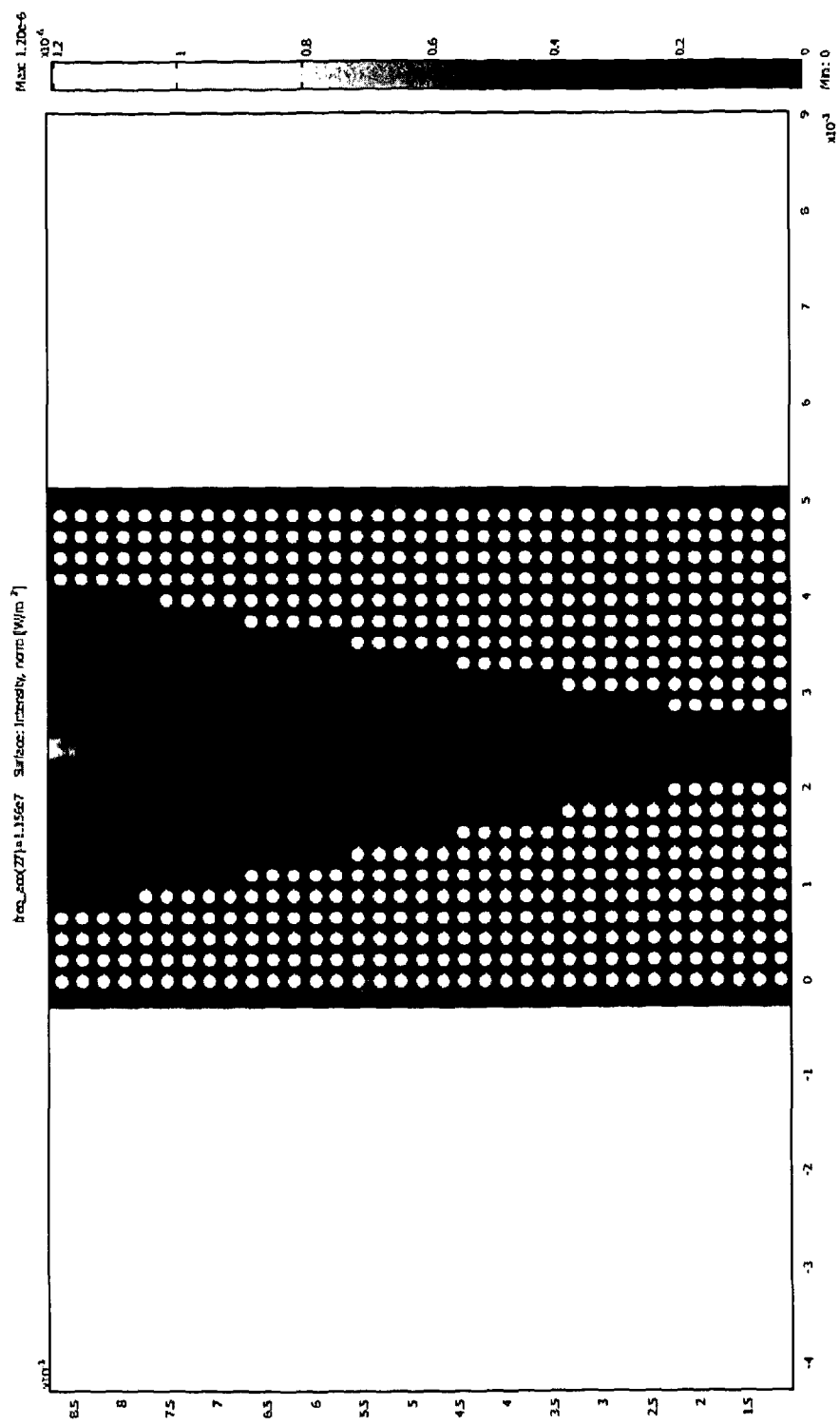
FIG. 9 provides a surface plot of the acoustic field intensity of a phononic cone structure illustrating the intensity at a first frequency of 11.56 MHz. The vertical and horizontal axes together denote position on the substrate surface.

FIG. 8 provides a surface plot of the acoustic field intensity of a phononic cone structure illustrating the intensity at a first frequency of 11.36 MHz. FIG. 9 provides a surface plot of the acoustic field intensity of a phononic cone structure illustrating the intensity at a first frequency of 11.56 MHz. These plots together show the effectiveness of the phononic structure to confine the acoustic field depending on the frequency used: a change of 200 KHz from 11.36 MHz to 11.56 MHz can provide a 3 dB change in intensity. The present inventors aimed to find the resonant frequency of the IDT to obtain the most efficient frequency to atomise the drops from the lithium niobate. In this case 12.85 MHz was found to be the resonant frequency for the IDT and droplet atomisation from the lithium niobate surface. However, this frequency of operation did not provide suitable operation of the phononic structures in the border zone. It was observed that by reducing the excitation frequency for the IDT down to 12.64 MHz a dramatic increase in atomisation was observed on the substrates with phononic structures. The increase in substrate activity was more than enough to compensate for any decrease in IDT acoustic conductance (the amount of electrical power that can be transformed into mechanical power).

The wavelength of the SAW depends on the pitch of an IDT. However, the observed change in acoustic response of the phononic structure would indicate a change in the wavelength of the SAW and hence variation in the pitch of the intedigitated electrodes.

This variation was a consequence of using acetate masks for prototyping. The masks did posses a variation in the electrode thickness but these variations were thought to be insignificant, which appears not to be the case. So in effect the inventors were using an IDT with a range of pitches allowing a number of possible wavelengths to be radiated.

In an alternative embodiment, the transducer uses a slanted interdigitated electrode structure. This is then used as a tunable source of SAWs. By slanting the electrodes the inter-electrode distance changes with lateral position across the electrode structure. This arrangement can be modelled by an array of IDT's with differing inter electrode spacing. The position of the SAW depends on the excitation frequency used.

The device of the present embodiment was designed for a certain operating wavelength (frequency) but typically there are always some deviations from the design parameters due to manufacturing tolerances during fabrication. As shown in FIGS. 8 and 9, the phononic structures are highly frequency/wavelength dependent. Therefore, by varying the excitation frequency slightly away from the predicted operating frequency, it is possible to tune in to a useful operating regime where the SAW wavelength is shifted enough to allow the device to function substantially as designed.

FIGS. 10-13 show a series of consecutive frames from video footage of an embodiment of the device operating. These images clearly show that acoustic energy is being focused and reflected.

In FIGS. 10-13, two 1 μL droplets have been placed onto the surface of the silicon phononic substrate. The first droplet is directly in the path of the second droplet, about 10 mm behind the first droplet. The second droplet should in effect "steal" some of the acoustic energy before the acoustic energy can reach the other first droplet. This would be observed, for example, if the droplets were located on the surface of the piezoelectric transducer (and without a border zone). Despite this, atomisation was observed only for the first droplet, at the apex of the phononic cone. The length of the substrate in this case was 30 mm. The power used in this case was five times lower than in the experiments reported above.

Atomisation for 0.5 μL drops has been observed at 790 mW applied power.

FIG. 10 shows the first of a series of frames taken from a movie captured at 62 frames per second. This first image is just prior to an ultrasonic SAW pulse arriving at the droplets at about 4000 m/s. Approximately 1 W of power was applied to the IDT.

FIG. 11 shows the droplets irradiated by the SAWs with the second droplet clearly agitated but not atomising, whereas the first drop near the apex of the cone is atomising (or more correctly nebulising).

FIG. 12 shows a frame in which the 20 ms pulse has stopped but some free oscillation in the drops can be observed. It is interesting to note that the drop that was atomising was in the shadow of the second drop and would normally experience much less acoustic radiation as the second drop would absorb a significant amount of the Rayleigh wave energy.

In FIG. 13 the oscillations have stopped and only the plume expelled from the first drop can be seen. This illustrates the efficacy of the device.

The design, construction and investigation of the embodiment of the device shown in FIGS. 10-13. will now be described in more detail.

The surface acoustic waves were generated on the piezoelectric $LiNbO_3$ wafer by an interdigitated transducer (IDT) and propagated as Rayleigh waves, in a non dispersive manner with a single velocity. The resonant frequency, $f_0$, is directly related to the Rayleigh wave velocity in the material, $c_R$, (3996 m/s), the SAW wavelength $\lambda$ and the pitch of the interdigitated electrodes, D, as per equation (1):

$$\lambda = \frac{c_R}{f_0} = 2D \qquad (1)$$

The Rayleigh waves were coupled into a substrate in the form of a sheet, or plate (which substrate sheet or plate may be referred to as a chip), via an intermediate thin film of water. As a free plate, the substrate supports a number of propagation modes, termed Lamb waves (named after Lamb, the first to carry out the analysis). There are two distinct classes of Lamb wave propagation modes, symmetric and antisymmetric, that can be resolved using the Rayleigh-Lamb frequency equations (2) and (3).

$$\frac{\tan\left(\frac{qd}{2}\right)}{\tan\left(\frac{pd}{2}\right)} = -\frac{4k^2 pq}{(q^2 - k^2)^2}, \text{ symmetric modes} \quad (2)$$

$$\frac{\tan\left(\frac{qd}{2}\right)}{\tan\left(\frac{qd}{2}\right)} = -\frac{(q^2 - k^2)^2}{4k^2 pq}, \text{ antisymmetric modes} \quad (3)$$

where $$p^2 = \left(\frac{\varpi}{c_L}\right)^2 - k^2,$$

$$q^2 = \left(\frac{\varpi}{c_T}\right)^2 - k^2,$$

and $$k = 2\pi/\lambda = \varpi/c_{phase}$$

with d the plate thickness, and $c_L$ (8433 m/s) and $c_T$ (4563 m/s) the longitudinal and transversal velocities, respectively.

These transcendental equations, with many real solutions, reveal that Lamb waves are dispersive, as the phase velocity, $c_{phase}$, is a function of the frequency thickness product f×d. Thus for a fixed frequency, the wavelength and the mode propagated in the substrate sheet can be controlled via its thickness.

Figure 14:
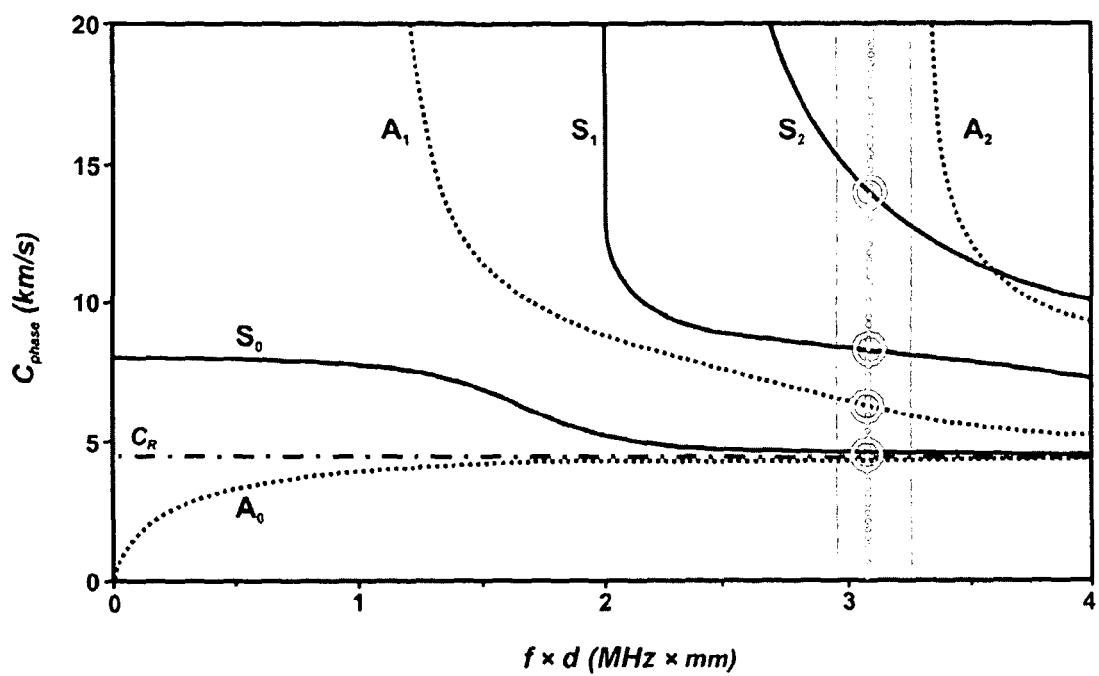
FIG. 14 shows the dispersion curve for a free plate, with phase velocity as a function of excitation frequency.

FIG. 14 shows the dispersion curve for a free plate, with phase velocity as a function of excitation frequency. At 12.6 MHz, two asymmetric and three symmetric modes can be excited. The phase velocities of the lowest order modes $A_0$ and $S_0$ are the closest to that of the propagating Rayleigh wave in the substrate sheet ($C_{phase}$, 3996 m/s), which the inventors worked with, and thus these modes are excited in preference to higher order ones. The inventors used these data, together with previously published criteria for phononic plate structures [Djafari-Rouhani B et al. (2008) Absolute band gaps and waveguiding in free standing and supported phononic crystal slabs. Photonics and Nanostructures—Fundamentals and Applications 6:32-37] to design phononic structures to manipulate fluid.

These phononic structures were then modelled as simple 2-D diffraction problems, where the acoustic waves were described using a time harmonic Helmholtz wave equation (4), in which a pressure wave, P, was launched into the structure (density ρ), over a range of wavelengths calculated from the Lamb wave number, k, at a particular (fd) product.

$$-\nabla \cdot \left(\frac{1}{\rho}\nabla P\right) - \frac{k^2 P}{\rho} = 0 \quad (4)$$

The inventors developed simple phononic structures, where the lattice comprises an array of holes, and where all cases were treated with Neumann boundary conditions. Using these design criteria the inventors produced a series of square lattice 2D phononic crystals, which amplified or shaped the acoustic field, within the substrate sheet. The phononic crystal was used to create acoustic cavities, which were excited at different wavelengths, resulting either in scattering or reflection of the energy. This can focus the energy into specific regions of the chip. As a consequence, the interaction between the Lamb wave and the phononic lattice generates spatial variations of the acoustic field intensity, associated with the different propagation regimes within the chip.

Importantly, energy losses that occur during the coupling of the acoustic wave from the lithium niobate wafer into the substrate sheet are mitigated against by the phononic structure, which can focus the power into specific regions of the chip.

The Lamb waves propagated in the chip interact with the droplet of liquid placed on its surface in a similar fashion as Rayleigh waves in a piezoelectric material would. In the case of Rayleigh waves, the interaction with the liquid dampens the surface-propagating wave, which decays as it propagates along the surface. It is then termed a leaky Rayleigh wave and radiates a compressional wave into the liquid, which cannot support shear waves. Similarly, a droplet of liquid placed on the substrate renders the Lamb waves evanescent, with the acoustic energy being refracted into the liquid at an angle termed the Ralyeigh angle $\theta_R$, determined by Snell's law (equation 5) relating the speed of the waves in solid and liquid:

$$\sin\theta_R = \frac{c_{liquid}}{c_{solid}} \quad (5)$$

Depending on the power applied, different fluidic regimes can be induced in the droplet, from (acoustic) streaming where volumetric flow is created throughout the drop by recirculation, to the destabilisation of the contact line resulting in droplet movement, as well as nebulisation and jetting by disrupting the drop's free surface into smaller droplets. Examples of the spatial control of the acoustic energy upon the different regimes on the phononic substrate sheets are described in more detail below.

The SAW device was fabricated on a 128° Y-cut X-propagating 3 inch $LiNbO_3$ wafer, each device consisted of 20 pairs of electrodes to form an inter-digitated transducer (IDT) with pitch of 160 μm, 80 μm width, and a 10 mm aperture. The SAW IDTs were patterned using a lift off process where, after pattern transfer into an S1818 resist, a 20 nm titanium adhesion layer was evaporated prior to deposition of 100 nm of gold. Lift-off was then performed in acetone, in order to realise the pattern.

An Agilent Technologies MXG Analog Signal Generator N5181A was used in conjunction with a Mini Circuits ZHL-5W-1, 5-500 MHz amplifier and a 3A, ±24V DC power supply to power the SAW device. For nebulisation experiments, the driving signal for the SAW device was pulsed for 20 ms every 100 ms, to avoid heating. Droplets were imaged at 62 fps using a Red Lake M3 high-speed camera mounted on a Leica upright microscope, which allowed the capture of nebulisation from the droplets to be visualized, when the surface acoustic waves travelled through the droplet. The IDT's were characterised using an Agilent Technologies E5071C ENA series network analyser.

The substrate was fabricated using silicon wafer with an approximate thickness of 470 micrometer. The 4 inch Si wafer was coated in AZ4562 photoresist and patterned using standard photolithography. The pattern comprised a square array (pitch 203 micrometer) of circular holes (radius 82 micrometer) and was transferred into resist layer. The photoresist pattern was then transferred into the silicon using dry etch (STS ICP) where the holes were etched. The wafer was cleaned in acetone and cleaved to provide the substrates. The dimension of the patterned substrate was approximately 20 mm by 30 mm. In the case of the acoustic horn, the aperture for the cone was made to be 10 mm to coincide with the IDT aperture and the apex of the cone was approximately 1.22 mm wide. (In the case of the centrifugal filter, described further below, the same square array of circular holes was used and actuation of the fluid was observed with 10 micrometer polystyrene beads (Duke Scientific G1000)). A 5 microliter volume of de-ionised water was placed between the substrate and the transducer surface to provide a coupling layer approximately 50 micrometer thick to promote SAW coupling.

Figure 15:
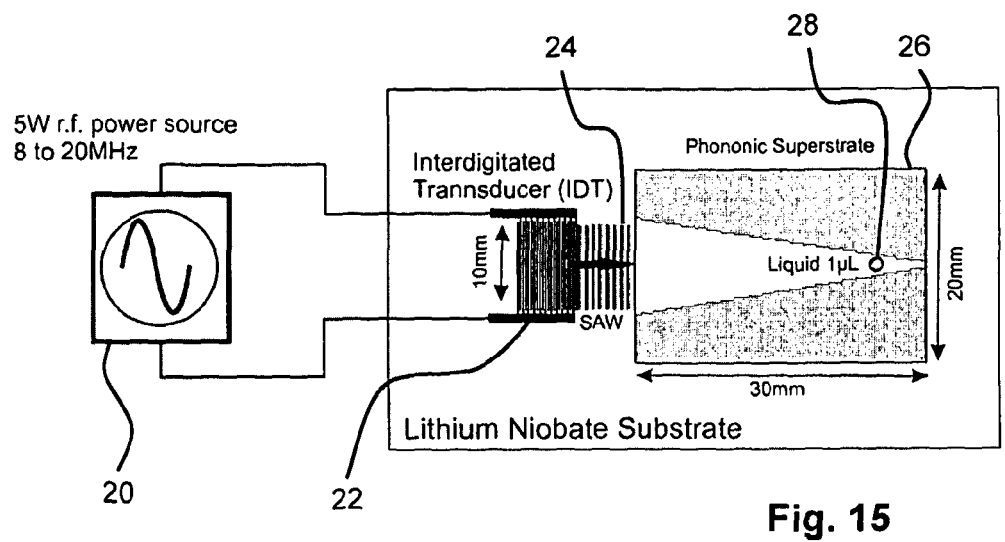
FIG. 15 shows a schematic view of a device according to an embodiment of the invention. A separable phononic substrate (or phononic superstrate) in the form of a phononic cone is shown coupled to a lithium niobate substrate which comprises an IDT.

A schematic of the device is shown in FIG. 15, which depicts the application of sinusoidal wave from a 5 W rf power source 20 (operable in the range 8 to 20 MHz) to the interdigitated transducer (IDT) 22 having an aperture of 10 mm to generate a Rayleigh Wave (SAW) 24. The SAW on the $LiNbO_3$ wafer surface induces Lamb waves in the substrate 26 coupled to the $LiNbO_3$ wafer surface (such a separable, couplable substrate may be referred to as a superstrate), where the intensity was focused at the 1 µl drop 28. The IDT electrodes had a pitch of 160 micrometer, electrode widths of 80 micrometer and an aperture of approximately 10 mm. The phononic crystal comprised holes of 82 micrometer radius with a pitch of 203 micrometer, to provide a fill factor of 0.8, etched into [100] silicon (where structure was aligned to the [011] direction of the silicon wafer, the propagation direction of the Lamb waves was parallel to the [011] direction).

Figure 16:
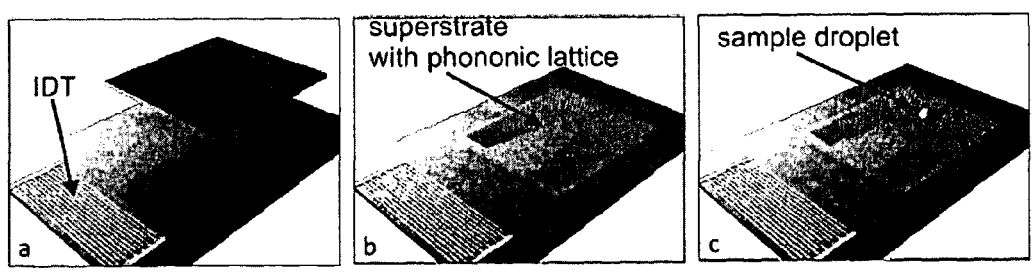
FIG. 16 shows a schematic view of a device according to an embodiment of the invention. A separable phononic substrate (or phononic superstrate) patterned with a phononic lattice in the form of a phononic cone is shown (a) separated from and (b) coupled to a lithium niobate substrate which comprises an IDT. In (c) a sample droplet is located near the apex of the phononic cone.

FIG. 16 provides schematic perspective views of the device. FIG. 16a illustrates the transducer arrangement, comprising a lithium niobate wafer and an IDT, on to which a substrate including a phononic lattice (a phononic substrate) is to be placed. FIG. 16b shows the phononic substrate on the transducer arrangement. FIG. 16c shows the droplet to be manipulated placed onto the phononic substrate.

The phononic substrate was designed in the form of a phononic cone in order to focus the acoustic energy, as a series of steps (or cavities), with each feature being resonant at a particular frequency, and acting as a Fabry Perot cavity [Qiu C, Liu Z, Mei J, Shi J (2005) Mode-selecting acoustic filter by using resonant tunneling of two-dimensional double phononic crystals. *Appl. Phys. Lett.* 87:104101-104103; Wu T T, Hsu C H, Sun J H (2006) Design of a highly magnified directional acoustic source based on the resonant cavity of two-dimensional phononic crystals. *Appl. Phys. Lett.* 89:171912-171913]. FIG. 17a shows a schematic drawing of the device, similar to FIG. 16c. The droplet is shown placed on the phononic substrate (phononic cone), and the phononic substrate is coupled to the transducer arrangement.

Figure 17:
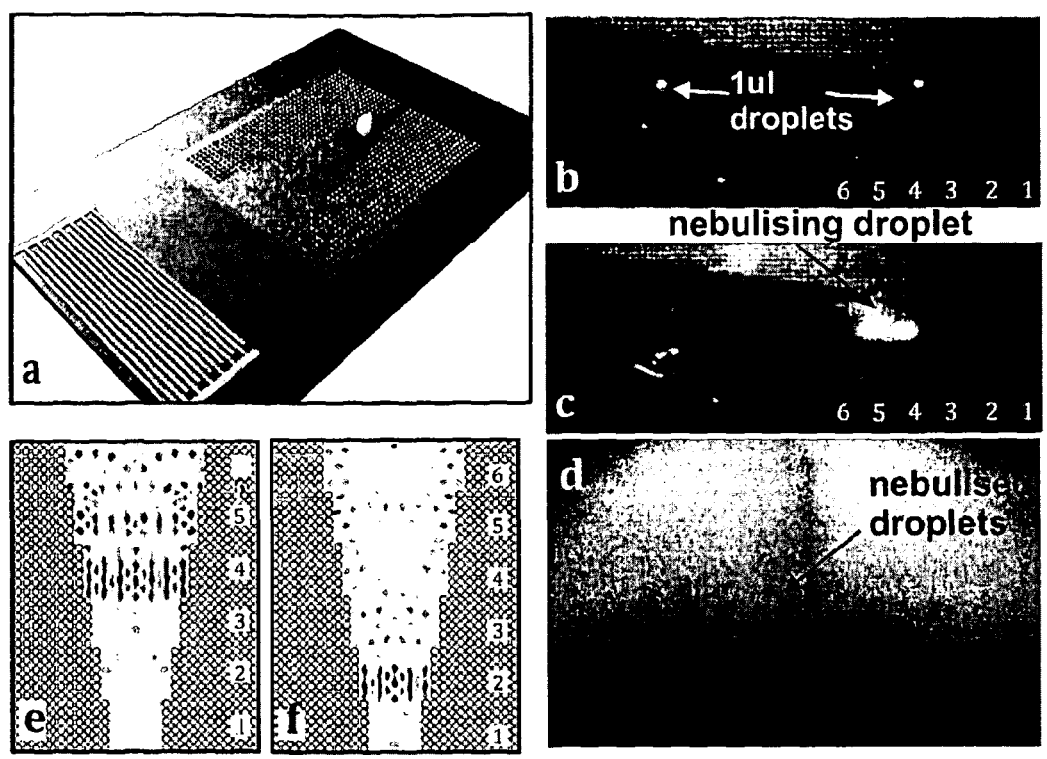
FIG. 17 shows (a) a schematic diagram of an embodiment of the device in use; (b) and (c) a series of consecutive micrograph frames from video footage of an embodiment of the device operating; (d) a micrograph of a nebulised droplet; and (e) and (f) simulations of an embodiment of the device operating at two different frequencies, showing that input frequency can be used to excite specific cavities within a phononic cone.

Six steps, or cavities, of the phononic cone are numbered 1 to 6 in FIGS. 17 b and c.

These show micrographic stills from a movie captured at 62 fps before and during nebulisation, with the device being excited at 12.6 MHz with an applied power of 1.25 W. In FIG. 17b the droplets are quiescent and their position can only be seen from light reflections. In FIG. 17c the droplet in the fourth cavity is nebulised, whilst that in the tenth cavity (not numbered in FIG. 17) was agitated, and thus became visible, but was not nebulised. (FIGS. 17b and c correspond to the images shown in FIGS. 10 and 12). FIG. 17d presents a side view captured with a fast camera and shows a picture of the flattened droplet during nebulisation captured at 4 000 frames per second (using a Phantom 7.1 camera, Research Vision, Inc.). The nebulised mist can be seen above the drop.

Acoustic waves on the surface of the substrate, within the phononic structure were observed using white light interferometry, and the wavelengths measured on both the $LiNbO_3$ wafer and on the substrate within the phononic structure. The inventors chose an excitation frequency of the IDT, driving the SAW, in order to excite particular cavity modes within the phononic substrate (i.e. cavities 1 to 6 in FIG. 17). For example, the fourth cavity readily accommodated the contact area of the drop and was excited at 12.6 MHz.

FIGS. 17 e and f show simulations of the phononic cone structure when excited at 12.6 MHz and 13.2 MHz respectively. Standing waves develop as a consequence of the sidewalls acting as a series of Fabry Perot etalons. The standing waves in the cavities are of up to an order of magnitude larger than the acoustic field on an unmodified substrate (a substrate with no phononic lattice), depending on the frequency. Each cavity could be excited at different frequencies, where there was about 300 KHz spacing between each cavity (i.e. between cavities 1 and 2; between cavities 2 and 3, etc). For example the second cavity showed the highest enhancement factor of about 10 at 13.2 MHz whereas the fourth cavity showed an enhancement of about 6 at 12.60 MHz excitation. The phononic cone was modelled as a simple 2-D diffraction problem using COMSOL Multiphysics v3.5a.

The data presented in FIGS. 17 e and f show that different cavities of the device can be excited at different frequencies. The device has been designed so that the phononic structure acts as an efficient reflector and little energy is dissipated into the lattice. The simulations also show that the spatial variation in acoustic intensities, as well as the generation of standing waves, were perpendicular to the direction of propagation of the Lamb waves. Changes in frequency of 0.6 MHz can provide significant variations in acoustic field intensity, a fact corroborated experimentally.

Figure 18:
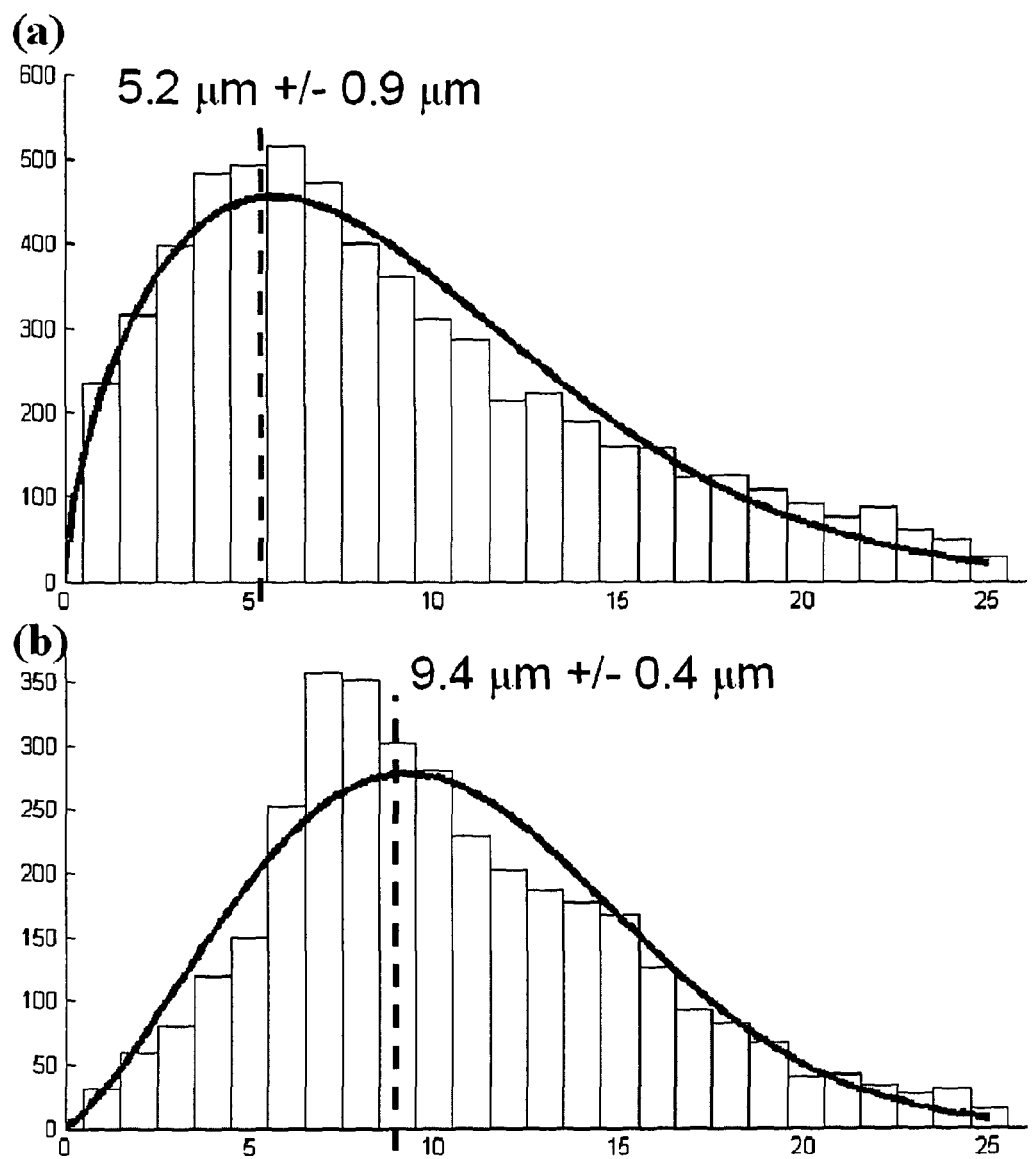
FIG. 18 shows the size of droplets ejected during nebulisation performed (a) on a phononic substrate coupled to a piezoelectric transducer arrangement, and (b) directly on the surface of the piezoelectric transducer arrangement.

The nebulisation phenomenon has been studied further. When relatively high powers are applied, the acoustic energy overcomes the surface tension pinning the drop to the surface so that it spreads out in a liquid film (FIG. 17d) and gives rise to capillary resonance waves in the liquid which are determined by internal viscous damping and inertial forcing of the drop. These capillary waves have a wavelength on the order of the diameter of the nebulised drops with volumes in the sub-picoliter range. FIG. 17d shows the nebulisation of a 1 microliter droplet proceeding on the phononic substrate. The droplet was placed in a cavity of the cone phononic substrate and nebulised using SAWs excited with a frequency of 12.6 MHz and a power of 4 W. FIG. 18 shows the size of droplets ejected during nebulisation. Nebuisation of water droplets (1-2 microliters) was performed on the cone phononic substrate coupled to the piezoelectric transducer arrangement (FIG. 18a) or directly on the surface of the piezoelectric transducer arrangement (FIG. 18b) with excitation frequencies around 12 MHz (+/−1.2 MHz). The size of the droplets ejected was measured with a Phase Doppler Particle Analyser. The data set from each experimental run (with multiple runs per condition) was fitted with a Weibull distribution and the modes extracted using Matlab (R2010a, The Mathworks, Inc.). An example of the fitted distribution, superimposed on the histogram, is shown for one run for each condition. Values presented are the average of the modes obtained for each condition with the standard deviation. Interestingly this data also shows that droplets nebulised on a phononic superstrate are smaller than on the IDT. Two other modes not associated with nebulisation were observed, with droplets sizes centered around 50 µm) and 150 µm, resulting from jetting phenomena. The diameter of the droplets nebulised from the surface of the phononic cone substrate was measured at 5.2 micrometer(+/−0.9 micrometer), and was not significantly different from a nebulisation happening on an unstructured substrate.

However, a major difference with using an unstructured substrate lies in the large variation in the extent of nebulisation on the phononic substrate, which is dependent upon where the droplet was placed within the cone. This precise spatial control of the acoustic field is also seen experimentally in FIG. 17 which shows an (b) image captured prior to application of the SAW and (c) an image captured during application of the SAW. The latter clearly shows that excitation of the droplet in the fourth cavity at 12.6 MHz resulted in nebulisation, whilst there is no excitation 10 mm away, in cavities within the trumpet of the cone. The spatial control of the acoustic energy also enabled the reproducible placement of the drop on the phononic substrate as it aligned itself to the excited cavity when deposited around it, as described further below.

Droplet movement and splitting was observed using the device shown in FIG. 17, as described below.

When the acoustic radiation applied or coupled in the substrate overcomes or is equal to the sliding force $F_s$ given by equation (6), droplet movement can be achieved.

$$F_s = 2R\gamma_{LG}\sin\left(\frac{\theta_a + \theta_r}{2}\right)(\cos\theta_r - \cos\theta_a) \quad (6)$$

In equation (6) R is the radius of the drop, $\gamma$ is the surface tension and $\theta_a$ and $\theta_r$ are the advancing and receding contact angles of the drop when no acoustic wave is applied.

Figure 19:
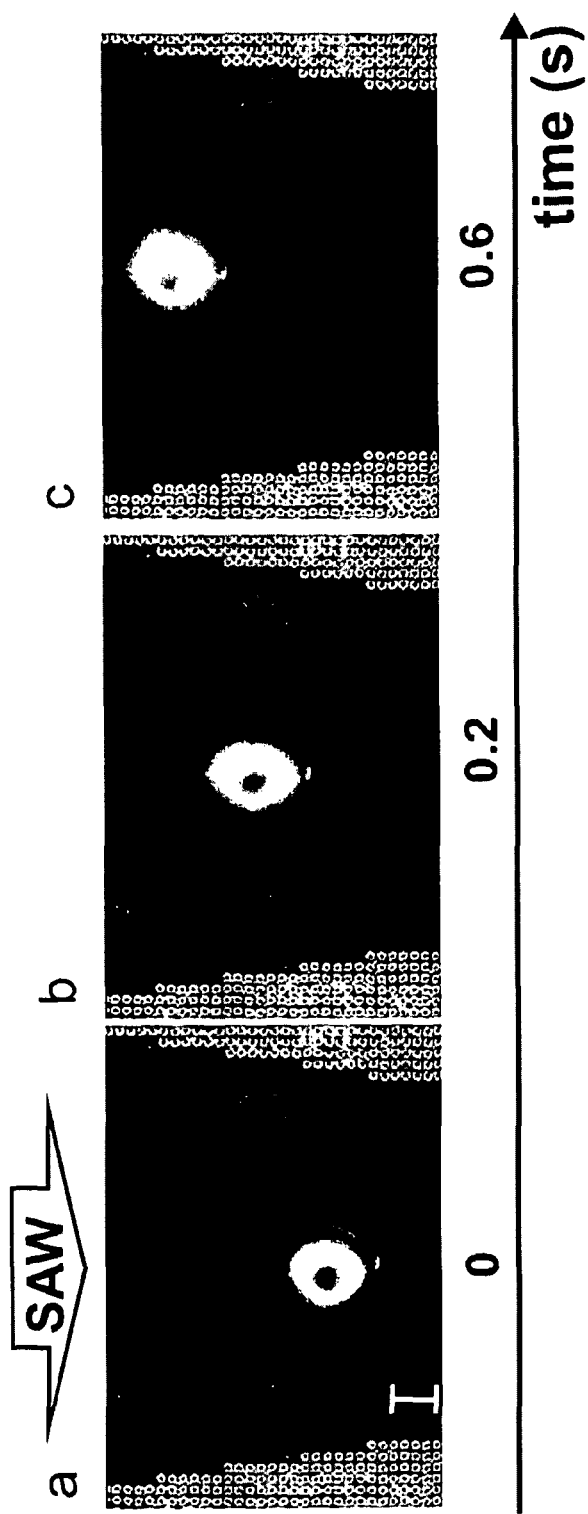
FIG. 19 shows movement of a droplet between cavities of a phononic cone.

By placing a droplet between two cavities, one of which is resonant, the spatial variation of the acoustic energy densities (as shown in FIG. 17), results in acoustic forces on the droplet which splits and/or moves of the droplet as it moves towards the cavity with the higher energy. By tuning the strength and frequency of the field in the cavities, relative to each other, droplets will either divide symmetrically or asymmetrically. The process of droplet movement or division is driven by refracted waves (one directed) and reflected waves in the opposite direction (back from the phononic cone). The mobility of the drop can be improved by reducing the contact angle hysteresis, by making the surface hydrophobic. For example, a 5 microliter water droplet was observed to move back and forth between 3 cavities of a phononic cone treated with a hydrophobic silane. FIG. 19 shows the movement of a 5 microliter water droplet between three cavities of a phononic cone, at different times (a. 0 seconds; b. 0.2 seconds; c. 0.6 seconds), when the exiting frequency is changed from 12.23 MHz (a) to 12.43 MHz (c) with increments of 0.1 MHz The propagation of the SAW directly on the piezoelectric wafer or an unstructured substrate coupled to the piezoelectric wafer resulted in droplet movements in the same direction as the SAW, whereas on the phononic substrate, the droplet was moved in the opposite direction to the SAW, by increasing the frequency from 12.23 MHz to 12.43 MHz (−3 dBm). It was brought back to the same position by decreasing the frequency from 12.43 MHz to 12.23 MHz.

The same transducer arrangement as described above, used for droplet nebulisation, splitting or movement, can be used to create an on-chip "centrifuge" (more correctly "separator", as discussed above, but others in the art use the term "centrifuge"), by using a different substrate, coupled to the transducer arrangement, as described below.

Figure 20:
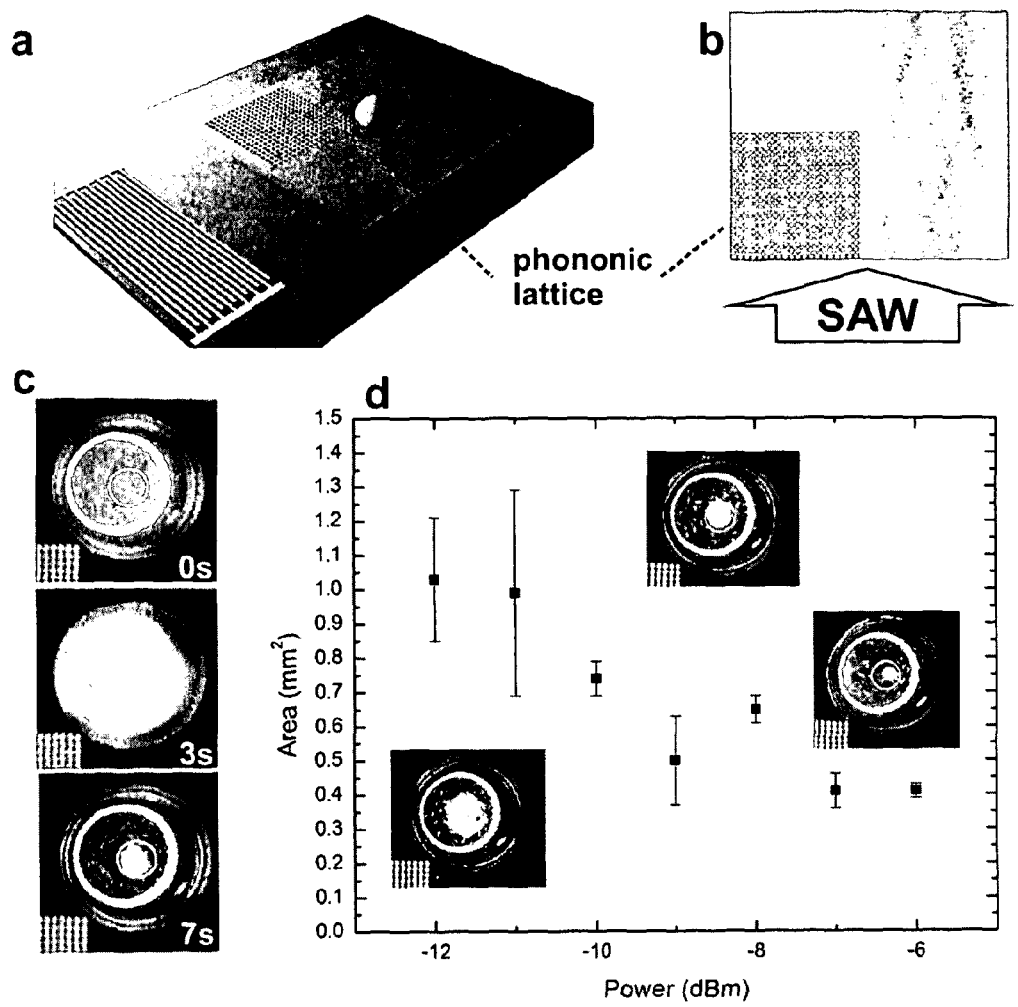
FIG. 20 shows (a) a schematic view of an embodiment of a device comprising a substrate that includes a phononic lattice in the form of a square, for use in centrifugation of a droplet; (b) a simulation of SAW intensity on the device showing that the phononic lattice interferes with the SAWs; (c) a series of micrographs showing concentration of particles in the centre of a droplet by centrifugation of the droplet on the device; (d) a graph showing that an in increase in power results in a higher local concentration of particles in the centrifuged droplet.

The device used for centrifugation of particles within fluid droplets is shown schematically in FIG. 20a. The transducer arrangement and substrate were made as described above with reference to FIGS. 10-19, except the phononic lattice was formed as a square, rather than as a cone.

FIG. 20b shows simulation results (Comsol multiphysics 3.5a) where a pressure wave was propagated in the superstrate at 12.6 MHz and has its symmetry broken by the phononic lattice. These results show that the phononic structure generates a difference in speeds of the induced Lamb wave in the substrate, breaking the symmetry of the acoustic wave and inducing angular momentum within the sample. The resulting flow patterns concentrate particles within the liquid, due to fluid motions which have similarities to those described by Batchelor [Batchelor G K (1951) Note on a class of solutions of the Navier-Stokes equations representing steady rotationally-symmetric flow. Q. J. Mech. Appl. Math. 4:29-41; Raghaven R V, Friend J R, Yeo L Y (2010) Particle concentration via acoustically driven microcentrifugation: microPIV flow visualization and numerical modelling studies. Microfluid. Nanofluid. 8:73-84].

Figure 21:
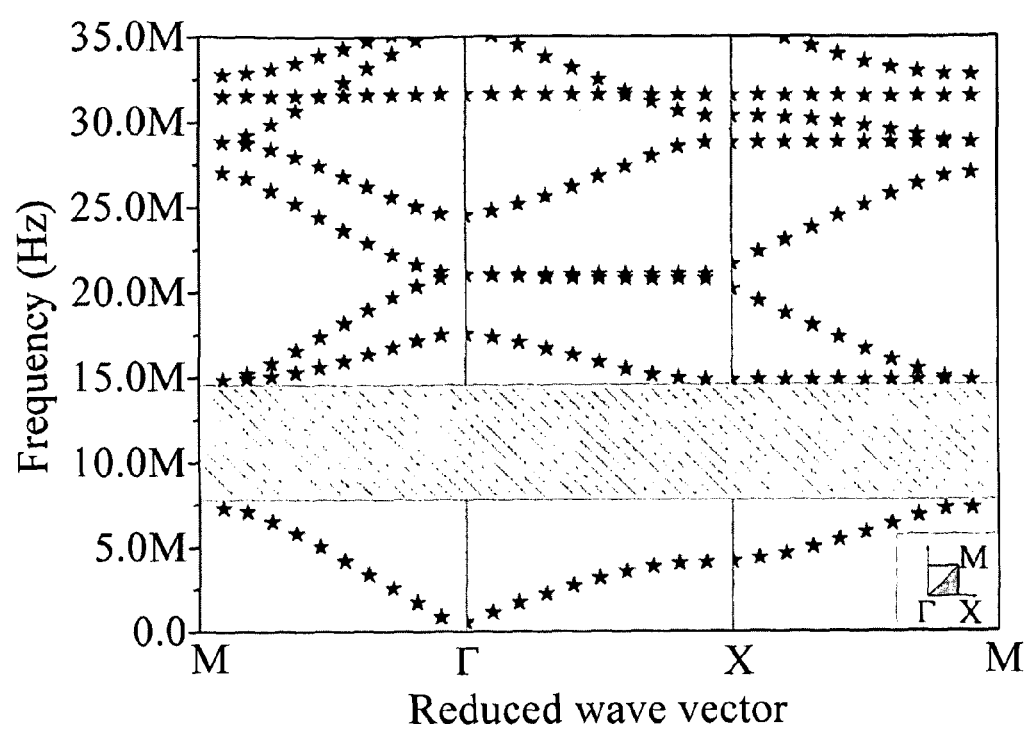
FIG. 21 shows the band structure of the phononic lattice shown in FIG. 20.

FIG. 21 shows the band gap of the square phononic array. The wave propagation was investigated using the two-dimensional plane wave expansion method [Hsu J and Wu T, (2006) Efficient formulation for band-structure calculations of two-dimensional phononic-crystal plates. Phys Rev. B, 74, 144303]. As will be understood by the skilled person, this type of reduced wave vector diagram is a convenient way to describe band gaps in symmetrical structures. Thus, in this example, where a phononic crystal has a particular symmetry, it is not necessary to consider all the possible propagation directions of a wave in the crystal. But by taking the symmetry of the structure into account it is only necessary to consider propagation in a reduced number of directions; for a square lattice (as in this example) we only need to take directions from 0 to pi/4 radians (0 to 45 degrees) with respect to one of the reciprocal lattice vectors of the crystal. The reciprocal lattice is the Fourier map of the crystal (or its diffraction pattern), where the wave vector of a wave is the direction of propagation with respect to the reciprocal lattice. For isotropic materials, it is only necessary to consider one direction of propagation, or one wave vector. The hatched area corresponds to the absolute band gap from 7.67 MHz to 14.48 MHz. These data complement those presented in FIG. 20b, showing the wave filtered by the phononic structure when propagated at 12.6 MHz.

In order to better understand the flow patterns generated by this type of phononic structure, the inventors explored the behaviour of beads within these flows. FIG. 20c shows micrographic stills at different time points from a 7 second experiment with 10 micrometer polystyrene beads in a 10 microliter water droplet, using a power of −8 dBm, ending with the concentration of the beads in the centre of the droplet. FIG. 20d shows the relationship between the increase in concentration (measured as the area covered by the beads at the end of the experiment using pixel counting image software) of 10 micrometer polystyrene in a droplet and the power applied to the piezoelectric wafer. The standard error of the mean is shown, with the extent of centrifugation measured using pixel counting image analysis software. Examples of stills from the experiments are shown as inserts for powers −12, −8, and −6 dBm respectively. These images show that the beads concentrate in the centre of the droplet in a manner related to the power, and hence the velocity of flow (analogous to the "tea leaf effect", explained by Batchelor).

Interestingly, the inventors observed anti-clockwise streaming with the configuration shown in FIG. 20a (with the phononic filter toward the left of the IDT and the left side of the droplet). However, if the microfluidic chip was turned through 90 degrees relative to the IDT (such that the phononic filter was positioned towards the right of the IDT and the right side of the droplet), then the observed fluid streaming was clockwise in direction.

Figure 22:
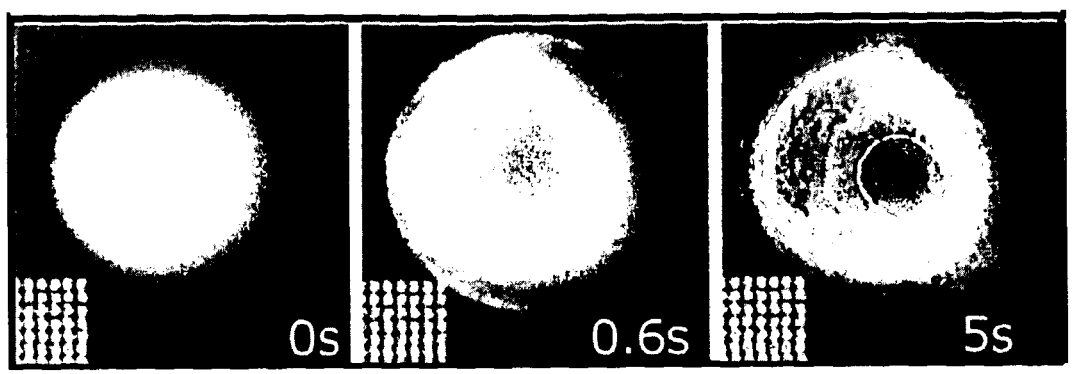
FIG. 22 shows a series of consecutive micrograph frames from video footage of an embodiment of the device operating to centrifuge blood cells in a droplet of diluted blood.

As a relevant example of a biological application, the concentration of blood cells from diluted blood samples was demonstrated. FIG. 22 shows stills from an experiment with blood (diluted 1:50 in PBS) using a power of −7 dBm, at different time points over a 5 second experiment, at the end of which the blood cells can be seen to concentrate in the middle of the 10 microliter droplet.

The inventors have demonstrated a new concept in microfluidics showing that complex microfluidic manipulations, including for example the centrifugation of blood, can be performed on a disposable phononic chip. The SAW excitation frequency was chosen to couple across the transducer-substrate interface, where droplet manipulation was achieved. The phononic structures interact with the acoustic field, providing excellent reflectivity or scattering to the incoming acoustic waves. The experiments described herein show how droplet actuation is dependent upon the geometric design and elastic contrast within the phononic crystal, as well as the frequency of the acoustic wave, and how a variety of different fluid motions on a disposable chip can be produced on-chip, including droplet movement, splitting, nebulisation and centrifugation (without the need for electrodes, channels or pumps, for example). This flexible and powerful method does not require complex interconnect technologies, nor high voltages (as is the case in many electrokinetic techniques). In the future, by combing different phononic structures, it will become possible to create a "tool-box" of different fluidic functions (each being modulated by the geometric structure and the frequency of the acoustic wave). Just as in electronics, where different components are combined to create a circuit, so, combinations of phononic lattices will produce complex microanalytical systems, on chip. Although the transducer arrangement (e.g. $LiNbO_3$ piezoelectric wafer) is relatively expensive, in accordance with the present invention it may be a re-usable platform for use with a low cost disposable substrate.

In conclusion of this section relating to phononic structures, the substrates made according to the preferred embodiments of the invention are very frequency and/or wavelength selective. The phononic structures do interact with the acoustic field if working in the correct operating regime providing good reflectivity to the incoming acoustic waves. It has been shown that such structures can be used to engineer the acoustic field to provide enhanced manipulation (such as atomisation) of liquid droplets from the substrate surface. Manipulation processes applied to the fluid sample can be one or more of:
  movement
  mixing (e.g. within a single fluid sample)
  splitting of the fluid sample
  combining two or more fluid samples
  sorting fluid samples or particles (or cells) within fluid samples
  atomization
  concentration, including centrifugation In addition, embodiments of the present invention allow sensing of fluid samples (e.g. sensing the location of one or more fluid samples) by considering attenuation of mechanical waves picked up by one or more transducers at the piezoelectric layer.

As stated above, in some preferred embodiments of the present invention the transducer includes a slanted interdigitated arrangement of electrodes, known as a slanted IDT or slanted finger IDT.

Slanted finger IDTs are used in data terminals as mid-band and wide-band filters. The theory of using slanted electrodes in microfluidics has been described [Wu, T. & Chang, I., 2005. Actuating and detecting of microdroplet using slanted finger interdigital transducers. Journal of Applied Physics, 98(2), 024903-7]. However, practical realization of such devices has not been demonstrated, either with droplets directly on piezoelectric or on separate (e.g. disposable) substrates. The inventors investigated the use of slanted IDTs in microfluidics, in particular the use of a slanted IDT in combination with a separable substrate (a substrate sheet, or "superstrate"), as described herein in accordance with certain aspects of the present invention.

The SAW amplitude excited by a slanted IDT is not uniform and different profiles can be obtained by tuning the input frequency. The resonant frequency, f, is dependent upon the pitch of the fingers D, and the sound velocity on the piezoelectric wafer, c (Equation 1, above, reproduced in slightly different form as Equation 1* below). Consequently, for a given input frequency, the SAW output is only generated when the gap (D/2) between the IDT satisfies the ability of the electrodes to support the resonance.

$$2D = \lambda = \frac{c}{f} \qquad \text{Equation 1*}$$

The inventors fabricated divergent IDT electrodes where both the electrode separation (D/2) and their width (D/2) varied linearly from 62.5 micrometer to 125 micrometer along the aperture This corresponds to wavelengths of 250 micrometer to 500 micrometer and a range of frequencies from 16 MHz to 8 MHz on 128 degree Y-cut X-propagating 3 inch LiNbO3 wafer, where c=3990 m/s. Ten pairs of fingers of 15 mm in length were used. The IDTs were patterned using a lift-off process. After pattern transfer into an AZ4562 resist, a 20 nm titanium adhesion layer was evaporated prior to deposition of 100 nm of gold. Liftoff was then performed in acetone, realizing the IDT. The S-parameter was measured to characterize the IDT and showed a stable response for frequencies between 8 MHz and 14 MHz (FIG. 23(b) insert).

Figure 23:
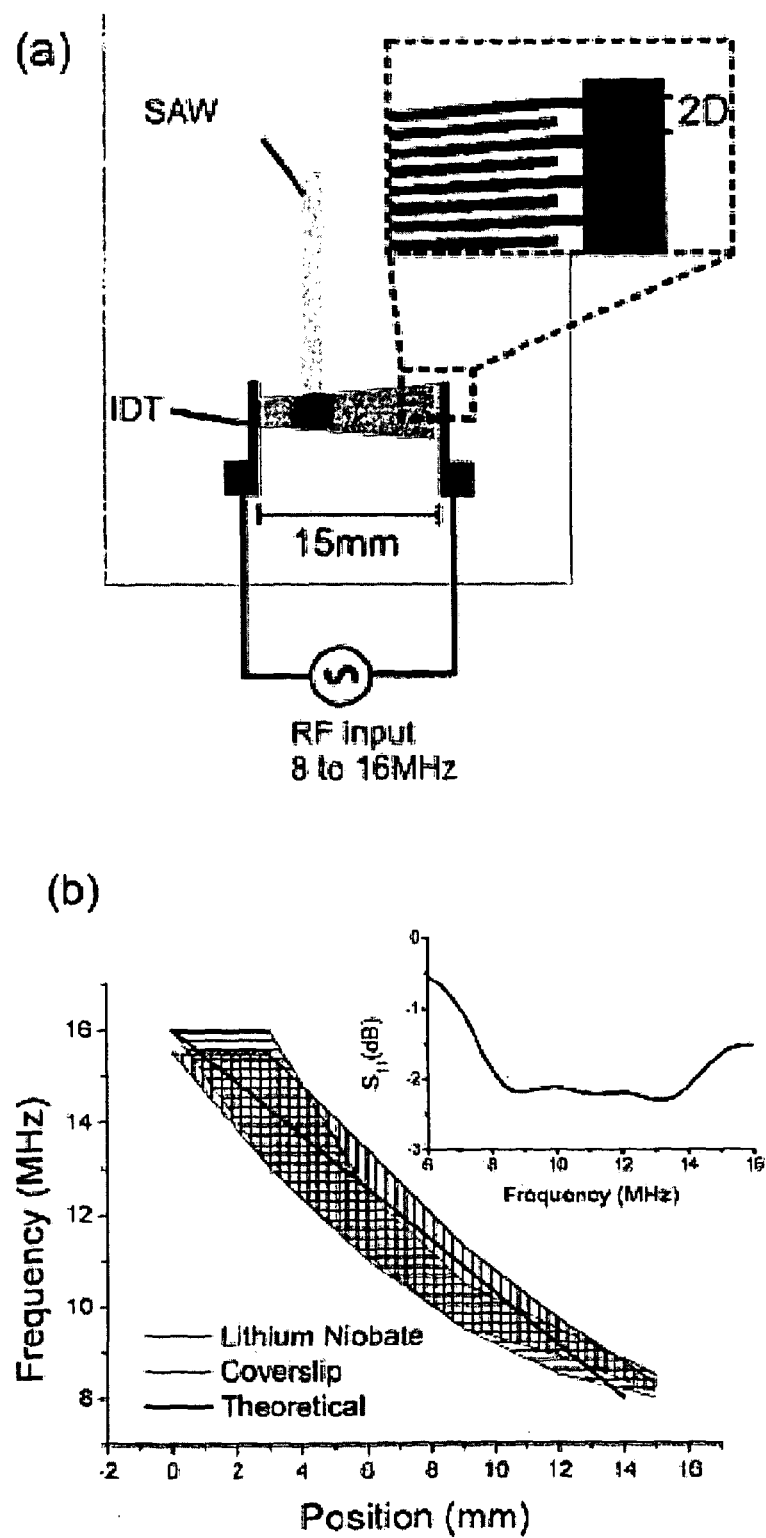
FIG. 23 shows (a) a schematic representation of a device including a slanted IDT, for which the lateral position of the SAW emission train is dependent upon the input frequency; and (b) a graph showing the relationship between input frequency and SAW position as calculated theoretically (line) and as determined experimentally on a lithium niobate transducer (horizontally hatched area) and on a separable substrate coverslip (vertically hatched area). The inset in FIG. 23(b) shows the magnitude of the S-parameter.

FIG. 23a shows a schematic representation of the slanted IDT with the propagation of the SAW on a lithium niobate wafer for a selected input frequency of 13 MHz. Only that part of the IDT that supports the resonance condition is excited, resulting in the propagation of a SAW with a smaller aperture, when compared with a parallel electrode IDT. Thus, by tuning the frequency, it was possible to control the lateral position of the excitation wave, as shown theoretically and experimentally in FIG. 23b.

FIG. 23b shows the experimental input frequency needed to actuate a droplet on the surface of the $LiNbO_3$ wafer, as well as on a coverslip coupled to the $LiNbO_3$ wafer, as a function of the position, and the theoretical calculation of the centre of the SAW pathway. Results for the lithium niobate wafer are shown using horizontal hatching and results for the coverslip are shown using vertical hatching. The theoretical response is shown using a line. The inset in FIG. 23b shows the magnitude of the S-parameter obtained with an Agilent Technologies E5071C ENA series network analyzer. An Agilent Technologies MXG Analog Signal Generator N5181A was used in conjunction with a Mini Circuits ZHL-5W-1, 5-500 MHz amplifier and a 3A, 24V DC power supply to power the SAW device. The wafer was fixed with thermal paste on a heat sink to avoid overheating. The aperture was characterized for each input frequency at a power of −12 dBm, by observing the agitation of an array of 1 microliter droplets arranged in front of the IDT. The inventors then showed that the same spatial control of the SAW, using the excitation frequency, can be extended to applications involving the use of a separable substrate coupled to the $LiNbO_3$ wafer. In this case, an unmodified glass coverslip was used as the separable substrate, and the position of the SAW on the cover slip at given frequencies was directly compared with the SAW position on the native lithium niobate wafer (FIG. 23b). It was found that the lateral width of the SAW beam at a given frequency on the substrate (coverslip) was larger (16% on average) than that directly on the piezoelectric wafer, due to diffraction of the wave in the process of the coupling.

The movable lateral position of the SAW beam using the slanted IDT was then used to actuate a microfluidic droplet. The inventors demonstrated that a tunable IDT can provide SAWs to a droplet to induce rotational streaming in the droplet, and thereby centrifuge particles in the droplet to concentrate them in the centre of the droplet.

Figure 24:
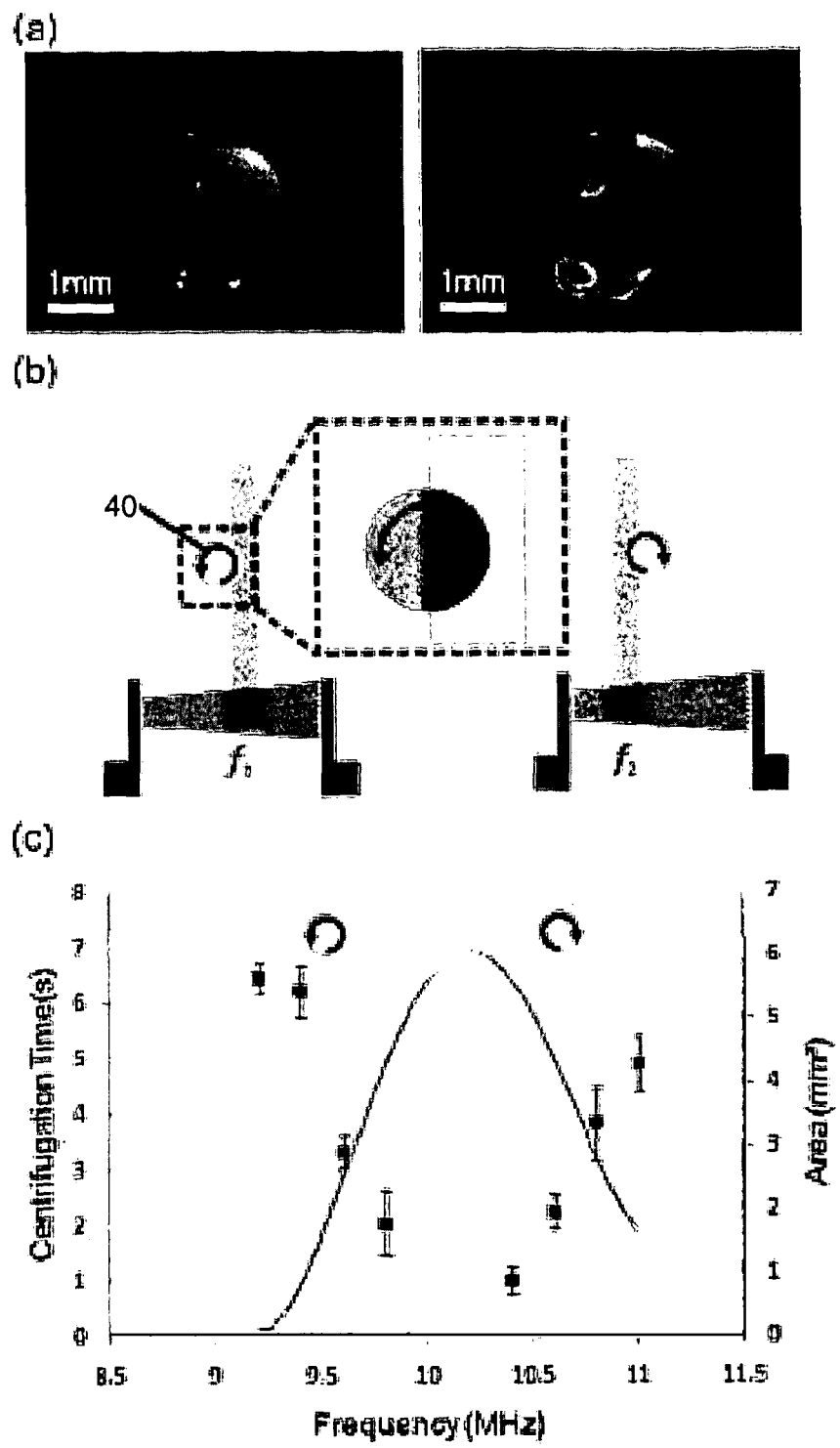
FIG. 24 shows (a) two micrographs of a droplet containing polystyrene beads before (left image) and after (right image) centrifugation using a slanted IDT device; (b) schematic representation of rotational streaming observed, including a magnified representation of the interaction of the SAWs train with the droplet in which counterclockwise rotational streaming takes place; (c) graph showing relationship between input frequency and time taken to concentrate beads in the centre of the droplet (squares) and estimated area of the interface between the wave and the fluid (curve).

The concentration of 10 micrometer polystyrene beads was achieved in 10 microliter water droplets, by locating a droplet a substrate and providing SAWs to the droplet using a slanted IDT and tuning the frequency as shown in FIGS. 24(a) and 24(b). The slanted IDT was fabricated as described above. The droplet was placed directly on the lithium niobate wafer, and contained 3 million beads (Duke Scientific G1000) per milliliter. The droplet was positioned 9 mm from the left of the IDT (i.e. 9 mm from the left edge of the IDT as represented schematically in FIG. 24b). The input frequency was chosen using the results presented in FIG. 23(b) as guide, so that only part of the drop lay in the SAW transmission pathway, thus breaking the symmetry of the acoustic wave.

FIG. 24a is a micrograph of the droplet before (left image) and after (right image) actuation with the SAW. Due to actuation with the SAW (right image) the beads concentrated in the centre of the droplet.

The direction of the streaming was controlled by tuning the input frequency. For example, the SAW excited with a frequency, f1, of 9.6 MHz interacted with the right side of the droplet inducing an angular momentum and created an anti-clockwise streaming. For a SAW excitation frequency of f2 of 11 MHz, the SAW interacted with the left side of the droplet inducing an angular momentum and created a clockwise flow. These two opposite directions of rotation were observed when frequencies f1 and f2 were applied to the droplet sequentially.

FIG. 24(b) shows schematically the observed anticlockwise and clockwise streaming induced by SAW for f1 approximately 9.6 MHz and f2 approximately 11 MHz, respectively. The corresponding streaming direction observed in the droplet 40 is indicated by an arrow. In the left image, the SAW interacts with the right side of the droplet and creates an anti-clockwise streaming, whilst, in the right image, the SAW interacts with the left side of the droplet and creates a clockwise streaming. In the detailed schematic (centre), the overlap area represents the surface of the drop interacting with the SAW The inventors investigated the time taken to concentrate a population of polystyrene beads of diameter 10 micrometer in the centre of a 10 microliter droplet positioned at 9 mm from the left of the IDT directly on the lithium niobate wafer as a function of the input frequency (or the equivalent lateral position of the SAW emission train). The range of frequencies over which excitation occurs depends upon the size of the droplet. For example, using the data presented in FIG. 23b for the device described above, it is estimated that for a droplet having a diameter of 3 mm the SAW will interact with the fluid over a range of frequencies between 9 and 11 MHz. This prediction was confirmed by the experimental results presented in FIG. 24c, which show that centrifugation was only observed at frequencies between 9.2 and 11.0 MHz (the shaded/hatched areas represent frequencies at which no centrifugation was observed).

FIG. 24c is a graph showing the time taken to concentrate 10 micrometer beads in the centre of a 10 microliter droplet positioned at 9 mm from the left of the IDT as a function of the input frequency (equivalent to the position of the SAW) at −18 dBm. The areas shaded/hatched on the graph represent frequencies for which no concentration of beads was observed. The points on the graph show averaged data from three sets of measurements for frequencies between 9.2 MHz to 11.0 MHz with a step of 0.2 MHz, (bars represent the standard deviation from the mean). The data were obtained from videos (25 images per second) analyzed with Time Series Analyzer plug-in in ImageJ software. The curve represents the calculated area of the interface between the wave and the fluid, estimated geometrically.

For frequencies between 10 MHz and 10.2 MHz, although some vibrations were observed in the droplet, no streaming occurred because the SAW was symmetrically transmitted to the droplet (i.e. the SAW distribution was symmetrical with respect to the centre of the droplet) and, consequently, no angular momentum was generated in the droplet. Furthermore, the time needed to achieve a complete centrifugation of beads decreased as the centre of the SAW emission train moved closer to the centre of the drop (in this case there is an asymmetry that creates the angular momentum and hence the rotation). Indeed, as the SAW approaches the centre of the drop, the amount of fluid interacting with the acoustic wave increases, resulting in more energy being transmitted into the droplet. In this respect, the curve in FIG. 24c shows the calculated area of the interface between the wave and the fluid, determined using the input frequency and its correspondence to the lateral position of the SAW emission train shown in FIG. 23b.

Far from being limited to particle concentration, slanted IDT give the opportunity to programme multiple functions with a single electrode. The inventors demonstrated that it is possible to move, merge, mix and centrifuge a droplet on a glass substrate by tuning the frequency of the input signal.

Figure 25:
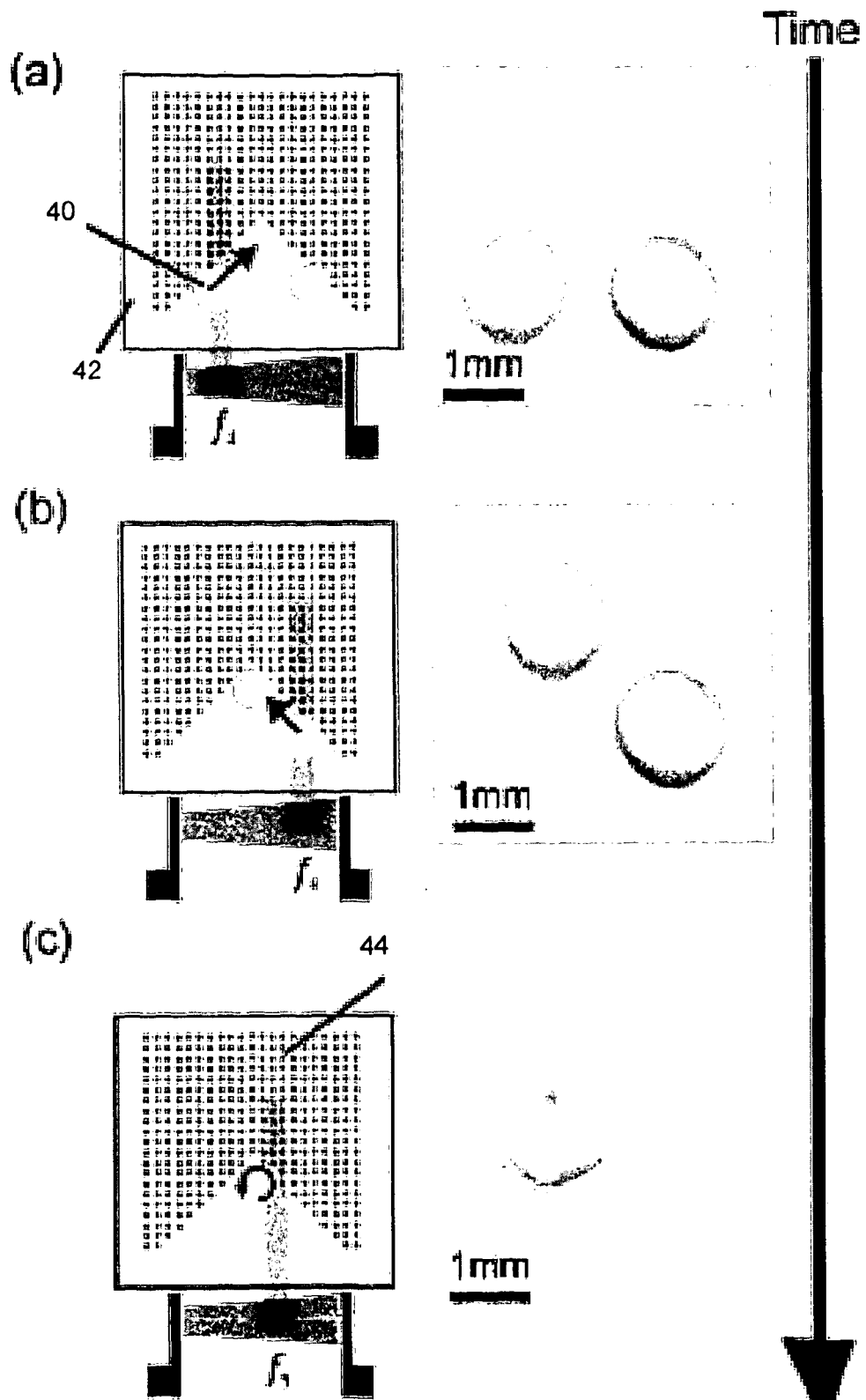
FIG. 25 shows, on the left, schematic representations of the interaction between liquid droplets, a substrate and a slanted IDT device and, on the right, micrographic images from a movie at the different stages during a series of fluid manipulations of droplets on the device. Three different input frequencies were used to navigate between each manipulation. f3 (11 MHz) moves the left hand droplet to the centre, f4 (9.2 MHz) moves the right hand droplet to merge it and f5 (9.6 MHz) mixes the droplet and concentrates reduced silver in the centre of the droplet.

A system comprising a slanted IDT transducer arrangement coupled to a glass substrate was used. With reference to FIG. 25, the hydrophilic glass substrate 42 (coverslip) was decorated with silane using standard lithography to produce an area of hydrophobic dots (80 micrometer radius, 200 micrometer pitch) to create a hydrophobic stop 44, delimiting a track for the drops. (These hydrophobic dots are not necessarily scattering elements within the meaning of the present invention—they are not used to influence the SAW, but to influence the interaction between the droplet and the substrate surface.) A droplet 40 of 2 microliters of hydroxylamine hydrochloride (1.67 mM) and sodium hydroxide (3.33 mM) (pH 9.0) and a droplet of 2 microliters of silver nitrate (10 mM) were pipetted onto the substrate as shown in FIG. 25a. By applying the frequency f3 (11 MHz) at −2 dBm, the left hand droplet (of silver nitrate) was moved towards the centre of the substrate. Upon switching to the frequency f4 (9.2 MHz), the right hand droplet (sodium hydroxide and hydroxylamine hydrochloride) was moved towards the centre of the substrate (FIG. 25b), where it merged with the first droplet (starting the reduction of the silver salt to form colloidal silver). In FIG. 25c, the frequency f5 (9.6 MHz) was used to apply a SAW asymmetrically to the merged droplet to induce streaming in the droplet, resulting in the mixing of reagents and concentration of the silver colloid in the centre of the droplet.

It is possible to integrate the on-chip formation of colloids with both surface enhanced Raman scattering (SERS) and surface enhanced resonance Raman scattering (SERRS) for sensitive bioanalyte detection. The inventors have shown that a slanted IDT, in which the lateral position of the SAW emission train is dependent upon the input frequency, can be used to design complex fluidic functions directly into a chip. The inventors have demonstrated the potential of this powerful tool to manipulate droplets and particles within droplets. In contrast to known techniques, a clear advantage of this flexible method lies in the ability to induce streaming in a droplet in a chosen direction and at any position. Whilst known techniques are also restricted to varying the input power to control the concentration of particles, the inventors have demonstrated that it is possible to control the concentration of particles in a droplet by shifting the position of the SAW (i.e. moving the lateral position of the SAW emission train), and hence its region of interaction with the droplet. The inventors also demonstrated that complex tasks can be programmed sequentially into a single IDT device, by demonstration that two droplets cab be moved, merged, mixed and centrifuged on a substrate (in this case a disposable glass substrate).

This latter example shows the flexibility of the platform for basic fluidic operations needed in lab-on-a-chip technologies.

In the field of SAW microfluidics it has been reported that the SAW Rayleigh wave, which normally propagates in the piezoelectric wafer, can be coupled into a disposable superstrate as a Lamb wave, providing a clear route by which 'lab-on-chip' technology can be applied to low cost, point of care diagnostics. In this known configuration, the surface acoustic excitation in the piezoelectric wafer is usually coupled into the superstrate through a thin liquid film interface. The inventors have now demonstrated a new concept in SAW microfluidics, which combines the use of a separable substrate that is coupled to a transducer arrangement that includes, for example, a slanted finger IDT. In the devices described above, a disposable glass coverslip was used as the separable substrate. The inventors have provided a powerful method by which it is possible to handle droplets and particles in a programmable fashion, and have demonstrated, for example, droplet movement, merging and centrifugation, on the same substrate, with only the need to change the SAW excitation frequency to achieve a high degree of functional integration.

The present inventors have demonstrated the use of surface acoustic waves (SAW) to lyse cells and blood in microliter-sized droplets. Sample preparation is a key component of "lab-on-chip" systems (LOC). More particularly, cell lysis and blood handling are usually required for a wide range of biological assays in diagnostic applications. Recently, chemical-free mechanical methodologies overcame the limitations of translating traditional procedures, involving lytic agents and subsequent washes, on microfluidic platforms, that arose from the detrimental effects of the chemicals on the molecules to be analysed. However, these new techniques often require external pressure-driven systems that constrain their integration into standalone LOC systems, or the use of high energies (heat, electricity or ultrasonication) that may compromise the molecules. The present invention makes use of the acoustic pressure-fields and liquid streaming induced in a droplet by SAW. Methods according to the present invention carried out on biological samples resulted in the lysis of above 99.8% of all cells in the samples. The availability of intracellular material in the resulting suspension was studied with optical absorbance measurements and was comparable to a lab-based chemical procedure. The present inventors also demonstrated that the necessary conditions for lysis can be achieved using different SAW platforms, providing multiple routes to integrate sample preparation in a complete assay on a microchip.

The present inventors show for the first time that cells in diluted whole blood can be lysed mechanically in a small droplet in a matter of seconds, using surface acoustic waves as the actuation mechanism. Cell lysis using acoustic energy was developed previously using ultrasonication (sometimes called 'sonication') either through harsh cavitation at high energies, or by using beads as crushing support. Proceeding differently here, the present inventors created a specific structure of pressure waves and shear stresses, both red blood cells and white blood cells can be lysed, without cavitation and without the addition of materials to the sample. The lysis efficiency of method of the invention was compared to chemical means by measuring the free haemoglobin in suspension, while the number of cells remaining after treatment showed a 95% lysis, comparable to other mechanical solutions.

Figure 26:
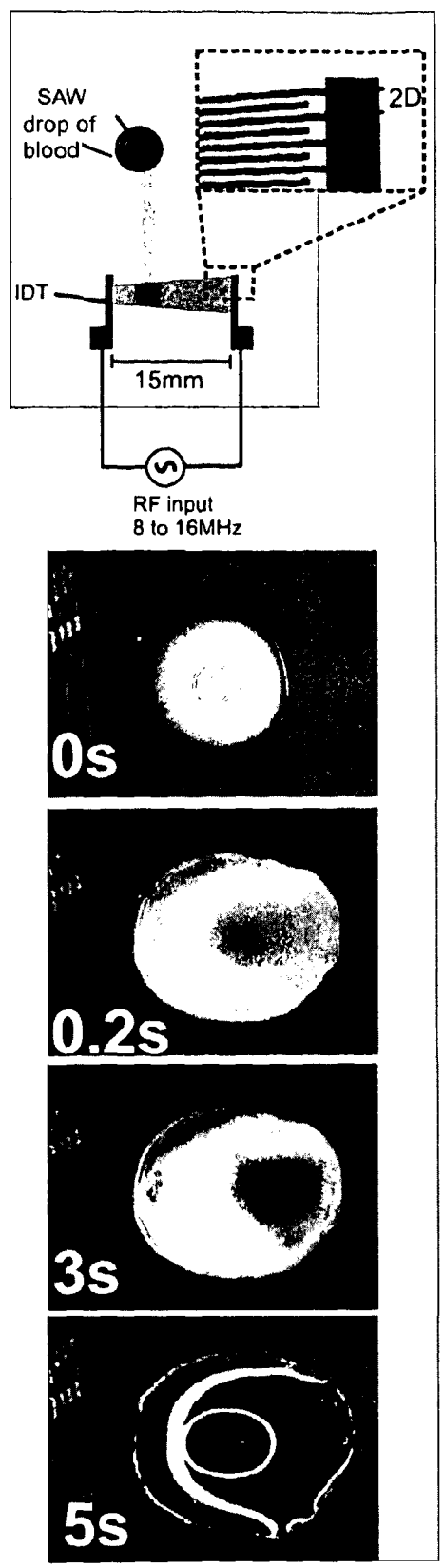
FIGS. 26, 27 and 28 shows three preferred embodiments of the invention. In each drawing, a schematic view of each embodiment is shown at the top of each panel, followed by four consecutive micrographic frames from video recordings of cell lysis. Near the bottom of each schematic view is shown a transducer arrangement, which is a slanted finger IDT in the case of FIG. 26, and a parallel electrode IDT in the case of FIGS. 27 and 28. The SAWs emission train is indicated emanating from the transducer arrangement in each case. A circular droplet of blood is shown a near the top of each schematic view, and the direction of rotational streaming induced in the droplet by the SAWs is indicated by an arrow.
Figure 27:
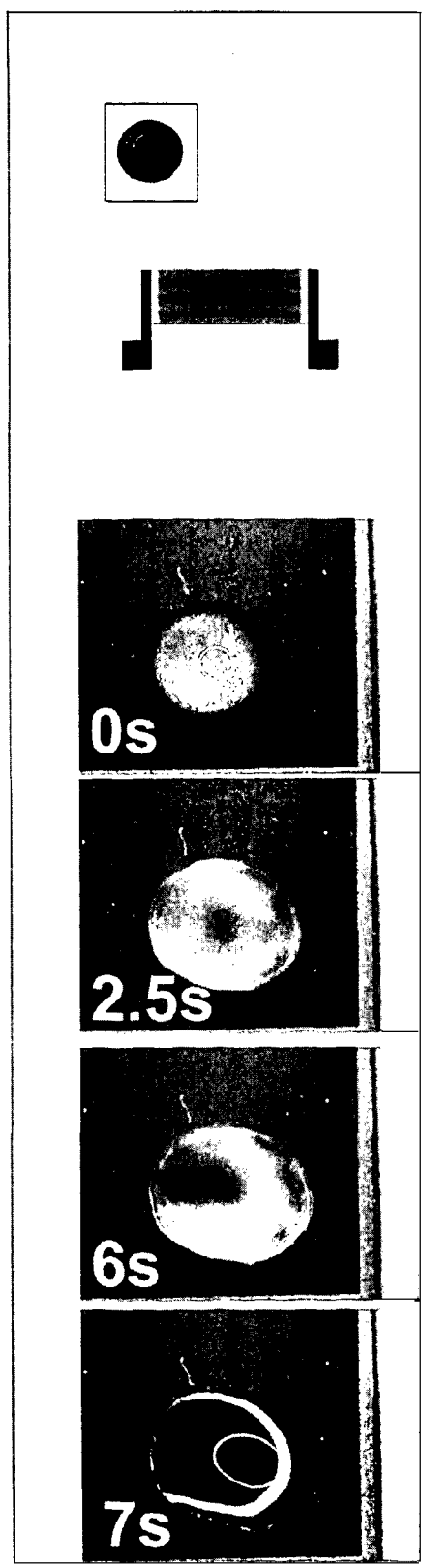
Figure 28:
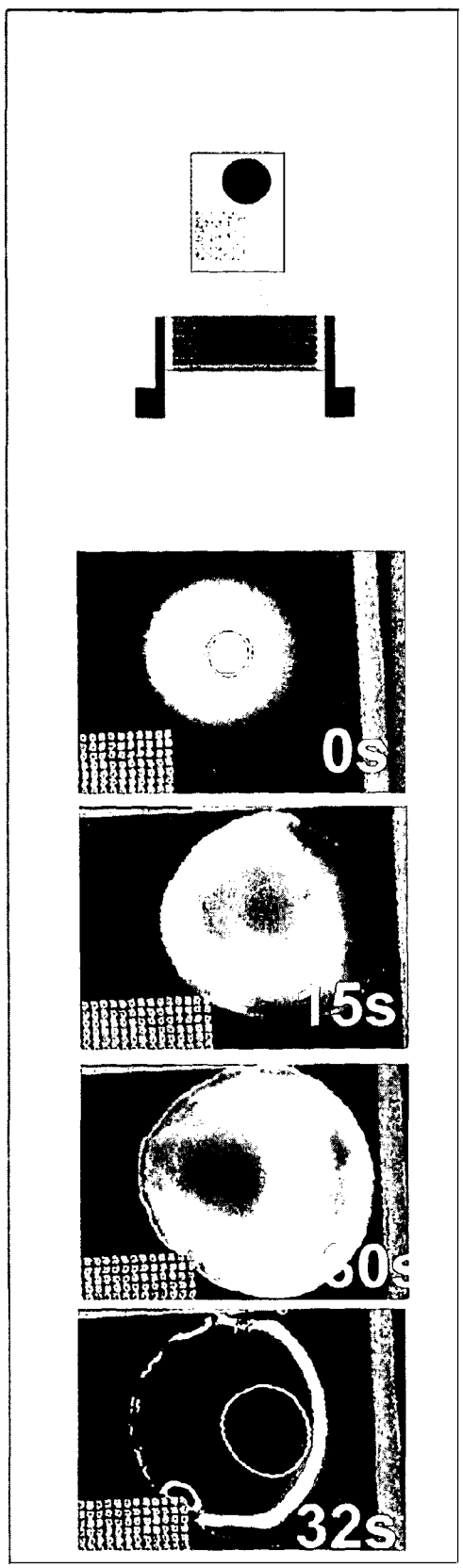

Interestingly, lysis was achieved in many configurations of SAW microfluidics (FIGS. 26, 27 and 28). Namely, directly on the piezoelectric transducer (FIG. 26), on an unstructured substrate coupled to the piezoelectric transducer and placed strategically to interact with the SAW (FIG. 27), and on a substrate comprising a phononic crystal and coupled to the piezoelectric transducer (FIG. 27). Thus, the cell lysis method of the invention can be easily integrated with other functionalities in a single SAW system.

FIGS. 26, 27 and 28 show the arrangement of apparatus for use according to three respective preferred embodiments of the invention. The top of each figure shows a schematic view of the apparatus arrangement. The remainder of each figure includes four images, which are micrographs extracted from video recordings of blood cells being lysed according to an embodiment of the present invention. Each image shows a 10 microliter droplet of diluted blood (whole blood dilulted 50 times in PBS). In each case, a rotational movement was incurred to the fluid inside the droplet as follows: in the embodiment shown in FIG. 26, using a slanted IDT exited at 11.6 MHz with a power of −9 dBm; in the embodiment shown in FIG. 27, using a substrate coupled to a parallel electrode IDT excited at 9.61 MHz with a power of −6 dBm and positioned on the side of the aperture of the SAW; and in the embodiment shown in FIG. 28, using a substrate comprising a phononic crystal, coupled to a parallel electrode IDT excited at 12.5 MHz with a power of −7 dBm. In the embodiments shown in FIGS. 27 and 28, the substrates were coupled to the SAW on the piezoelectric transducer by a thin film of deionised water. The timescales give an idea of the speed of the lysis, but are not suitable for direct comparison between different apparatus configurations because lysis conditions were not optimised. The droplet at the beginning of the experiment (0 s) is about 4 mm in diameter.

Surface acoustic waves were propagated on a $LiNbO_3$ piezoelectric wafer. Upon reaching a droplet of liquid on the propagating surface, they are refracted as pressure waves inside the droplet at a specific angle depending on speed of sound in both materials. By adjusting the power input in the device and the surface tensions at the droplet pinning contact line, different wave amplitudes give rise to different phenomena, from streaming at low powers to movements, jetting and nebulisation in the high range. These behaviours are the result of the pressure field created in the droplet. Here the inventors made use of the pressure distribution inside the liquid when streaming is induced, to create vortexes. In their simplest states, these vortexes are used to concentrate particles in the centre of the droplet. FIGS. 26, 27 and 28 show that blood cells were moved to the centre of the droplet at the beginning of the actuation (second micrograph from top).

When the power was increased, the conditions of pressures and shear stress at the centre of the vortexes were such that cells were crushed and mechanically disrupted, as shown in FIGS. 26, 27 and 28 (third micrographs from top), resulting in cell lysis. The turbid appearance of the droplets at the beginning of the process (top micrographs), due to the presence of intact blood cells, contrasts with their eventual clear appearance once the cells were lysed (bottom micrographs).

The vortexes used in this study were induced by a concentration streaming in the droplet, achieved when the propagating SAW symmetry was broken. Although it is not shown in the figures, lysis was also obtained when multiple vortexes were formed in other configurations where the SAW hit the droplet in a more symmetrical manner.

In the above described embodiments, rotational streaming was induced in sample droplets by providing a SAW beam, or SAW emission train, to the droplet asymmetrically. In particular, the SAW beam provided to the droplet only partially overlapped with the droplet footprint, as shown schematically in FIGS. 26-28.

The notional lateral width of the SAW beam, or SAW emission train, emitted by the transducer is determined by the lateral width of the aperture of the transducer (that part of the transducer which resonates and produces SAWs). Whist it is understood that the edge of a SAW beam is not sharp (i.e. SAWs may propagate at lateral locations beyond the lateral width of the transducer aperture), as explained below, in the context of the present invention a SAW beam, or SAW emission train, is defined has having a lateral width that corresponds to the lateral width of the transducer aperture. For parallel electrode IDTs, this width corresponds to the lateral extent of overlap between electrode fingers (w, FIG. 6). For slanted electrode IDTs this width corresponds to the lateral with of the resonating part of the transducer, considered above in relation to the full width at half maximum of the amplitude distribution laterally across the SAW beam. In this case a SAW beam can be understood as overlapping with a droplet footprint when the centre of the beam overlaps with the droplet foot print. In the context of the present invention the provision of a SAW beam that partially overlaps with a droplet footprint encompasses the use of a phononic lattice to scatter a SAW beam such that the droplet receives a distribution of SAWs that is asymmetrical with respect to the centre of the droplet.

In the above described devices, the interdigitated transducers (IDT's) were designed to emit SAW's in Y cut Lithium Niobate propagating in the Z direction and therefore the emitted SAW beam should be diffractionless. The wavelength of the surface acoustic waves emitted from the IDT's were of the order 400 micrometers where the length of propagation of the SAW prior to irradiating a droplet was never more than 75 wavelengths (near field), implying that diffraction and beam steering losses are not significant even for anisotropic mediums, where the direction of propagation is not along a principle axis. Assuming that the beam amplitude maxima of the emitted SAWs are commensurate with the IDT aperture then a −3 dB drop off in power would be observed less than 5 wavelengths away from the edge of the IDT aperture and by extrapolation 0 dB 10 wavelengths away from the edge of the aperture. Therefore it was possible to generate SAWs of useful power between 10 and 0 wavelengths from the edge of the aperture. The useful power is also be dependent on the amount of power applied to the IDT as this will directly influence the power available at the edge zones of the SAW beam.

Figure 29:
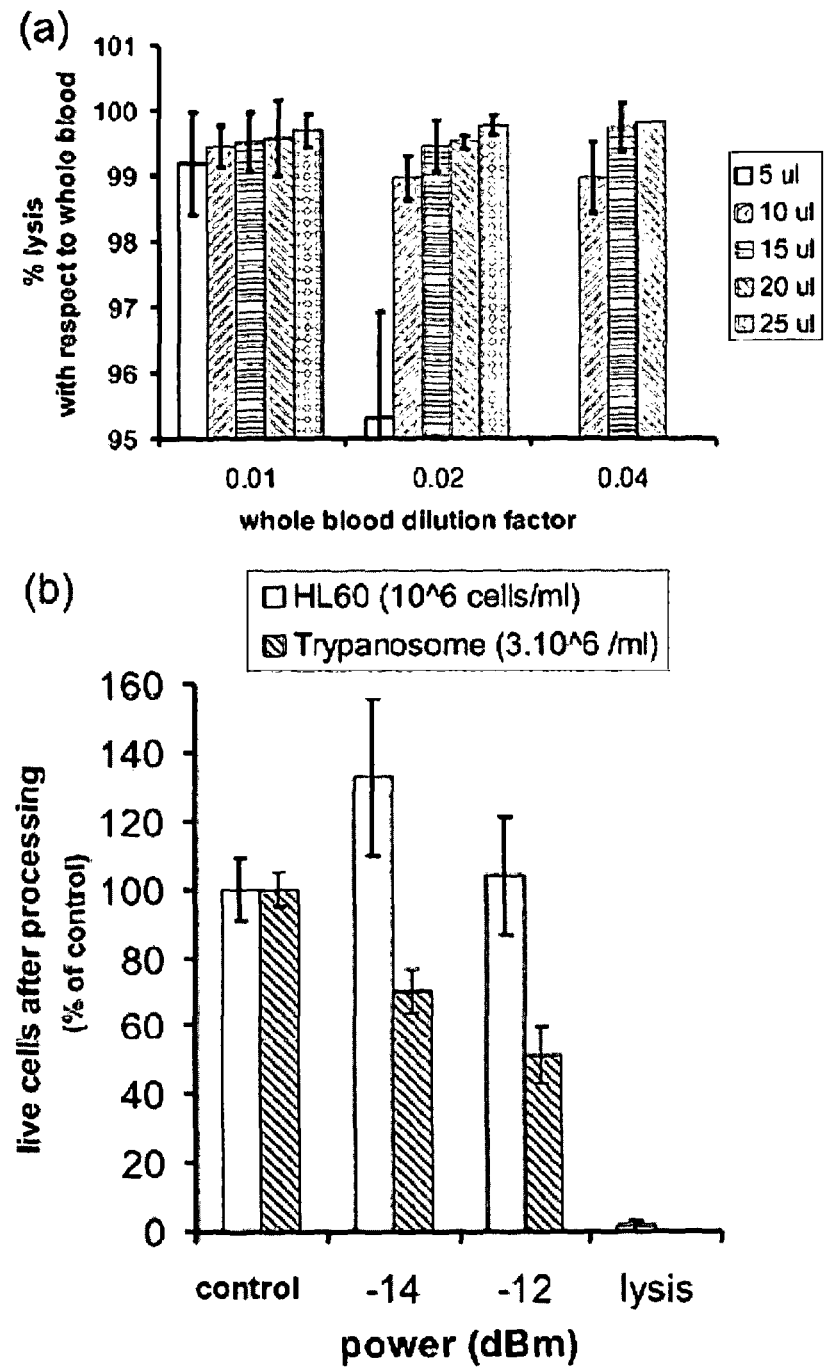
FIG. 29 shows cell lysis efficiency of the invention evaluated by (a) reporting the proportion of cells lysed for different cell types, droplet volumes, and sample dilutions (b) reporting the proportion of live (unlysed) cells remaining following treatment using different input powers.

FIG. 29(*a*) shows the lysis efficiencies achieved for diluted whole blood sample droplets processed on a slanted IDT, using a range of droplet volumes and dilution factors. Error bars represent the standard deviation over three samples.

Results shown in FIG. 29(*a*) attest the very high rate of cell lysis for most of the conditions tested, above 98%, and above 99.8% (±0.4%) for the optimised condition (20 microliter sample at a power of −9 dBm). This compares well with other non-chemical methods [M. T. Taylor, P. Belgrader, B. J. Furman, F. Pourahmadi, G. T. A. Kovacs and M. A. Northrup, Lysing Bacterial Spores by Sonication through a Flexible Interface in a Microfluidic System, *Analytical Chemistry* 2001, 73, 492-496 and M. T. Taylor, Apparatus and method for rapid disruption of cells or viruses, WO03055976 (Cepheid, Inc.)], and even chemical methods [J. Siegrist, R. Gorkin, M. Bastien, G. Stewart, R. Peytavi, H. Kido, M. Bergeron and M. Madou, Validation of a centrifugal microfluidic sample lysis and homogenization platform for nucleic acid extraction with clinical samples, *Lab on a Chip,* 2010, 10, 363-371; cut-off for efficient lysis at 99.5%].

The inventors measured the cell lysis efficiencies achieved for droplets having different volumes when positioned on a hydrophilic spot having a diameter of 4 mm. FIG. 29(*a*) shows that when the blood sample droplet volume was 5 microliters, if the dilution factor was 1:50 or 1:25 then the lysis efficiency was relatively low. The lysis efficiency achieved using a 5 microliter droplet of blood diluted 1:25 was 45% (this is not visible in FIG. 29(*a*) due to the vertical axis scale used). For droplet volumes up to 10 microliters, the droplet was confined to the hydrophilic spot, its edges pinned to the outline of the spot. It is believed by the inventors that the observed relationship between droplet volume and cell lysis efficiency can be explained by vortex creation in the droplet having a dependency on the contact angle of the droplet with the substrate surface, since the contact angle of the droplet influences the propagation of the pressure wave from the incident SAW. The contact angle of the droplet increased as its volume was increased up to the point where the droplet could no longer be bound to the hydrophilic spot by surface tension and spilled out onto the hydrophobic part of the substrate surface. For volumes below 5 microliters, no lysis was achieved in this particular configuration, although it is believed that lysis may be achieved using volumes below 5 microliters by using alternative configurations (e.g. hydrophilic spot of lower diameter).

The lysis of other cell types was demonstrated by processing both a mammalian cell line (HL60 cells, a model for chronic myeloid leukaemia), which is non-adherent and mechanically (i.e. in terms of size, shape and deformability) closer to white blood cells than red blood cells, and cultured trypanosomes (*Trypanosome cyclops*, a model for parasite-born infectious diseases such as sleeping sickness), which is a motile organism.

The inventors demonstrated that both these cell types can be lysed using SAW, thus confirming that the method of the invention is generally applicable to cells.

FIG. 29(*b*) shows the lysis achieved for a 15 microliter droplet of a solution containing either 1 million HL60 cells per milliliter in PBS, or 3 million trypanosomes per milliliter in PBS, processed on a slanted IDT for 10 seconds. Results are expressed as a proportion of live cells after processing, expressed relative to an unprocessed control sample (e.g. 100% live cells after processing corresponds to 0% lysis efficiency). The trypanosomes were lysed at lower powers than the mammalian cells. At a power of −14 dBm, cells were concentrated in the centre of the droplet, but there was no significant lysis of HL60 cells and the majority of trypanosomes did not lyse. At a power of −12 dBm, there was no significant lysis of HL60 cells, and around half of the typanosomes lysed. At a power of −8 dBm for HL60 cells, and −10 dBm for trypanosomes, effectively all the cells were lysed (98.3%±1.4% of HL60 cells were lysed, and 99.9%±0.14% of trypanosomes were lysed). The last data point (0.06%±0.14% live cells) for the trypanosomes is not visible in FIG. 29(b).

The availability of intracellular material in the droplet solution after cell lysis on the SAW device was studied by spectroscopy. For blood samples, the inventors measured the absorbance of the solutions at different wavelengths to evaluate the presence of haemoglobin (414 nm and 540 nm) as well as total DNA (260 nm) and protein contents (280 nm). Haemoglobin is contained in red blood cells and is the most widely used marker of red blood cell lysis. Spectroscopy is used routinely to evaluate haemoglobin levels in plasma as a diagnostic tool for haemolysis.

Figure 30:
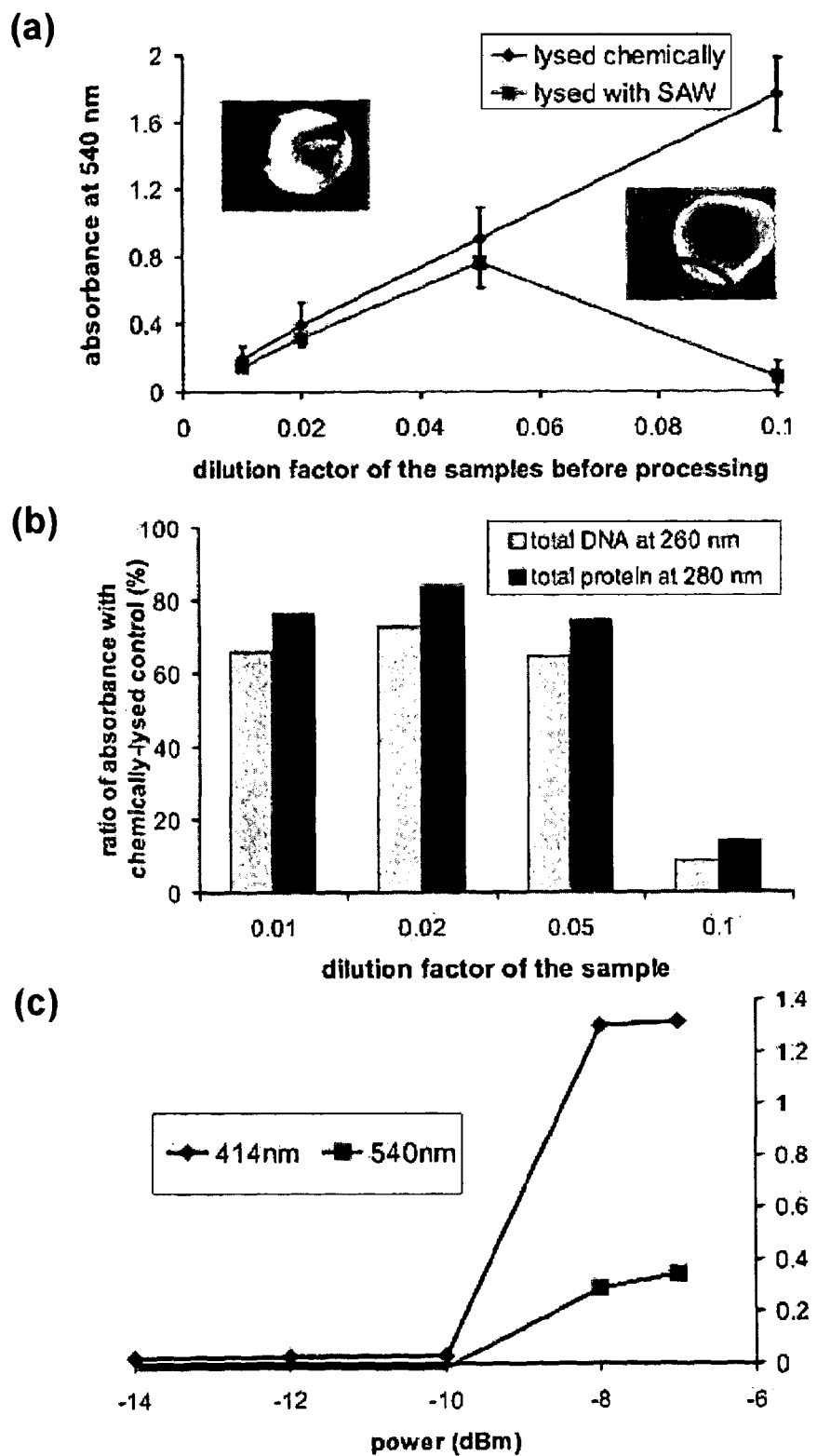
FIG. 30 shows efficiency of release of intracellular molecules, as determined spectroscopically by measuring in cell samples following lysis the absorbance at particular wavelengths, indicating concentrations of haemoglobin, DNA or protein.

FIG. 30(a) shows the levels of haemoglobin in 20 microliter samples of blood diluted to various ratios with PBS and lysed using SAW on a slanted IDT at −8 dBm (0.8 W), relative to samples in which cells were lysed chemically with the detergent Triton X-100. For blood:PBS (or blood:PBS+Triton X-100) dilutions of 1:20 and higher (dilution factor <0.05), the samples lysed with SAW are indistinguishable from chemically lysed samples. For blood:PBS dilutions of 1:10, the lysis efficiency was considerably lower. A similar observation was made for measurements of nucleic acids or proteins (FIG. 30(b)). The inventors believe that the improved lysis efficiency observed for higher dilution factors can be explained by higher sample concentrations impeding the formation of the vortexes required for lysis, because the blood cells formed clusters that disrupted the flow and prevented efficient streaming. The inserts in FIG. 30(a) show micrographic images captured during the lysis experiments, where the right insert shows higher blood concentration and cell aggregation (highlighted by ring).

By varying the power of the SAW, it is possible to find conditions where the samples are only centrifuged and not lysed. FIG. 30(c) shows the levels of haemoglobin in 20 microliter sample of whole blood diluted 1:50 in PBS (dilution factor 0.2) and lysed using SAW on a slanted IDT at a range of different powers for 10 seconds. Under these particular conditions, red blood cells did not lyse at powers below −10 dBm. Since SAWs can be used to manipulate samples containing cells without causing cell lysis, the cell lysis method of the present invention can be integrated in to a complex sequence of fluidic manipulation in a biological assay.

For example, the cell lysis method of the invention can be integrated into a sequence of fluid manipulation steps including steps of moving, mixing, centrifuging, selectively concentrating, fractionating (i.e. selective concentration of species according to their size or mass) and nebulising (atomising) a droplet comprising live intact (unlysed) cells and/or lysed cells. A method comprising a series of steps comprising one or more droplet manipulation steps and one or more cell lysis steps may be conveniently performed on a microfluidics apparatus. One or more analysis steps may also be included, such as microscopic or spectroscopic analyses. In particular, a droplet comprising lysed cells, or downstream (e.g. fractionated) products of lysed cells, may be atomised to create a plume of atomised sample, which can be captured in ion-funnels to provide an innovative interface between low volume (e.g. single cell) biology and mass spectrometry. Analysis steps may include microarray-based analysis, for example of intracellular proteins or nucleic acids released from cells lysed according to the present invention. Analysis steps may include immunological detection steps (e.g. ELISA), gel electrophoresis, electrochemical detection, PCR or other amplification-based techniques. Such analysis may be of particular use in point-of-case diagnostic applications (e.g. to detect an intracellular molecule indicative of a pathogenic cell in the sample) and portable biosensors (e.g. to detect an intracellular molecule indicative of the presence of a biological contaminant or weapon in a sample)

The dissipation of acoustic energy in a liquid droplet generates heat, increasing temperature, all the more so with increased viscosities. In configurations where a heat sink was not used (because the substrate was coupled to the piezoelectric transducer via a coupling medium), the temperature of blood droplets during the SAW actuation was recorded using an infrared camera, and confirmed that the lysis observed was not die to an increase in temperature in the droplet. For a 15 µl sample of blood diluted 1:50 in PBS, and processed at −9 dBm on a slanted IDT, the temperature of the sample increased to around 40° C. in 5 s and 50° C. in 10 s, which is already a long timescale for SAW-based lysis (see FIG. 26). The temperatures encountered are well below those employed for cell lysis [L. C. Waters, S. C. Jacobson, N. Kroutchinina, J. Khandurina, R. S. Foote, and J. M. Ramsey, Microchip Device for Cell Lysis, Multiplex PCR Amplification, and Electrophoretic Sizing, *Anal. Chem.*, 1998, 70 (1), 158-162]. These results confirmed that the cell lysis observed was not due to an increase in temperature in the droplet.

Further details relating to the preferred embodiments of the method are set out below.

The SAW was propagated on piezoelectric 128° Y-cut X-propagating 3 inch LiNbO$_3$ wafers. For transmission microscopy, 4 inch double-sided polished wafers were used. The devices consisted of 20 pairs of electrodes to form an inter-digitated transducer (IDT) with a pitch of 200 micrometers, 100 micrometers width, and a 10 millimeter aperture, yielding a frequency of ~10 MHz for the propagating SAW (measured as 9.61 MHz). The transparent slanted electrode IDT contained 20 pairs of electrodes, with a pitch from 150 micrometers at the highest frequency (about 13 MHz) and 222.5 micrometers at the highest frequency (about 9 MHz) at the lowest, with an aperture of 3 cm. The fingers width varied accordingly from 75 micrometers to 111 micrometers.

The phononic crystal superstrate comprised a square array (pitch 203 micrometers) of circular holes (radius 82 micrometers) in a 470 micrometer-thick silicon wafer that scattered the SAW to obtain an asymmetry in the propagating waves. The specific mechanical forces acting on the cells arose from a rotational streaming in the droplet.

The surface holding the sample droplet was patterned with a hydrophilic spot of 4 mm in diameter, surrounded by a silane (FOTS, Sigma), obtained by immersing the photoresist-patterned (AZ4562) wafer in a 1.6 mM silane solution in heptane (Sigma, H9629) for 10 min and dissolving the resist in acetone. This treatment resulted in a contact angle of 107°±0.2° (standard deviation) on silicon and 98°±1.4° on LiNbO$^3$. The hydrophilic spot prevents the droplet from moving at higher powers, but is not essential for lysis.

The temperature of a droplet excited by a SAW can increase drastically, depending on the viscosity of the liquid [J. Kondoh, N. Shimizu, Y. Matsui, S. Shiokawa, Liquid Heating Effects by SAW Streaming on the Piezoelectric Substrate, *IEEE transactions on ultrasonics, ferroelectrics, and frequency control*, 2005, 52 (10)]. The heat generated was dissipated through a metal heat sink on which the piezoelectric device was pasted with a heat sink compound (RS Components Ltd., 554-311). In cases where the full heat dissipation is not possible (for example where the substrate was separable from the piezoelectric transducer, and coupled to it by a coupling medium), an infrared camera (FLIR i60, FLIR Systems) was used to evaluate the extent of heat increase on the device. As mentioned, lysis was achieved in different configurations, illustrated in FIGS. 26-28. The IDT was connected to an Agilent Technologies MXG Analog Signal Generator N5181A in conjunction with a Mini Circuits ZHL-5W-1, 5-500 MHz amplifier and a 3A, ±24V DC power supply. The lysis was observed under a stereomicroscope (Leica MZ 12).

When a substrate, either unpatterned or with a phononic lattice, that is separable from the piezoelectric wafer was used, it was placed on top of the piezoelectric wafer and coupled with 2-5 microliters of water in between, yielding water film approximately 50 micrometers thick. During experiments with blood, the wafer was placed in a transparent container for safety concern EDTA-chelated human whole blood ($O^+$) was obtained from the Glasgow and West of Scotland Blood Transfusion Service and stored at 4° C. until needed. Samples were discarded after a week. HL60 cells (ATCC CCL-240, acute promyelocytic leukemia) were maintained following the supplier's recoomendations, in Dulbecco's RPMI media supplemented with 10% heat-inactivated fetal calf serum (FCS) and 5% penicillin-streptomycin, at 37° C. (5% $CO_2$). Trypanosomes were maintained at 27° C. in Cunninghams media +20% FCS.

Haemoglobin released from the red blood cells was quantified by measuring direct light absorption at 414 nm and 540 nm [E. Eschbach, J. P. Scharsack, U. John, L. K. Medlin, Improved Erythrocyte Lysis Assay in Microtitre Plates for Sensitive Detection and Efficient Measurement of Haemolytic Compounds from Ichthyotoxic Algae, *J. Appl. Toxicol.*, 2001, 21, 513-519]. Although the standard methodology [Standard F756-08, Standard Practice for Assessment of Hemolytic Properties of Materials, ASTM, March 2009] uses 540 nm as the observation wavelength, it necessitates the intermediate step of adding a reagent to improve the signal, which also lyses the cells. In order to avoid the bias of an additional chemical lysis, a direct measurement was adopted. Total protein and DNA contents are reported by the absorbance of the samples at 260 nm and 280 nm.

A range of blood dilutions was processed on the SAW system. Six samples of 20 microliters of each dilution were lysed at the power specified in the text at −8 dBm (0.8 W) collected (pooled) in an Eppendorf tube and diluted 5 times to fit in the spectrophotometer cuvette (500 microliters). The extent of lysis was compared to a chemical method. The diluted blood samples were mixed (1:1 v/v) with a solution of 6% (w/w) Triton X-100 (Sigma, T-9284) in PBS and agitated for 5 min. Finally a plasma sample was prepared by centrifuging the blood at 1000 g for 10 min.

All samples were centrifuged at 1000 g for 10 min prior to measurement in the spectrophotometer (Hitachi, U-2000), which was blanked with PBS. The absorbance for the chemically lysed samples is reported after subtracting the value for a solution of 3% Triton X-100.

The extent of lysis was also studied by counting the cells remaining intact after the SAW treatment. For experiments measuring lysis of blood cells (FIG. 29*a*) different volumes of diluted blood were processed on the SAW system with a slanted IDT (11.6 MHz, −9 dBm). After resuspension of the contents of the droplet, 10 microliters of the solution was harnessed and inserted into a heamocytometer (Neubauer improved). The remaining cells were counted and the extent of lysis reported as a percentage with regards to the cell contents of the original solution. Other types of cells were also lysed and the lysis efficiency studied in a similar fashion (FIG. 29*b*). HL60 cells at a concentration of 1 million cells/ml in PBS, trypanosomes (cyclops) at a concentration of 3 million/ml. In these experiments, the extent of lysis was evaluated by determining the number of live (non-lysed) cells present at the end of the process and expressing it as a percentage of the number of live cells in an control sample that had not been treated with SAWs. The values higher than 100% live cells for HL60 cells treated using low powers may be explained by sampling variability and/or evaporation of the sample on the chip during treatment concentrating the contents of the SAW-treated droplets. Live (unlysed) cells were distinguished from dead (lysed) cells using Trypan blue.

The preferred embodiments of the invention have been described by way of example. Modifications of these embodiments, further embodiments and modifications thereof will be apparent to the skilled person on reading this disclosure and as such are within the scope of the present invention.

ABBREVIATIONS

ATP Adenosine triphosphate
ADP Adenosine diphosphate
cAMP Cyclic adenosine monoposphate
ELISA Enzyme-linked immunosorbent assay
IDT Interdigitated transducer (also known as an interdigital transducer)
PBS Phosphate buffered saline
PCR Polymerase chain reaction
SAW Surface acoustic wave

The invention claimed is:

1. A fluidics apparatus for manipulation of at least one fluid sample, the apparatus including a substrate having a substrate surface with a sample manipulation zone for location of the fluid sample and a transducer comprising a layer of piezoelectric material and at least one array of electrodes to provide surface acoustic waves at the substrate surface to manipulate the fluid sample, wherein the substrate surface has a two dimensional periodic arrangement of surface acoustic wave scattering elements for affecting the transmission, distribution or behaviour of surface acoustic waves at the substrate surface, and wherein the substrate is separable from the transducer and the substrate is in the form of a sheet having a first major surface and a second major surface, formed substantially parallel with each other, the first major surface providing the sample manipulation zone and the arrangement of surface acoustic wave scattering elements, the second major surface providing a coupling surface, for coupling with the transducer in operation.

2. The apparatus according to claim 1 wherein the surface acoustic wave scattering elements are arranged in a scattering zone at the substrate surface, the scattering zone providing in use a different transmission, distribution or behaviour of surface acoustic waves compared with the sample manipulation zone.

3. The apparatus according to claim 1 wherein the transducer provides surface acoustic waves at the substrate surface to manipulate the fluid sample by one or more of: movement of the sample along the sample manipulation zone; splitting of the sample; combining two or more samples; atomisation of the sample from the sample manipulation zone; heating of the sample; concentration of species in the sample; mixing of the sample; sorting fluid samples; sorting particles or cells within fluid samples.

4. The apparatus according to claim 3 wherein the substrate has a series of sample manipulation zones, in communication with each other, the fluid sample being transferrable from one sample manipulation zone to the next.

5. The apparatus according to claim 1 wherein the transducer is formed from a piezoelectric material having an arrangement of interdigitated electrodes.

6. The apparatus according to claim 1 wherein coupling is achieved in use with a liquid coupling medium.

7. A method for manipulating at least one fluid sample using a fluidics apparatus comprising;
providing a substrate having a substrate surface with a sample manipulation zone;
placing a fluid sample in the sample manipulation zone;
providing a transducer comprising a layer of piezoelectric material and at least one array of electrodes to project surface acoustic waves to the substrate surface; wherein the substrate surface has a two dimensional periodic arrangement of surface acoustic wave scattering elements affecting the transmission, distribution or behaviour of surface acoustic waves at the substrate surface, and wherein the substrate is separable from the transducer and the substrate is in the form of a sheet having a first major surface and a second major surface, formed substantially parallel with each other, the first major surface providing the sample manipulation zone and the arrangement of surface acoustic wave scattering elements, the second major surface providing a coupling surface, for coupling with the transducer in operation;
manipulating the fluid sample by projecting surface acoustic waves from the transducer to the substrate surface; and
separating the substrate from the transducer.

8. A fluidics substrate for manipulation of at least one fluid sample, the substrate being selectively couplable with a transducer comprising a layer of piezoelectric material and at least one array of electrodes providing surface acoustic waves at a surface of the substrate for manipulation of the fluid sample, wherein the substrate surface has a sample manipulation zone for location of the fluid sample, wherein the substrate surface further has a two dimensional periodic arrangement of surface acoustic wave scattering elements for affecting the transmission, distribution or behaviour of surface acoustic waves at the substrate surface, wherein one or more of the scattering elements comprises a filled void at the substrate surface and wherein the substrate is in the form of a sheet having a first major surface and a second major surface, formed substantially parallel with each other, the first major surface providing the sample manipulation zone and the arrangement of surface acoustic wave scattering elements, the second major surface providing a coupling surface, for selectively coupling the substrate to the transducer.

9. The method of claim 7 wherein the step of manipulating the fluid sample includes one or more of; moving of the fluid sample along the sample manipulation zone; splitting of the fluid sample; combining two or more fluid samples; atomizing the fluid sample from the sample manipulation zone; heating the fluid sample; concentrating species in the fluid sample; mixing the fluid sample; sorting two or more fluid samples; and sorting particles or cells within the fluid sample.

* * * * *